(12) United States Patent
Yahata et al.

(10) Patent No.: US 11,720,984 B2
(45) Date of Patent: Aug. 8, 2023

(54) METHOD OF PROVIDING INFORMATION

(71) Applicant: Panasonic Intellectual Property Management Co., Ltd., Osaka (JP)

(72) Inventors: Hiroshi Yahata, Osaka (JP); Takahiro Nishi, Nara (JP); Tadamasa Toma, Osaka (JP); Toshiyasu Sugio, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 17/695,285

(22) Filed: Mar. 15, 2022

(65) Prior Publication Data

US 2022/0284522 A1    Sep. 8, 2022

Related U.S. Application Data

(63) Continuation of application No. PCT/JP2021/016259, filed on Apr. 22, 2021.

(30) Foreign Application Priority Data

Mar. 8, 2021    (JP) .................................. 2021-036752

(51) Int. Cl.
G06Q 50/12       (2012.01)
G16H 10/60       (2018.01)

(52) U.S. Cl.
CPC ............. *G06Q 50/12* (2013.01); *G16H 10/60* (2018.01)

(58) Field of Classification Search
CPC ......... G06Q 50/12; G16H 10/60; G16H 20/60
(Continued)

(56) References Cited

U.S. PATENT DOCUMENTS 7,953,873 B1    5/2011    Madurzak
8,200,548 B2    6/2012    Wiedl
(Continued)

FOREIGN PATENT DOCUMENTS

CN    103370703    10/2013
CN    107945057 A    4/2018
(Continued)

OTHER PUBLICATIONS

International Search Report of PCT application No. PCT/JP2021/016259 dated Jul. 20, 2021.
(Continued)

*Primary Examiner* — Ariel J Yu
*Assistant Examiner* — Denisse Y Ortiz Roman
(74) *Attorney, Agent, or Firm* — Greenblum & Bernstein, P.L.C.

(57) ABSTRACT

A method of providing information includes acquiring allergy information related to a user from a first server, the allergy information including information indicating a level of an allergic reaction of the user to each ingredient, generating, based on the menu information and the allergy information, a personalized menu arranged for the user according to the allergy information, the menu information including information indicating one or more ingredients contained in each dish and an amount of each ingredient, and transmitting the personalized menu to the information terminal. In the generating of the personalized menu, when the level of the allergic reaction of an ingredient in the menu information is equal to or lager than a criterion value, the ingredient is determined as an allergy ingredient that causes allergy. The personalized menu includes one or more dishes, in each of which the allergy ingredient that causes allergy is reduced.

20 Claims, 37 Drawing Sheets

(58) Field of Classification Search
USPC .......................................................... 705/15
See application file for complete search history.

(56) References Cited

U.S. PATENT DOCUMENTS

| | | | | |
|---|---|---|---|---|
| 10,949,935 | B2* | 3/2021 | Nitzschke | ............... G07F 9/002 |
| 11,393,053 | B2 | 7/2022 | Yahata et al. | |
| 2005/0171800 | A1 | 8/2005 | Yamaguchi | |
| 2015/0036138 | A1 | 2/2015 | Watson | |
| 2015/0199776 | A1 | 7/2015 | Gluck | |
| 2016/0093005 | A1* | 3/2016 | Cornhill | ................. G06Q 50/12 705/15 |
| 2017/0109350 | A1 | 4/2017 | Nagano et al. | |
| 2017/0316352 | A1 | 11/2017 | Abujbara | |
| 2018/0144821 | A1 | 5/2018 | Irani-Cohen | |
| 2018/0268503 | A1 | 9/2018 | Parikh | |
| 2019/0311445 | A1 | 10/2019 | Werner | |
| 2020/0066181 | A1 | 2/2020 | Hadjigeorgiou | |
| 2020/0194125 | A1 | 6/2020 | Adolphus | |
| 2020/0311056 | A1 | 10/2020 | Robberechts | |
| 2020/0365250 | A1 | 11/2020 | Kim | |
| 2021/0097592 | A1 | 4/2021 | Yamamoto | |

FOREIGN PATENT DOCUMENTS

| | | | |
|---|---|---|---|
| CN | 110603598 | A | 12/2019 |
| JP | 2004-310205 | | 11/2004 |
| JP | 2005-018181 | A | 1/2005 |
| JP | 2005018181 | A * | 1/2005 |
| JP | 2006-079209 | | 3/2006 |
| JP | 2007-087319 | A | 4/2007 |
| JP | 2008-299821 | | 12/2008 |
| JP | 2013-149185 | | 8/2013 |
| JP | 2016-134002 | A | 7/2016 |
| JP | 2017-076351 | A | 4/2017 |
| KR | 101761741 | | 7/2017 |
| KR | 20200072444 | | 6/2020 |
| KR | 102221784 | | 3/2021 |

OTHER PUBLICATIONS

The MY Office Action dated Oct. 31, 2022 for the related MY Patent Application No. PI2022003946.

English Translation of Chinese Search Report dated Mar. 10, 2023 for the related Chinese Patent Application No. 202180006716.0.

T Fujita, H. Shimada and K. Sato, "Self-ordering system of restaurants for considering allergy information," 2014 IEEE 11th Consumer Communications and Networking Conference (CCNC), 2014, pp. 179-184, doi: 10.1109/CCNC.2014.6940502. (Year: 2014).

Wen, Han, and Junehee Kwon. "Food Allergy Information Sharing and Communication Strategies in Full-Service Restaurants in the U.S." Journal of foodservice business research 22.1 (2019): 50-65. Web. (Year: 2019) (Year: 2019).

Wen, Han. "Risk Communication When Serving Customers with Food Allergies in Restaurants in the United States." ProQuest Dissertations Publishing, 2015. Print. (Year: 2015) : 50-65. Web. (Year: 2015) (Year: 2015).

Jankovic, V V et al. "Managing Allergies in Food Service." IOP Conference Series. Earth and Environmental Science. vol. 333. Bristol: IOP Publishing, 2019. 12040-. Web. (Year: 2019) eb. (Year: 2019) (Year: 2019).

International Search Report of PCT application No. PCT/JP2020/001205 dated Apr. 14, 2020.

* cited by examiner

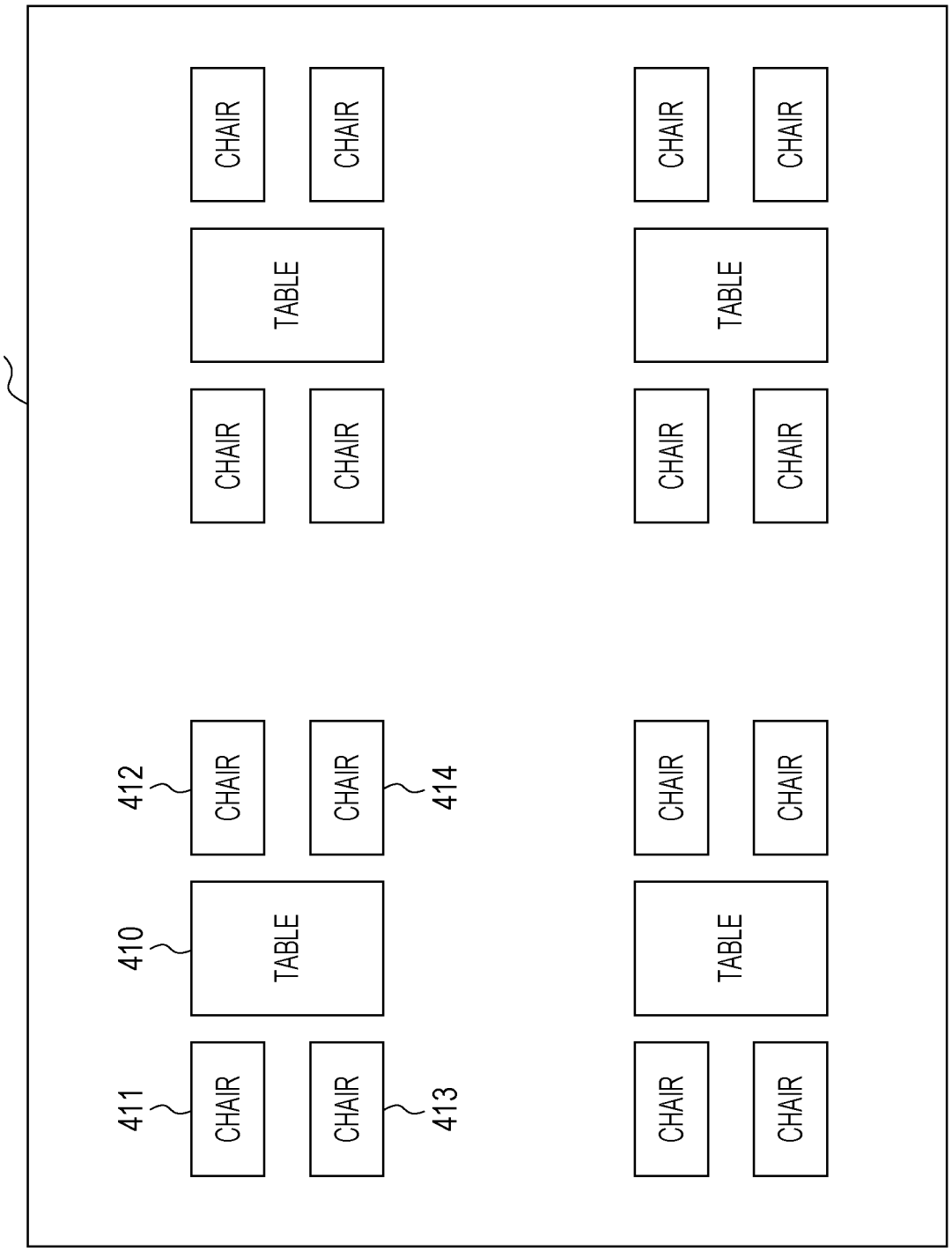

G108

2700

| FIELD | VALUE |
|---|---|
| INFORMATION CATEGORY | HEALTH CARE |
| ISSUER | ABC CLINIC |
| DATE OF ISSUE | DECEMBER 1, 2019 |
| DATA TYPE | ALLERGY TEST RESULT [IU/mL] |
| DATE OF TEST | NOVEMBER 14, 2019 |
| EGG | 25.40 |
| MILK | 0.66 |
| WHEAT | 0.60 |
| PEANUT | 0.01 |
| SHRIMP | 632.38 |
| CRAB | 538.42 |
| TUNA | 1.02 |
| ⋮ | ⋮ |

| FIELD | VALUE |
|---|---|
| DISH NAME | SPOT SHRIMP (2 PIECES) |
| SPOT SHRIMP | 20 g |
| RICE | 36 g |
| SUSHI VINEGAR | 1 g |

| FIELD | VALUE |
|---|---|
| DISH NAME | SOY SAUCE RAMEN |
| WHEAT FLOUR | 50 g |
| SALT | 5 g |
| POTATO STARCH | 1 g |
| SOY SAUCE | 10 g |
| OYSTER SAUCE | 1 g |
| SESAME | 0.5 g |
| WATER | 400 g |

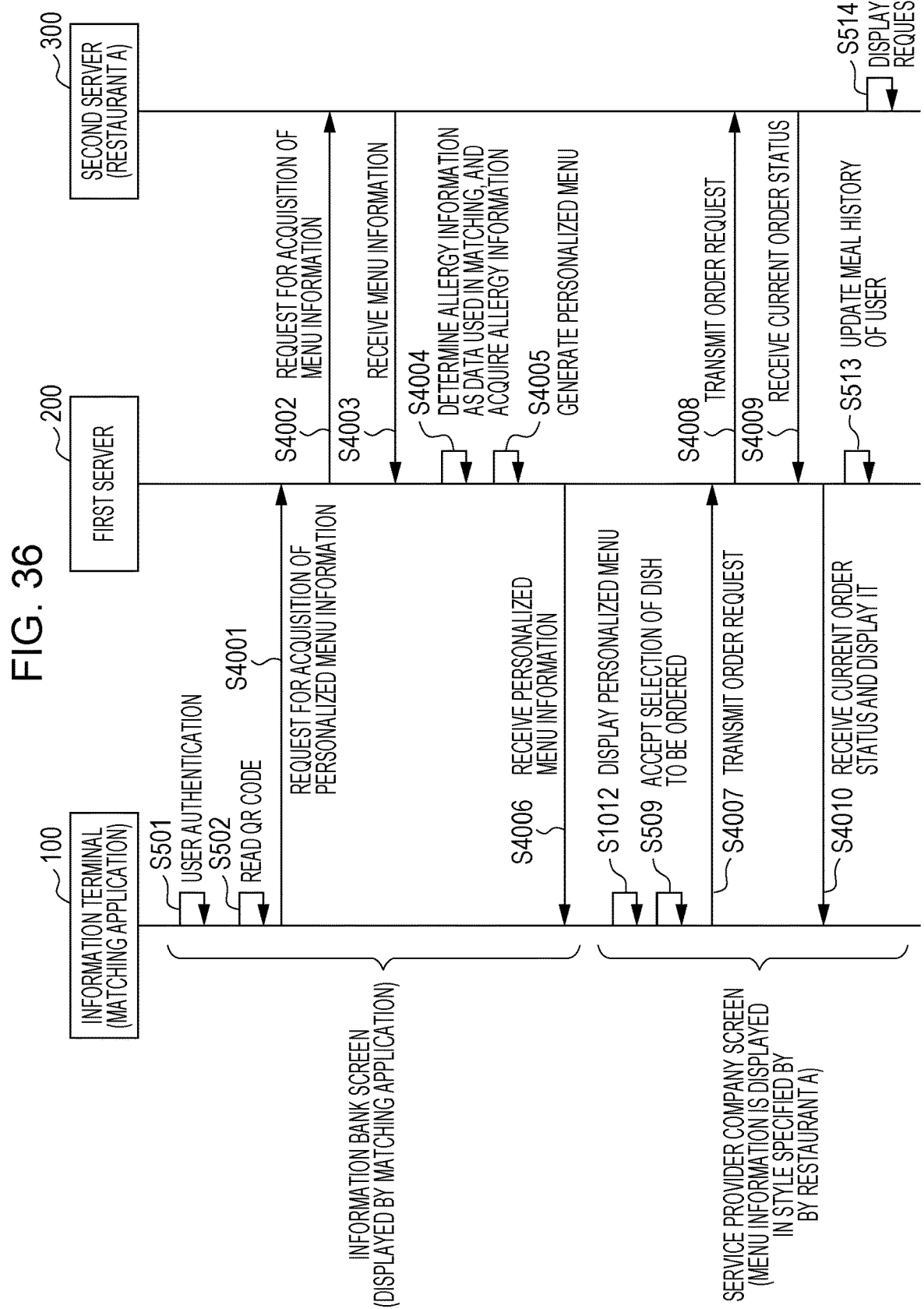

METHOD OF PROVIDING INFORMATION

BACKGROUND

1. Technical Field

The present disclosure relates to a method of providing information.

2. Description of the Related Art

Japanese Unexamined Patent Application Publication No. 2004-310205 (hereinafter, for simplicity, referred to as PTL 1) discloses a mobile terminal for a personal meal management system capable of determining a meal menu taking into account a content of a meal in the past, depending on a predetermined purpose. The mobile terminal for the personal meal management system disclosed in PTL 1 acquires menu information from outside via communication means, selects a meal menu based on the acquired menu information, a meal history stored in storage means, a user status, and an eating rule, and presents the selected meal menu as a recommended menu.

Japanese Unexamined Patent Application Publication No. 2008-299821 (hereinafter, for simplicity, referred to as PTL 2) discloses an order reception apparatus for use in a restaurant, which is installed in the restaurant for inputting menu order information and the like to support a customer service operation. The order reception apparatus for use in a restaurant disclosed in PTL 2 includes means for displaying an order input screen on a display device on which it is allowed to input menu order information. On the order input screen, menu order information is input individually for each seat set at a table.

SUMMARY

A further improvement is required in the related technique described above.

In one general aspect, the techniques disclosed here feature a method of providing information in an information management system that communicates with a first server which manages allergy information related to a user corresponding to identification information identifying the user, the information management system including a second server that stores menu information indicating one or more dishes corresponding to a restaurant, the method including acquiring a request for a personalized menu for the user from an information terminal of the user via a network, acquiring the identification information stored in the information terminal from the information terminal via the network, acquiring allergy information related to the user using the identification information from the first server via a network, the allergy information including information indicating a level of an allergic reaction of the user to each ingredient, generating, based on the menu information and the allergy information, a personalized menu arranged for the user according to the allergy information, the menu information including information indicating one or more ingredients contained in each dish and an amount of each ingredient, and transmitting the personalized menu to the information terminal to allow a selection of a dish to be selected via the personalized menu on the information terminal. In the generating of the personalized menu, when the level of the allergic reaction of an ingredient included in the menu information is equal to or larger than a criterion value, the ingredient is determined as an allergy ingredient that causes allergy, and the personalized menu includes one or more dishes, in each of which the allergy ingredient that causes allergy is reduced.

The aspect described above provides a further improvement.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a diagram showing an example of a layout of a store of a restaurant company;

FIG. 22 is a diagram showing an example of a data structure of ingredient information included in menu information returned from a second server;

FIG. 23 is a diagram showing another example of a data structure of ingredient information included in menu information returned from a second server;

FIG. 36 is a sequence diagram showing an example of a process performed in an information processing system according to a third embodiment.

DETAILED DESCRIPTION

Figure 1:
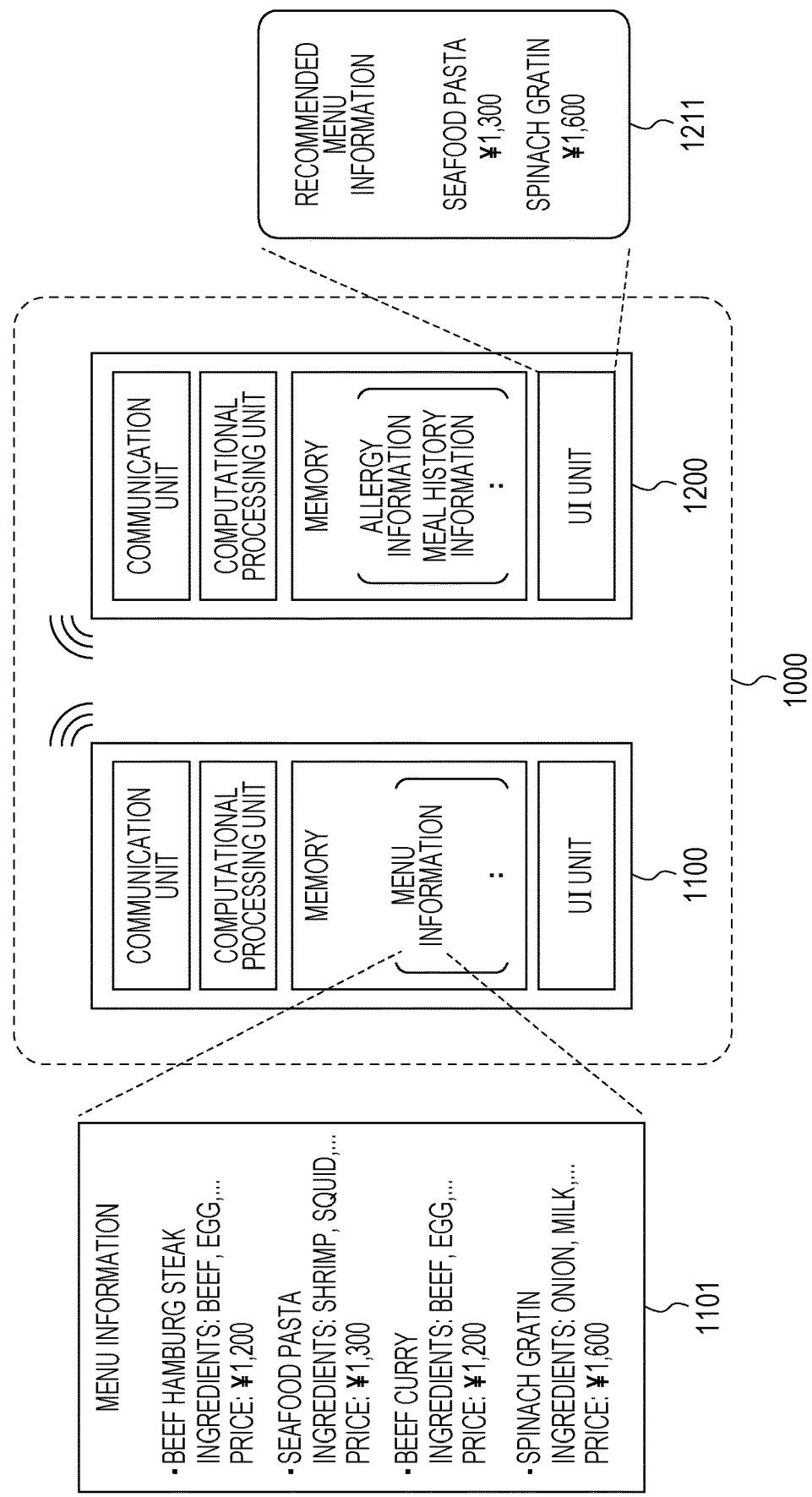
FIG. 1 is a diagram showing a configuration of a common food ordering system.

Underlying Knowledge Forming Basis of the Present Disclosure

In the technique disclosed in PTL 1 and the technique disclosed in PTL 2, when a dish with a suppressed allergen ingredient is provided, in a restaurant, to a customer who is allergic to this ingredient, considering is not sufficient as to a technique of providing a personalized menu taking into account a level of allergic reaction of the customer. Furthermore, no sufficient consideration is made on an information management system for providing service using personal information such as information on an allergic reaction level while protecting the personal information.

To solve at least one of the above problems, the present disclosure provides a control method as described below.

In an aspect, the present disclosure provides a method of providing information in an information management system that communicates with a first server which manages allergy information related to a user corresponding to identification information identifying the user, the information management system including a second server that stores menu information indicating one or more dishes corresponding to a restaurant, the method including acquiring a request for a personalized menu for the user from an information terminal of the user via a network, acquiring the identification information stored in the information terminal from the information terminal via the network, acquiring allergy information related to the user using the identification information from the first server via a network, the allergy information including information indicating a level of an allergic reaction of the user to each ingredient, generating, based on the menu information and the allergy information, a personalized menu arranged for the user according to the allergy information, the menu information including information indicating one or more ingredients contained in each dish and an amount of each ingredient, and transmitting the personalized menu to the information terminal to allow a dish to be selected via the personalized menu on the information terminal. In the generating of the personalized menu, when the level of the allergic reaction of an ingredient included in the menu information is equal to or larger than a criterion value, the ingredient is determined as an allergy ingredient that causes allergy, and the personalized menu includes one or more dishes, in each of which the allergy ingredient that causes allergy is reduced.

According to this aspect, an ingredient that causes an allergic reaction with a level equal to or larger than the criterion value is determined as an allergenic ingredient, and a personalized menu includes one or more dishes, in each of which the allergy ingredient that causes allergy is reduced. Therefore, it becomes possible to accurately identify ingredients that can cause an allergic reaction, remove or reduce such ingredients from a dish, and present the resultant dish to the user. This prevents a significant adverse effect on the user's health.

In the above-described method of providing information, when the request for the personalized menu for the user is acquired, a seat ID indicating a seat of the user may be acquired from the information terminal of the user, wherein the seat ID may be acquired via an operation screen displayed on a display of the information terminal.

According to this aspect, when the request for the personalized menu is acquired, the operation screen is displayed on the display of the user's information terminal, and the seat ID indicating the seat of the user is acquired via this operation screen.

Thus, in a series of processes in which the user orders a dish, the dish selected by the user from the personalized menu can be associated with the seat of the user. Note that the seat ID may be acquired by reading, via the operation screen, an identification code prepared at a corresponding position of a table where the user is seated, or may be acquired by the user manually inputting information corresponding to the seat ID according to an instruction displayed on the operation screen.

In the method of providing information, the reducing of the allergy ingredient may include removing the allergy ingredient such that an amount of the ingredient is zero.

In this aspect, the personalized menu includes a dish prepared so as not to include the allergy ingredient that causes allergy. This prevents a significant adverse effect on the user's health.

In another aspect, the present disclosure provides a method of providing information in an information management system that communicates with a first server which manages allergy information related to a user corresponding to identification information identifying the user, the information management system including a second server that stores menu information indicating one or more dishes corresponding to a restaurant, the method including acquiring a request for a personalized menu for the user from an information terminal of the user via a network, acquiring the identification information stored in the information terminal from the information terminal via the network, acquiring the allergy information related to the user from the first server via a network, the allergy information including information indicating a level of an allergic reaction of the user to each ingredient, generating, based on the menu information and the allergy information, a personalized menu arranged for the user according to the allergy information, the menu information including information indicating one or more ingredients contained in each dish and an amount of each ingredient, and transmitting the personalized menu to the information terminal to allow a selection of a dish via the personalized menu on the information terminal. In the generating of the personalized menu, when the level of the allergic reaction of an ingredient included in the menu information is equal to or larger than a criterion value, the ingredient is determined as an allergy ingredient that causes allergy, and the personalized menu is generated by excluding an allergy dish included in the menu information, the allergy dish including the allergy ingredient that causes allergy.

According to this aspect, an ingredient that causes an allergic reaction with a level equal to or larger than the criterion value is determined as an allergy-causing ingredient, and a personalized menu is generated so as to exclude a dish including the determined allergy-causing ingredient. Therefore, it becomes possible to accurately identify ingredients that can cause an allergic reaction, remove or reduce such ingredients from a dish, and present the resultant dish to the user.

In the above-described method of providing information, when the request for the personalized menu for the user is acquired, a seat ID indicating a seat of the user may be acquired from the information terminal of the user, wherein the seat ID may be acquired via an operation screen displayed on a display of the information terminal.

According to this aspect, when the request for the personalized menu is acquired, the operation screen is displayed on the display of the user's information terminal, and the seat ID indicating the seat of the user is acquired via this operation screen.

Thus, in a series of processes in which the user orders a dish, the dish selected by the user from the personalized menu can be associated with the seat of the user. Note that the seat ID may be acquired by reading, via the operation screen, an identification code prepared at a corresponding position of a table where the user is seated, or may be acquired by the user manually inputting information corresponding to the seat ID according to an instruction displayed on the operation screen.

In the method of providing information, the identification information may include a user ID.

In this aspect, the identification information includes the user ID, and thus it is possible to acquire the allergy information related to the user.

In the method of providing information, the first server may be different from the second server.

In this aspect, the first server is realized by a server different from the second server. Therefore, the second server does not need to perform a troublesome operation to manage the allergy information, which is sensitive information related to the user.

In the method of providing information, the seat ID may be acquired by reading, via the operation screen, an identification code prepared at a location corresponding to a seat of a table where the user is seated.

In this aspect, the seat ID is acquired by reading the identification code prepared at the location corresponding to the seat of the table where the user is seated. Thus, it is possible to automatically acquire the seat ID without having the user to manually input the information. Thus, in a series of processes in which the user orders a dish, the dish selected by the user from the personalized menu can be automatically associated with the seat of the user without needing a manual operation. Therefore, for example, even in a case where a plurality of users sit at the same table and each user orders a dish, it is possible to prevent an allergen-uncontrolled dish ordered by another user sitting at the same table from being carried to a seat of a user having food allergy. Thus, a user who is allergic to some ingredient can easily order a dish and can eat the ordered dish without worrying about a serious health problem.

In the method of providing information, the identification code may include a QR code.

In this aspect, since the identification code is given by a QR code, it is possible to acquire the identification information without having the user to manually input the information.

In the control method described above, the first server may distributedly manage at least one of biological information including the allergy information, preference information including user's item purchase history information or dish order history information, or behavior history information including location information of the user.

In this aspect, the first server includes servers that distributedly manage at least one of biological information including the allergy information, preference information including user's purchase history information or dish order history information, or behavior history information, and thus it is possible to acquire user's personal information including allergy information as necessary. Thus, this aspect makes it possible to maintain the freshness of the allergy information stored in the first server, thereby preventing the personalized menu from being generated based on old allergy information.

In another aspect, the present disclosure provides a method of providing information in an information management system that includes a first server and communicates with a second server, wherein a first server manages allergy information related to a user in association with identification information identifying the user, and the second server stores menu information indicating one or more dishes corresponding to a restaurant, the method including outputting to the second server a request for sending of the menu information to the first server, based on a request for a personalized menu for the user acquired from an information terminal of the user via a network, acquiring the identification information stored in the information terminal from the information terminal via the network, acquiring the menu information from the second server, generating, based on the menu information and the allergy information related to the user corresponding to the identification information, a personalized menu arranged for the user according to the allergy information, the menu information including information indicating one or more ingredients contained in each dish and an amount of each ingredient, and transmitting the personalized menu to the information terminal to allow a dish to be selected via the personalized menu on the information terminal. In the generating of the personalized menu, when the level of the allergic reaction of an ingredient included in the menu information is equal to or larger than a criterion value, the ingredient is determined as an allergy ingredient that causes allergy, and the personalized menu includes one or more dishes, in each of which the allergy ingredient that causes allergy is reduced.

According to this aspect, an ingredient that causes an allergic reaction with a level equal to or larger than the criterion value is determined as an allergy-causing ingredient, and the personalized menu includes one or more dishes, in each of which the allergy ingredient that causes allergy is reduced. Therefore, it becomes possible to accurately identify ingredients that can cause an allergic reaction, remove or reduce such ingredients from a dish, and present the resultant dish to the user. This prevents a significant adverse effect on the user's health. Furthermore, in the present aspect, since the allergy information is not transmitted to the second server, it is possible to prevent the allergy information from leaking to the restaurant.

In the above-described method of providing information, when the request for the personalized menu for the user is acquired, a seat ID indicating a seat of the user may be acquired from the information terminal of the user, wherein the seat ID may be acquired via an operation screen displayed on a display of the information terminal.

According to this aspect, when the request for the personalized menu is acquired, the operation screen is displayed on the display of the user's information terminal, and the seat ID indicating the seat of the user is acquired via this operation screen.

Thus, in a series of processes in which the user orders a dish, the dish selected by the user from the personalized menu can be associated with the seat of the user. Note that the seat ID may be acquired by reading, via the operation screen, an identification code prepared at a corresponding position of a table where the user is seated, or may be acquired by the user manually inputting information corresponding to the seat ID according to an instruction displayed on the operation screen.

In the method of providing information, the reducing of the allergy ingredient may include removing the allergy ingredient such that an amount of the ingredient is zero.

In this aspect, the personalized menu includes a dish prepared so as not to include the allergy ingredient that causes allergy. This prevents a significant adverse effect on the user's health.

In another aspect, the present disclosure provides a method of providing information in an information management system that includes a first server and communicates with a second server, wherein the first server manages allergy information related to a user corresponding to identification information identifying the user, and the second server stores menu information indicating one or more dishes corresponding to a restaurant, the method including outputting to the second server a request for sending of the menu information to the first server, based on a request for a personalized menu for the user acquired from an information terminal of the user via a network, acquiring the identification information stored in the information terminal from the information terminal via the network, acquiring the menu information from the second server, generating, based on the menu information and the allergy information related to the user corresponding to the identification information, a personalized menu arranged for the user according to the allergy information, the menu information including information indicating one or more ingredients contained in each dish and an amount of each ingredient, and transmitting the personalized menu to the information terminal to allow a selection of a dish to be selected via the personalized menu on the information terminal. In the generating of the personalized menu, when the level of the allergic reaction of an ingredient included in the menu information is equal to or larger than a criterion value, the ingredient is determined as an allergy ingredient that causes allergy, and the personalized menu is generated by excluding an allergy dish included in the menu information, the allergy dish including the allergy ingredient that causes allergy According to this aspect, an ingredient that causes an allergic reaction with a level equal to or larger than the criterion value is determined as an allergy-causing ingredient, and a personalized menu is generated so as to exclude a dish including the determined allergy-causing ingredient. Therefore, it becomes possible to accurately identify ingredients that can cause an allergic reaction, remove or reduce such ingredients from a dish, and present the resultant dish to the user. This prevents a significant adverse effect on the user's health. Furthermore, in the present aspect, since the allergy information is not transmitted to the second server, it is possible to prevent the allergy information from leaking to the restaurant.

In the above-described method of providing information, when the request for the personalized menu for the user is acquired, a seat ID indicating a seat of the user may be acquired from the information terminal of the user, wherein the seat ID may be acquired via an operation screen displayed on a display of the information terminal.

According to this aspect, when the request for the personalized menu is acquired, the operation screen is displayed on the display of the user's information terminal, and the seat ID indicating the seat of the user is acquired via this operation screen.

Thus, in a series of processes in which the user orders a dish, the dish selected by the user from the personalized menu can be associated with the seat of the user. Note that the seat ID may be acquired by reading, via the operation screen, an identification code prepared at a corresponding position of a table where the user is seated, or may be acquired by the user manually inputting information corresponding to the seat ID according to an instruction displayed on the operation screen.

In the method of providing information, the identification information may include a user ID.

In this aspect, the identification information includes the user ID, and thus it is possible to acquire the allergy information related to the user.

In the method of providing information, the first server may be different from the second server.

The first server stores sensitive information related to the user such as allergy information related to the user. It is not desirable that such sensitive information is provided outside the first server without the permission by the user. In this aspect, the first server is realized by a server different from the second server. Therefore, it is possible to prevent the user's sensitive information from leaking to the outside of the first server on the restaurant side.

In the method of providing information, the seat ID may be acquired by reading, via the operation screen, an identification code prepared at a location corresponding to a seat of a table where the user is seated.

In this aspect, the seat ID is acquired by reading the identification code prepared at the corresponding position of the table where the user is seated. Thus, it is possible to automatically acquire the seat ID without having the user to manually input the information. Thus, in a series of processes in which the user orders a dish, the dish selected by the user from the personalized menu can be automatically associated with the seat of the user without needing a manual operation. Therefore, for example, even in a case where a plurality of users sit at the same table and each user orders a dish, it is possible to prevent an allergen-uncontrolled dish ordered by another user sitting at the same table from being carried to a seat of a user having food allergy. Thus, a user who is allergic to some ingredient can easily order a dish and can eat the ordered dish without worrying about a serious health problem.

The identification code may include a QR code.

In this aspect, since the identification code is given by a QR code, it is possible to acquire the identification information without having the user to manually input the information.

The first server may distributedly manage at least one of biological information including the allergy information, preference information including user's item purchase history information or dish order history information, or behavior history information including location information of the user.

In this aspect, the first server includes servers that distributedly manage biological information including the allergy information, preference information including user's purchase history information or dish order history information, and behavior history information, and thus it is possible to acquire user's personal information including allergy information as necessary. Thus, this aspect makes it possible to maintain the freshness of the allergy information stored in the first server, thereby preventing the personalized menu from being generated based on old allergy information.

The present disclosure can also be implemented by a program for causing a computer to realize each feature of the method of providing information described above, or the present disclosure can be implemented on a server operated by such a program. Such a computer program may be distributed via a computer-readable non-transitory storage medium such as a CD-ROM or a communication network such as the Internet.

First Embodiment

It is expected that the Internet will continue to spread in our society and various sensors will be used in our lives. As a result, it is expected that in our future society, it will be capable of digitizing information on conditions and activities of individuals, as well as information on the entire city, including buildings and transportation networks, and it will become possible to use such digitized information in computer systems. Digitized personal data (personal information) is accumulated in the cloud via a communication network, managed by an information bank as big data, and used for various purposes for individuals.

Such an advanced information society is called Society 5.0 in Japan. The advanced information society is a society in which economic development and solutions to social issues are expected to be achieved via an information infrastructure (a cyber-physical system) in which a real space (a physical space) and a virtual space (a cyber space) are highly integrated.

In such an advanced information society, when an individual makes a decision in various daily situations, big data including accumulated personal information is analyzed to get to know what is the best choice for the individual in a specific situation.

Embodiments are described below in which an economic efficiency and personal optimization (personalization) are achieved in an advanced information society in which such cyber-physical systems operate. More specifically, the following embodiments are described taking as an example eating of individuals in such an advanced information society.

An example of a personally optimized dish order system is a system in which menu information is transmitted from a terminal at a store of a restaurant to a personal information terminal, and a menu indicating dishes including no ingredient to which a user is allergic is displayed as a recommended menu on the mobile terminal. First, a general dish order system is described which is expected to be built in a society before the above-described advanced information society is realized.

FIG. 1 is a diagram showing a configuration of a common dish ordering system. This dish ordering system includes a store terminal 1100 and a mobile terminal 1200. The store terminal 1100 and the mobile terminal 1200 are installed in a store of a restaurant 1000. The store terminal 1100 is a computer that transmits menu information. The store terminal 1100 includes a communication unit for communicating with an external apparatus, a computational processing unit for performing a computational process, a memory for storing data, and a UI unit for displaying and operating information. The memory stores menu information 1101. The menu information 1101 includes information on dishes served at the restaurant. More specifically, the menu information 1101 includes a name of a dish, ingredients used in the dish, and a price of the dish. In the example shown in FIG. 1, the menu information 1101 includes four dishes: beef hamburger; seafood pasta; beef curry; and spinach gratin.

The mobile terminal 1200 is a mobile terminal such as a smartphone owned by a user who visits the store 1000. The mobile terminal 1200 includes a communication unit for communicating with an external apparatus, a computational processing unit for performing a computational process, a memory for storing data, and a UI unit for displaying and operating information. The memory stores allergy information, meal history information, and the like of a user who owns the mobile terminal 1200.

When the user enters the store 1000, the store terminal 1100 and the mobile terminal 1200 start communication automatically or manually. When the communication is started, the mobile terminal 1200 acquires menu information 1101 from the store terminal 1100. When the mobile terminal 1200 acquires the menu information 1101, the mobile terminal 1200 checks the menu information and the allergy information stored in the memory, and extracts dishes that do not include ingredients to which the user is allergic. The mobile terminal 1200 generates a recommended menu 1211 based on the extracted dishes, and displays the generated recommended menu 1211 on the UI unit. In the example shown in FIG. 1, the user is allergic to beef, and thus seafood pasta and spinach gratin are selected as beef-free dishes and displayed in the recommended menu 1211.

According to the above-described technique, the user is allowed to select an allergen-free dish from the displayed recommended menu.

In Society 5.0, personal information such as allergy information is centrally managed by a server operated by a company or an institution called an information bank that manages personal information in a concealed manner such that a third party is not capable of knowing which individual is related to the personal information. This personal information is updated as required under the control of the information bank without needing a manual inputting operation by a user at a terminal.

However, in the order system shown in FIG. 1, allergy information is managed by the mobile terminal 1200, but it is not managed by the server. Therefore, in the order system shown in FIG. 1, it is not easy to update allergy information. For example, to update the allergy information, the user needs to manually input the allergy information to the mobile terminal 1200, which is troublesome for the user. Furthermore, since the allergy information is not concealed, there is a risk that the allergy information may be leaked to the store terminal 1100. Therefore, a further improvement is needed to adapt the order system shown in FIG. 1 to the advanced information society advocated by Society 5.0. Thus, the present embodiment provides an information processing system based on Society 5.0. The information processing system according to the embodiment of the present disclosure is described below with reference to drawings.

Figure 2:
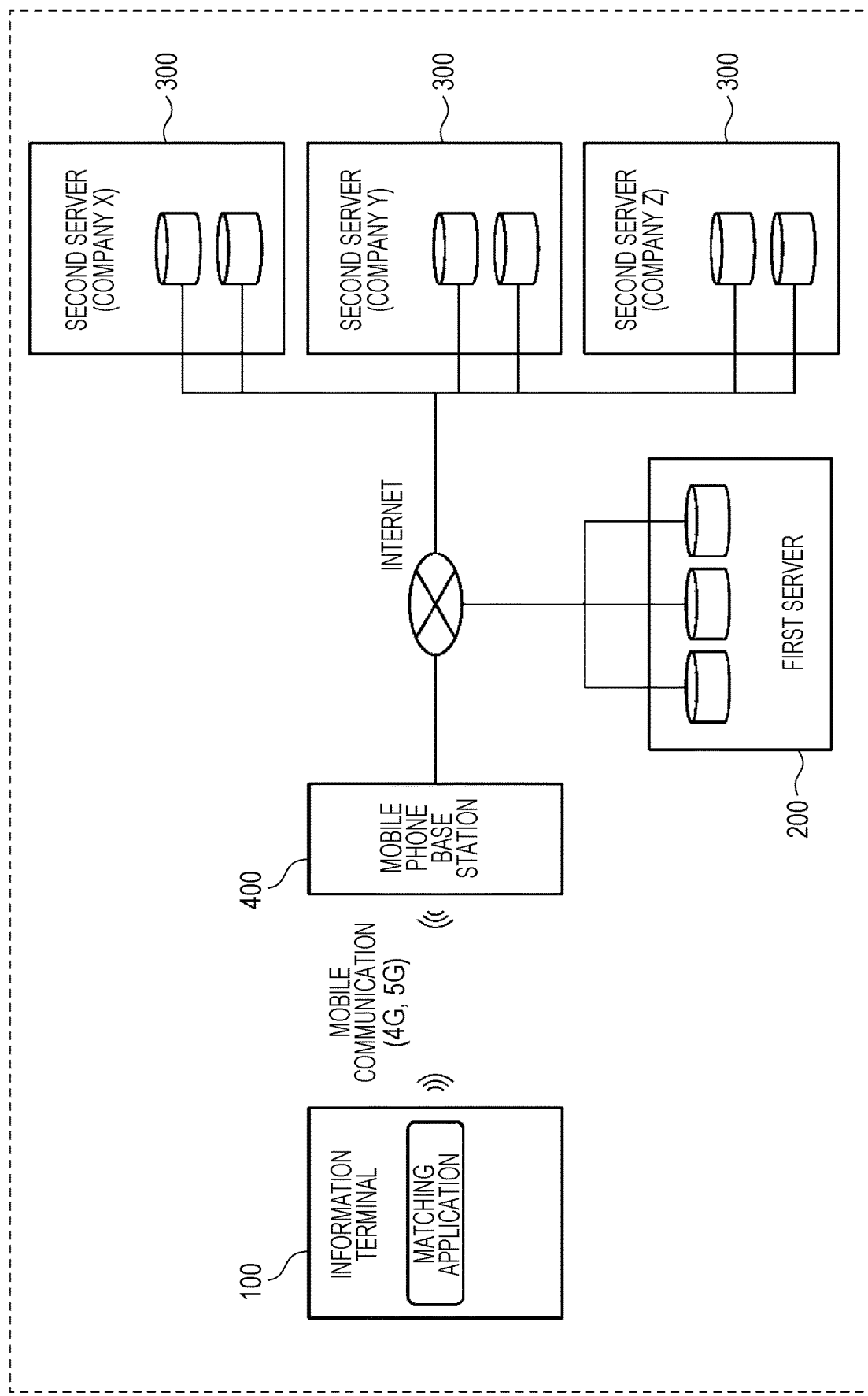
FIG. 2 is a diagram showing an example of an overall view of an information infrastructure of an information processing system according to an embodiment.

FIG. 2 is a diagram showing an example of an overall view of an information infrastructure of the information processing system according to the present embodiment. The information processing system shown in FIG. 2 is a system usable in Society 5.0, in which products or services suitable for a general consumer user are proposed based on personal information thereby providing a service of supporting the user to select a product or service. Before describing this selection support service that supports ordering of a dish according to the embodiment, an overview of an information infrastructure for realizing this embodiment is described with reference to FIG. 2. This information processing system mainly includes three apparatus groups.

A first apparatus group includes an information terminal 100 such as a smartphone owned by a user. A matching application is installed in the information terminal 100. The matching application is an application for selecting or recommending a product or service suitable for a user based on the user's personal information. The personal information used in the present disclosure broadly refers to public or non-public information about an individual. For example, the personal information includes at least one of the following: a name, a date of birth, an address, an annual income, an owned movable property/real estate information, physical information as to height/weight or the like, genetic information, allergy information, medical information as to a medical history/medical record or the like, activity amount information as to the number of steps/calories burned, meal history information, vital sign information as to heartbeat/blood pressure or the like, purchase information via stores/EC sites or the like, word information as to words used in searching via Web search engine/AI speaker, information as text/video/audio transmitted or received via mail/SNS, and movement history information, or the like. The information terminal 100 is capable of connecting to the Internet, for example, via a mobile communication network called 4G or 5G and via a mobile phone base station 400.

The second apparatus group includes a first server 200. The first server 200 is a personal information server that stores personal information related to a user such that the personal information is decrypted and distributed at a plurality of locations. For example, the first server 200 manages personal information such that the personal information related to the user is fragmented, encrypted, and stored in a plurality of storage apparatuses located on the cloud. This ensures that high security is achieved and leakage of the personal information is prevented. Furthermore, the first server 200 has a function of returning necessary data in response to an inquiry from a third party with the permission of the user. Furthermore, the first server 200 has a function of securely sharing the personal information permitted by a user with a company permitted by the user. That is, the first server 200 has a function as an information bank. In this case, for example, the first server 200 stores each one piece of data in a plurality of storage apparatuses in a distributed manner. An example of one piece of data is one file in which personal information is described.

In the present embodiment, the first server 200 allows a specific company to share specific personal information based on the permission of the user. Furthermore, the first server 200 has a function for providing a selection support service described below.

The above-described matching application is developed and/or provided by, for example, an operating company of the first server 200. This operating company evaluates the degree of suitability of the products or services that the user may use based on the personal information of the user. The operating company of the first server 200, the developing company of the matching application, and the company that distributes the matching application may be the same or different. The information processing system shown in FIG. 2 provides a selection support service using the matching application described above. Note that this is merely an example, and the information processing system may be configured in various different manners. For example, the selection support service may be realized by using an application other than the matching application or a general browser or the like. To securely handle the personal information related to the user, it is preferable to provide the selection support service by a dedicated application such as the matching application. However, when personal information with low security requirement such as publicly available personal information is handled, or when a function for ensuring security is provided, means other than the matching application may used in the selection support services.

The matching application handles personal information only inside the information terminal 100. For example, the matching application presents a user with a product or service that seems to be most suitable for the user under a given arbitrary condition in terms of time, a place, a situation, and/or the like. For example, the matching application provides an intermediary/mediation function in economic activities such as purchasing by a user.

The matching application is an application that opens the recommendation function to the public, which has been siloed for each service provider. This is described further below taking as an example a certain service provider which is famous in an electronic commerce market such as an electronic commerce (EC) site. Many products are listed on a site of the service provider. When a particular product is searched for or purchased, other products highly relevant to that product (for example, products that are often purchased together) are recommended to the user. The recommendation function for such purchases is effective only in the EC site of the service provider. Therefore, the recommendation function has no effect when products are purchased, meals are ordered at a restaurant, or planning a family vacation trip etc., via an EC site operated by another service provider.

It is expected that, in the future, personal information will be aggregated in information banks, and a mechanism will be established which makes it possible for anyone to access a huge variety of accurate personal information accumulated over a long period of time under predetermined conditions. In such a situation, the degree of suitability can be estimated not only for products provided by a service provider but also for all products or services based on a search or purchase history on the EC site of one service provider and based on the personal information of various users. This makes it possible to recommend products or services that are more valuable to the user from among various options.

According to the present embodiment, the first server 200 is assumed to be a general-purpose storage apparatus provided on a cloud that manages personal information in a distributed and encrypted manner so as to realize the above idea or function.

The third apparatus group is a group including a second server 300 by which each company manages data specific to the company. In the example shown in FIG. 2, three companies, that is, company X, company Y, and company Z each own a second server 300, and manage and/or provide information about their products and/or their services. Note that companies are not limited to restaurant companies which are described by way of example in detail in the present disclosure. For example, the company may be a ready-made meal company such as a lunch box shop or a fast food shop that provides takeaway food which has been cooked. The company may be a company which focuses on food to be cooked at home, such as a supermarket. Furthermore, the company may be even an automobile manufacturer, a real estate company, a hospital, a school, a cram school for studying or sports, a law firm, or a company that provides products and/or services to general consumers.

One of effects of the information processing system according to the present embodiment is that personal information is not given to the company without permission of a user. It is assumed that information banks allow specific companies to share personal information based on permission of users.

However, it is very troublesome to let users make judgment individually. Even if there is a trust company that sets a data operation policy, users may not be able to grasp exactly which data was passed to whom, which may cause the users to feel uneasy.

In view of the above, in this embodiment, it is prohibited for the company operating the first server 200 to use the stored personal information, for example, by decrypting and interpreting the personal information, unless the user permits.

Furthermore, in a case where there is an information bank or information intermediary that is operating in a market such that it manages personal information and provides a matching application under a strict privacy protection policy, a user may make a contract for receiving the service from this information bank or information intermediary. This makes it possible to prevent personal information from being given to other companies.

The present embodiment provides an information processing system for use in a next-generation information society in which a huge amount of personal information that changes from moment to moment can be used for matching with various services. The information processing system described below is assumed to be used in such a situation.

Figure 3:
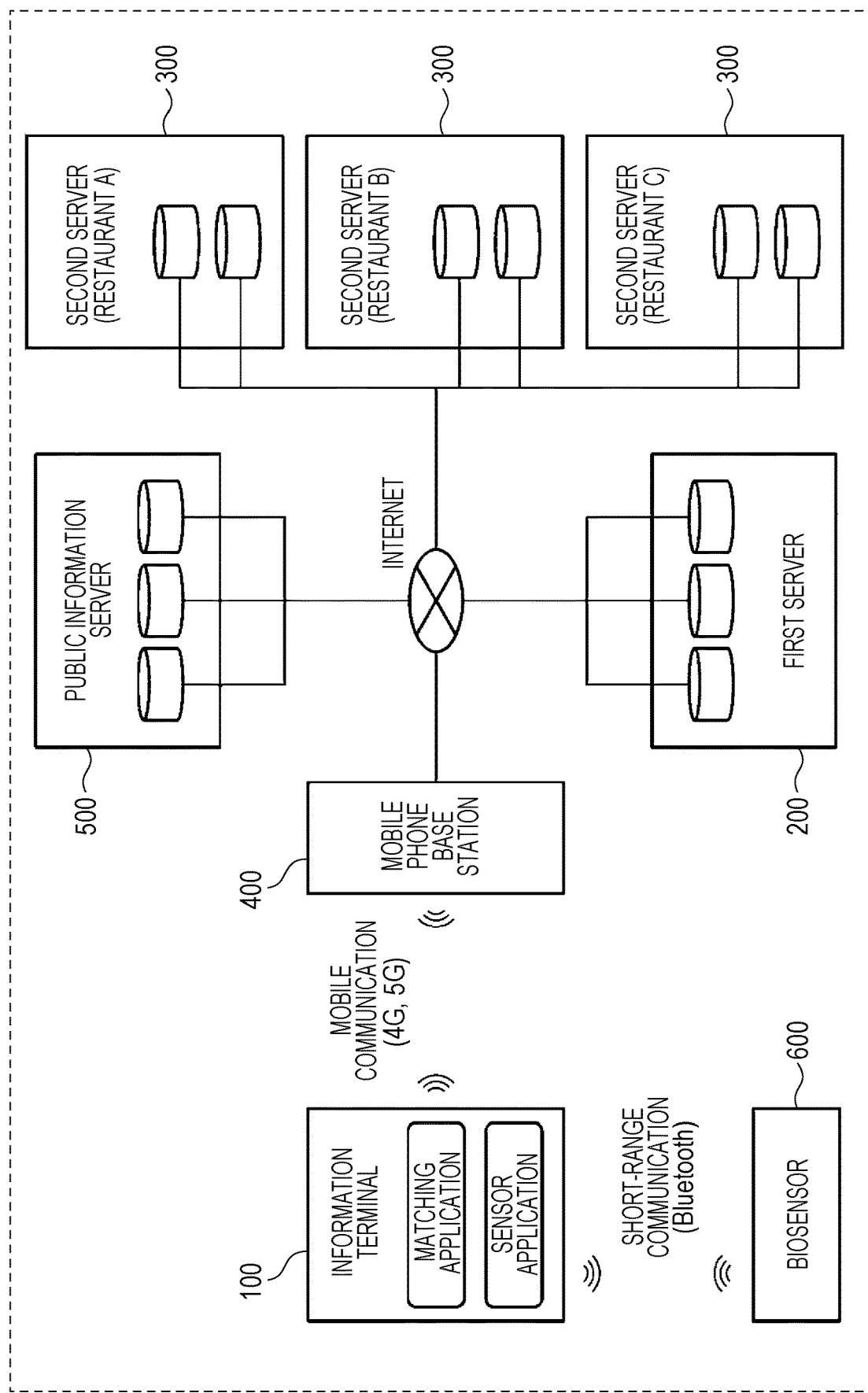
FIG. 3 is a diagram showing, in further detail, the overall view of the information processing system according to the present embodiment.

FIG. 3 is a diagram illustrating further details of the overall view of the information processing system according to the present embodiment. The information processing system shown in FIG. 3 is configured to provide menu information, in a restaurant or the like, for being seen by a user to order a dish such that the menu information is matched with the personal information related to the user and a menu optimized for the user is presented. The information processing system shown in FIG. 3 further includes a biosensor 600 and a public information server 500 in addition to constituent elements of the information processing system shown in FIG. 2.

In this example, the service providing companies include a restaurant company A, a restaurant company B, and a restaurant company C, which are companies in the restaurant industry. Restaurant companies A, B, and C are separate independent companies. The information processing system shown in FIG. 3 includes a second server 300 operated by the restaurant company A, a second server 300 operated by the restaurant company B, and a second server 300 operated by the restaurant company C. Menu information provided by each restaurant and information about each store are managed by corresponding one of these second servers 300. The second servers 300 are each realized, for example, by a cloud server.

The public information server 500 manages public information different from the restaurant information and different from the personal information. The public information server 500 is connected to the Internet. For example, the public information includes weather information, traffic information, and the like. These pieces of information are used as necessary for matching.

The biosensor 600 is a biosensor such as a smart watch. The biosensor 600 is worn by a user who owns the information terminal 100. The biosensor 600 continuously measures the user's vital sign information. Various kinds of vital sign information measured by the biosensor 600 are transmitted from the biosensor 600 to the information terminal 100 via short-range communication such as Bluetooth (registered trademark) communication. The vital sign information is stored and/or managed by a sensor application installed on the information terminal 100. The sensor application uploads the collected vital sign information and time information indicating the measurement time of the vital sign information to the first server 200 according to the user account information. As a result, the vital sign information is accumulated.

The sensor application may grant an access right to data stored and/or managed by the sensor application to the matching application or an OS (Operating System) of the information terminal 100. In this case, the vital sign information is uploaded to the first server 200 via the matching application or the OS. The sensor application may store the vital sign information in a memory of the information terminal 100, or may upload it to the first server 200 thereby storing it therein.

Figure 4:
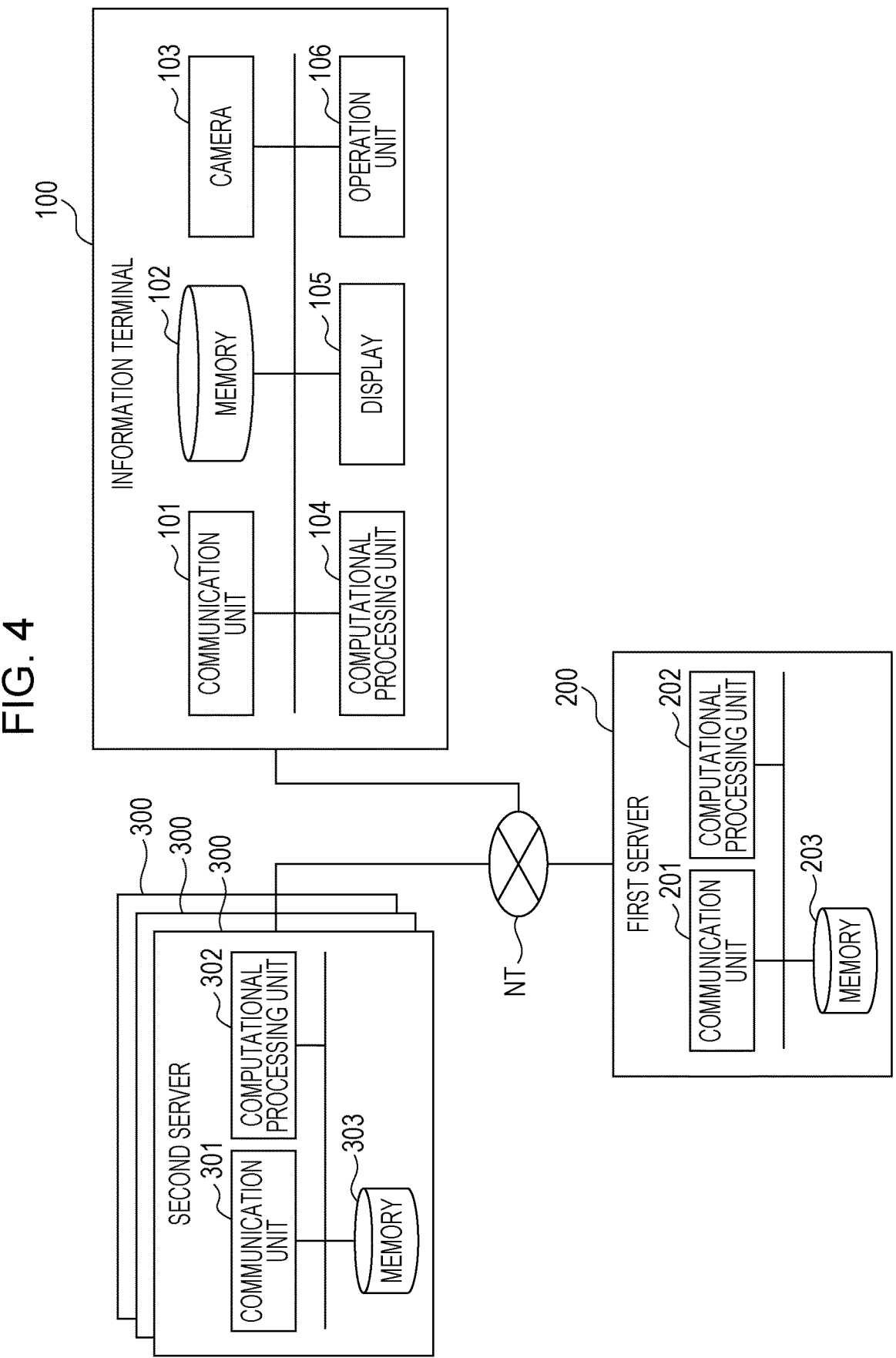
FIG. 4 is a diagram showing an example of a specific configuration of an information processing system according to an embodiment.

FIG. 4 is a diagram showing a specific example of a configuration of the information processing system according to the present embodiment. The information processing system shown in FIG. 4 includes the information terminal 100, the first server 200, and the second server 300 described above with reference to FIGS. 2 and 3. In FIG. 4, for convenience of explanation, the mobile phone base station 400 and the biosensor 600 are not shown. The information terminal 100, the first server 200, and the second server 300 are connected to each other so as to be capable of communicating with each other via the network NT. The network NT is a wide area communication network including a mobile phone communication network and the Internet.

The information terminal 100 is realized by a mobile information processing apparatus such as a smartphone, a tablet terminal, or the like. In the present embodiment, the information terminal 100 is carried by a user who orders a dish at a store of a restaurant. The information terminal 100 includes a communication unit 101, a memory 102, a camera 103, a computational processing unit 104, a display 105, and an operation unit 106.

The communication unit 101 includes a communication circuit that connects the information terminal 100 to the network NT. The communication unit 101 receives menu information (described later) transmitted from the second server 300, and stores it in the memory 102. The computational processing unit 104 reads the menu information stored in the memory 102 and performs processing. Furthermore, the communication unit 101 receives allergy information (described later) from the first server 200 and stores it in the memory 102. The computational processing unit 104 reads out allergy information stored in the memory 102 and performs processing. As a result, the computational processing unit 104 acquires allergy information and menu information. Furthermore, under the control of the computational processing unit 104, the communication unit 101 transmits ordered-dish information (described later) and a seat ID (described later) in association with each other to the second server 300.

The memory 102 is realized using a nonvolatile storage apparatus such as a flash memory or the like. The memory 102 stores information 2700 including allergy information shown by way of example in FIG. 21, and ingredient information 2800 shown by way of example in FIGS. 22 and 23. The ingredient information 2800 is information about ingredients used in a dish, and one piece of ingredient information 2800 corresponds to one dish. The menu information includes one or more pieces of ingredient information 2800. Details of the information 2700 and the ingredient information 2800 will be described later. The memory 102 also stores identification information identifying a user. The identification information includes a user ID (Identifier). The user ID is an identifier of a user.

The camera 103 is an image capturing apparatus including a CMOS sensor and/or the like. The camera 103 is used to capture a QR code attached to a seat in a store of a restaurant.

The computational processing unit 104 is realized using a processor such as a CPU. The computational processing unit 104 executes, on the information terminal 100, the OS, the above-described matching application, the QR code reader, the browser, and the like.

Figure 15:
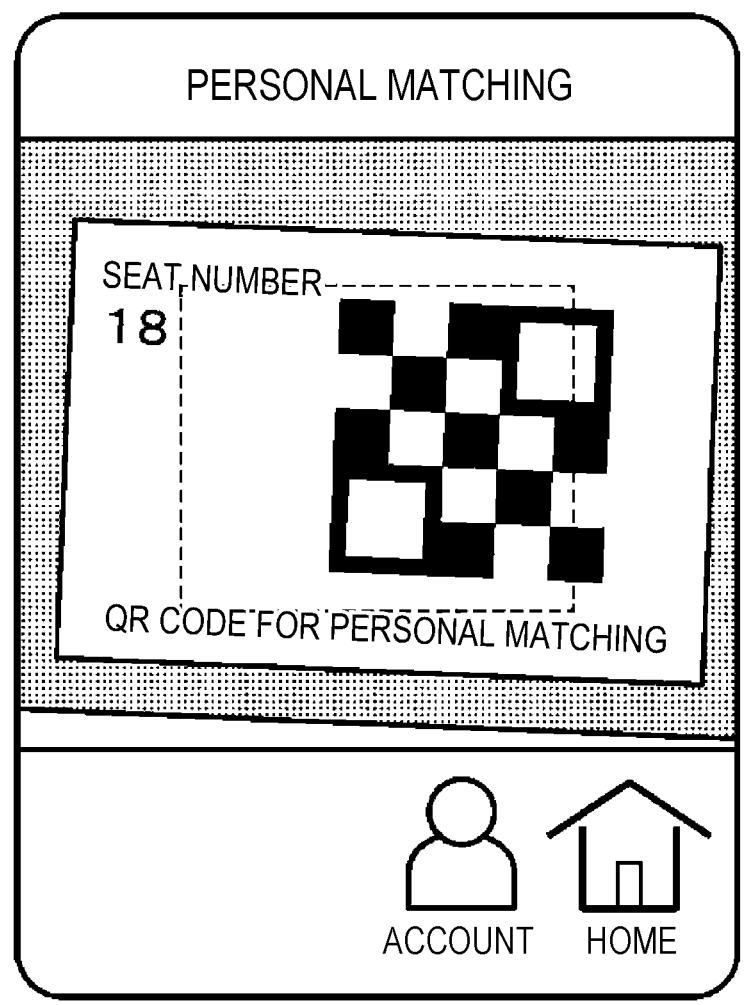
FIG. 15 is a diagram showing an example of an operation screen which is displayed on an information terminal when a user operates the information terminal to read a QR code at his/her seat after starting a matching application.

The computational processing unit 104 acquires a restaurant ID and a seat ID indicating a seat via a first operation screen displayed on the display 105. As shown in FIG. 15, the first operation screen is an operation screen for use in reading the QR code provided by the matching application. The restaurant ID is an identifier of a restaurant. When a restaurant has a plurality of stores, the restaurant ID may include a restaurant identifier and a store identifier. The seat ID is an identifier of a seat in a store. The computational processing unit 104 acquires the restaurant ID and the seat ID by analyzing the QR code which is captured by the camera 103 in response to a shoot command issued by a user via the operation unit 106.

The computational processing unit 104 acquires, via the network NT, menu information indicating one or more dishes available at the restaurant from the second server 300 of the restaurant corresponding to the restaurant ID, and stores the menu information in the memory 102. For example, in a case where the restaurant ID includes the identifier of the restaurant company A, the menu information is acquired from the second server 300 of the restaurant company A.

The computational processing unit 104 transmits the identification information stored in the memory 102 to the first server 200, acquires the allergy information related to the user from the first server 200 based on the identification information, and stores the acquired allergy information in the memory 102.

The computational processing unit 104 generates, based on the acquired menu information and the acquired allergy information, a personalized menu for the user, which is properly arranged in terms of allergens according to the allergy information. The personalized menu includes a list of dishes that are to be prepared so as to reduce ingredients that cause allergies indicated by the allergy information in each dish included in the menu information acquired by the computational processing unit 104. Note that the reducing of an ingredient may include removing the ingredient such that the dish does not include this ingredient at all. Note that the personalized menu may be generated by removing, from the list of dishes indicated in the menu information, any dishes including allergic ingredients indicated by the allergy information. Note that the personalized menu may be generated by removing, from the list of dishes indicated in the menu information, any dishes including allergic ingredients indicated by the allergy information.

Figure 18:
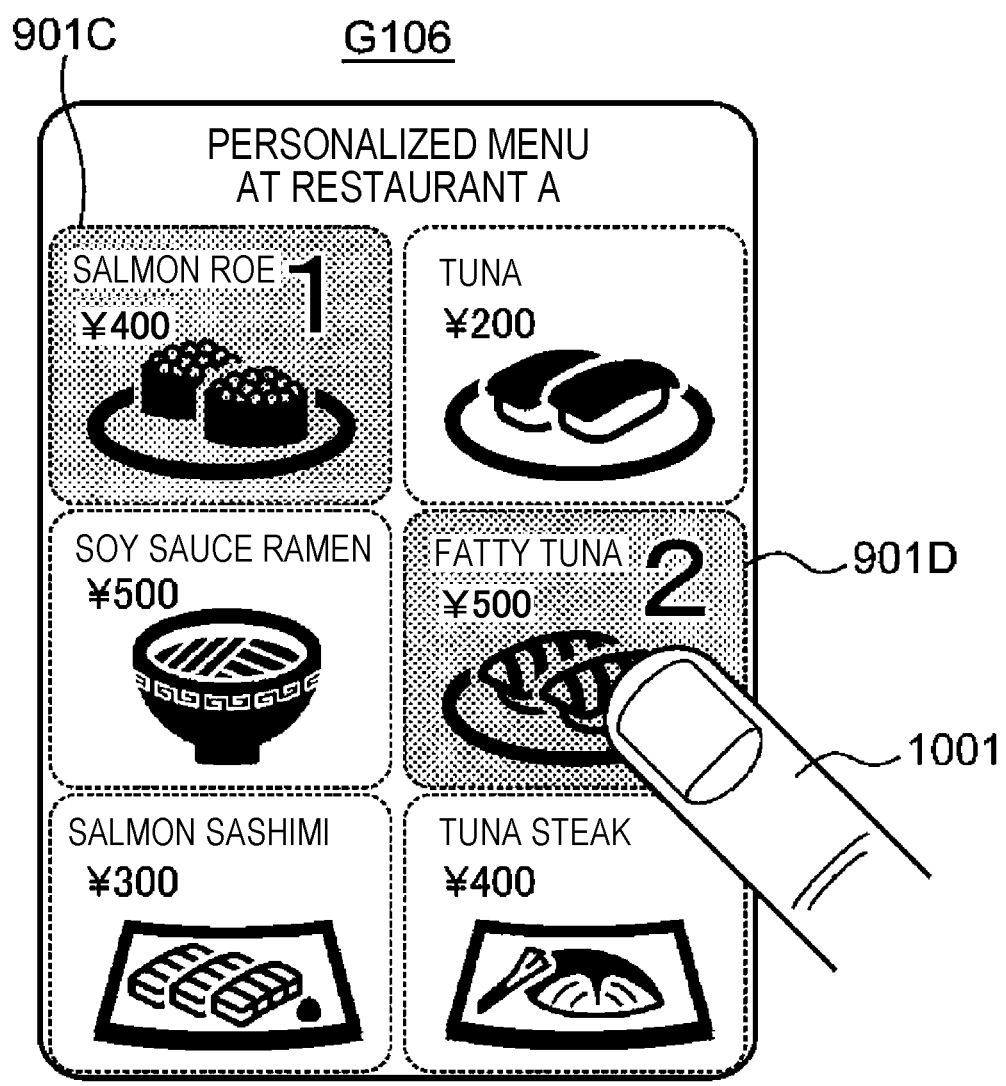
FIG. 18 is a diagram showing a scene in which a user operates an operation screen to select a dish from a personalized menu and order the selected dish.

The computational processing unit 104 displays the personalized menu via the second operation screen displayed on the display 105. As shown in FIG. 18, the second operation screen is for the restaurant to accept a dish order from a user. The second operation screen is provided via the matching application based on a design specified by the restaurant. The user performs an input operation to select a desired dish from the personalized menu displayed on the second operation screen thereby ordering the dish.

The computational processing unit 104 transmits ordered-dish information indicating the dish selected from the personalized menu and the seat ID in association with each other to the second server 300 via the communication unit 101. The ordered-dish information and the seat ID transmitted to the second server 300 are displayed on the display installed in the store of the restaurant corresponding to the second server 300 which is the transmission destination. An employee of this store cooks the food ordered by the user according to the displayed contents and carry the cooked food to the user's seat. Thus, the user can get and eat the ordered dish.

The display 105 is realized, for example, by a liquid crystal display panel or an organic EL panel, and is used to display various images. For example, the display 105 displays the above-described first operation screen and second operation screen.

The operation unit 106 is realized using an input device such as a touch panel. The operation unit 106 receives an instruction issued by a user to select a desired dish from the personalized menu.

The configuration of the information terminal 100 has been described above.

Next, a configuration of the first server 200 is described below. The first server 200 includes a communication unit 201, a computational processing unit 202, and a memory 203. The communication unit 201 includes a communication circuit for connecting the first server 200 to the network NT. The communication unit 201 transmits allergy information to the information terminal 100 in response to a request from the information terminal 100. The computational processing unit 202 is realized by a processor such as a CPU. The computational processing unit 202 processes personal information related to a user stored in the memory 203.

For example, let it be assumed here that the computational processing unit 202 receives, from the communication unit 201, a request signal for requesting acquisition of personal information about a permissive user. The permissive user refers to a user who has granted permission to read the personal information stored in the first server 200 in response to a request from the information terminal 100 or the second server 300 wherein the permission may be granted directly by the user or indirectly via a trusted third party. In this case, in response to the request from the information terminal 100 or the second server 300, the computational processing unit 202 reads out the personal information on the permissive user stored in the memory 203 and returns it via the communication unit 201. The personal information read in this situation may be the entire managed personal information, or only part of the entire information on a requested specific item (part of the personal information).

The memory 203 includes a plurality of nonvolatile storage apparatuses such as hard disk drives. The memory 203 stores personal information related to one or more users. The personal information includes allergy information related to each user. The personal information is stored such that it is encrypted and distributed over the plurality of storage apparatuses. The personal information stored in the memory 203 may include biological information, purchase history information, preference information, and behavior history information. The biological information is information representing a biological condition in terms of a heart rate and/or the like of each user. The biological information includes the above-described allergy information. The purchase history information is information indicating the purchase history of products (goods) or services of each user. The preference information is information indicating the preference of each user. The preference information includes order history information indicating a history of ordering of dishes made by each user. The behavior history information is information indicating a history of an action of each user. The behavior history information includes, for example, time-series data in association with the user's position information and time information.

Next, a configuration of the second server 300 is described below. There is one or more second servers 300 corresponding to respective restaurant companies. The second server 300 includes a communication unit 301, a computational processing unit 302, and a memory 303. The communication unit 301 includes a communication circuit for connecting the second server 300 to the network NT. The communication unit 301 transmits menu information to the information terminal 100 in response to a request from the information terminal 100. The computational processing unit 302 is realized using a processor such as a CPU. The computational processing unit 302 processes the menu information stored in the memory 303. The memory 303 is realized using a nonvolatile storage apparatus such as a hard disk drive. The memory 303 stores menu information.

FIG. 5 is a diagram showing a layout of a store of a restaurant company. In the example in FIG. 5, a layout of a store 40 of the restaurant company A is shown. Four tables 410 are installed in the store 40. Four chairs 411, 412, 413, and 414 are installed at each table 410.

When two or more users are seated at one table 410, there is a possibility that some of these users have food allergies. In this case, it must be avoided that the food ordered by each user is mistakenly served to another user. This is because food allergies are at risk of causing life-threatening and serious symptoms such as anaphylactic shock.

In order to avoid such mistakes, it is necessary to have an appropriate mechanism for associating the user with the dish ordered by the user. However, there are currently limited solutions to avoid such mistakes. In particular, no solution is known that can be applied to general restaurant stores such as those shown in FIG. 3. Currently, in a small store where a counter numbered for each seat is installed, there is an attempt of manually associating a user with a dish ordered by the user by using an order slip or using an order input terminal. However, the manual associating operation can cause a dish to be served to a wrong user.

The present embodiment provides a mechanism for more reliably associating and managing a user and a dish ordered by the user. A specific example for realizing this mechanism is described below. In the present embodiment, a QR code is set at each seat in the store 40. FIGS. 6A, 6B, 6C, and 6D each show an example of a manner of setting the QR code 601 on a seat. In the example shown in FIG. 6A, the QR code 601 is set on an upper surface of a backrest of each chair in the store. As described above, the QR code 601 includes the restaurant ID and the seat ID of the seat on which the QR code 601 is set. In this example, the QR code is used, but this is merely an example. Alternatively, any other information such as a bar code may be used as long as the restaurant ID and the seat ID can be identified.

Figure 6A:
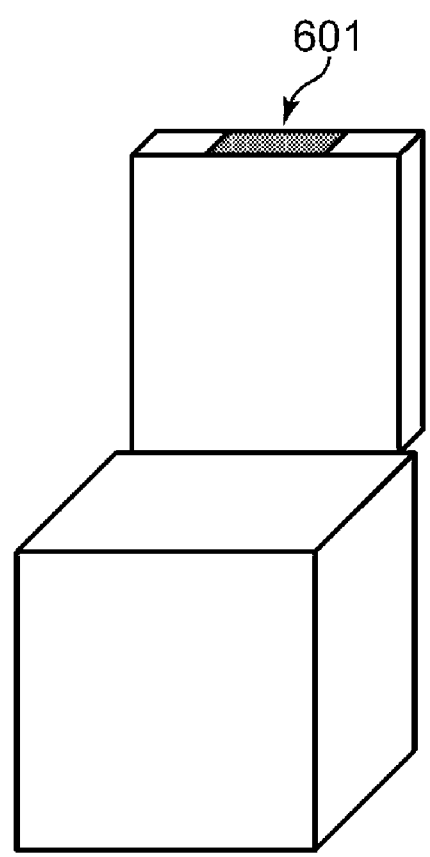
FIG. 6A is a diagram showing an example of a manner in which a QR code (registered trademark, the same hereinafter) is set on a seat.
Figure 6B:
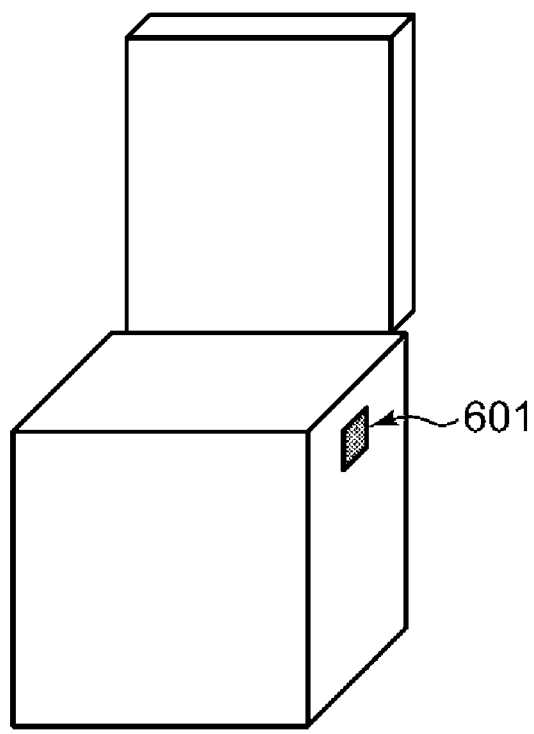
FIG. 6B is a diagram showing an example of a manner in which a QR code is set on a seat.

In the example in FIG. 6B, the QR code 601 is set on a side surface of a seat of each chair. By setting the QR code 601 on the side surface of the seat, it becomes possible for the user to easily perform an operation to read the QR code 601.

Figure 6C:
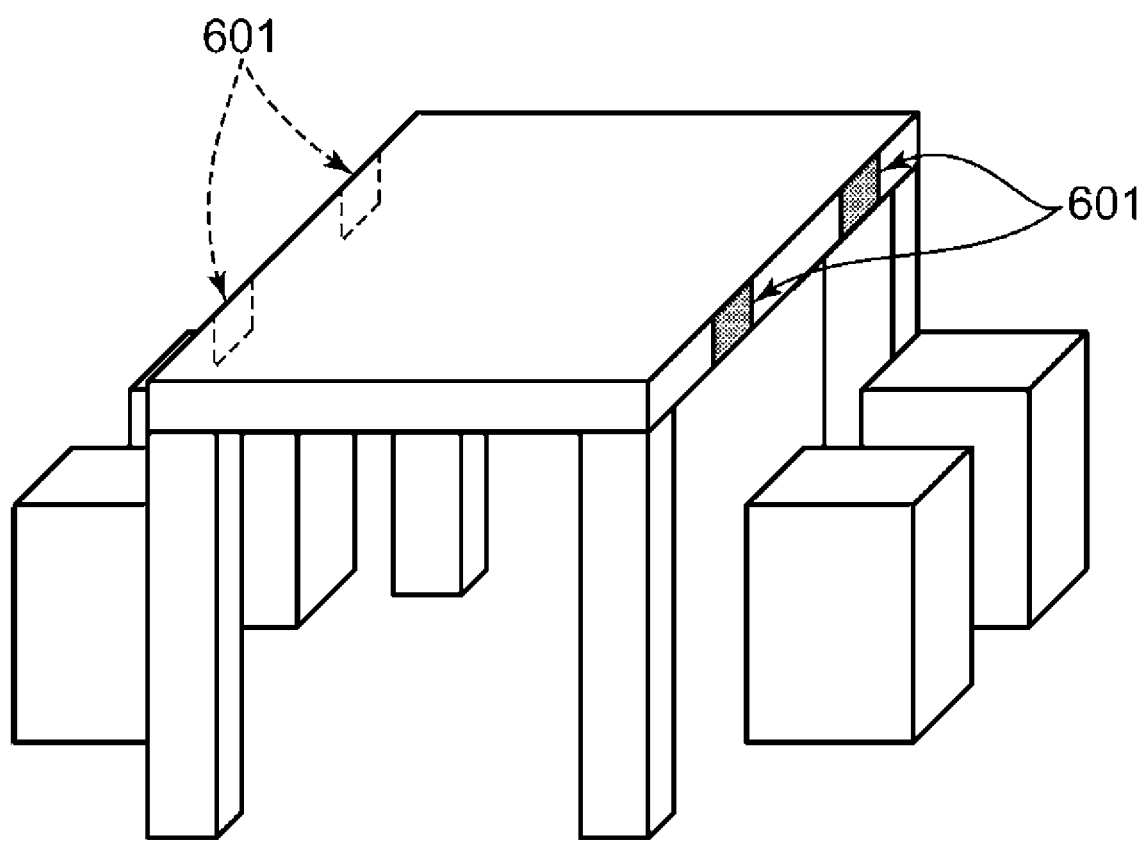
FIG. 6C is a diagram showing an example of a manner in which a QR code is set on a seat.

In the example in FIG. 6C, the QR code 601 is set not on the chair but on a side surface of a table (for example, on a side face facing a chair). In this example, the table is for four people, and four QR codes 601 corresponding to respective four seats are placed on side faces of the table.

Figure 6D:
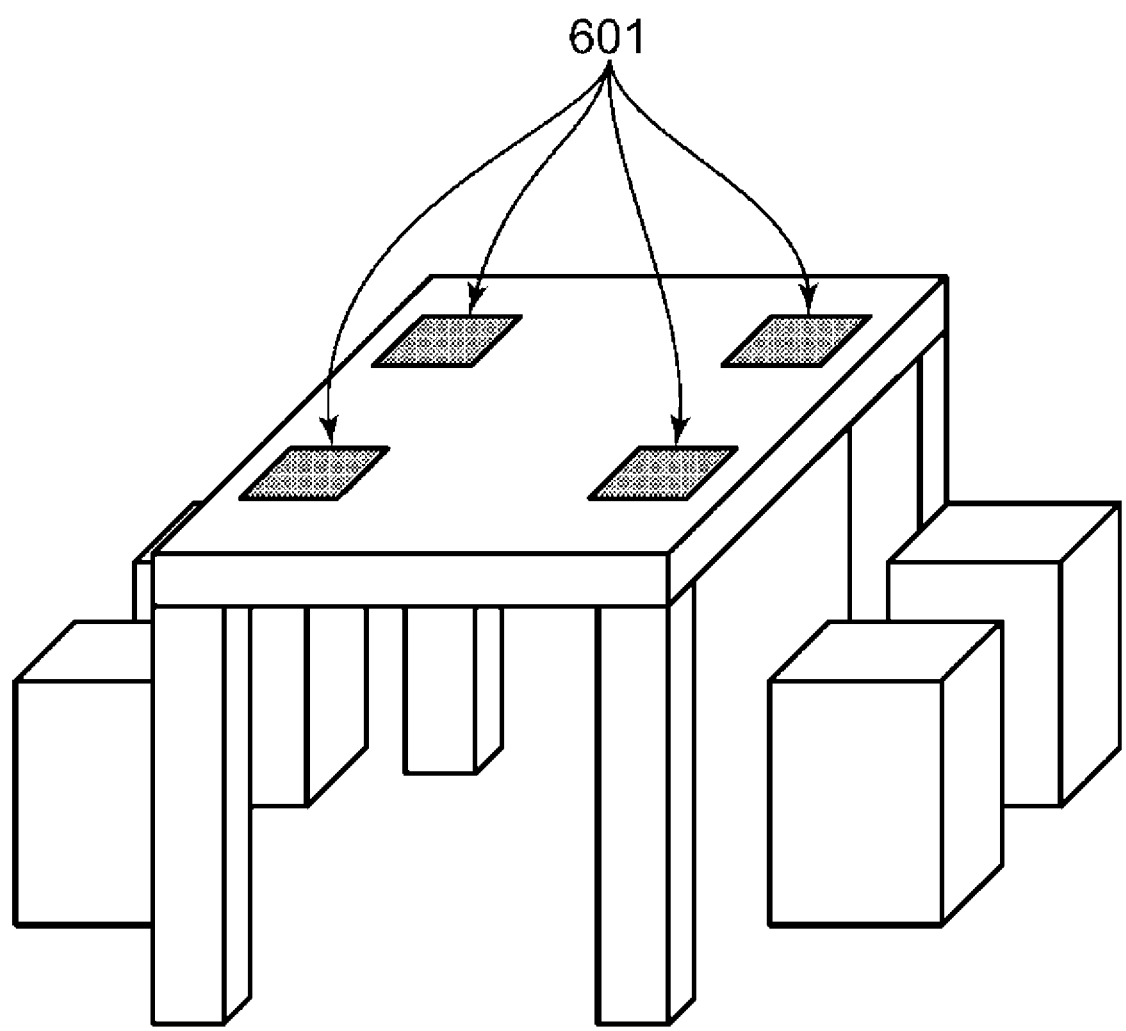
FIG. 6D is a diagram showing an example of a manner in which a QR code is set on a seat.

In the example in FIG. 6D, the QR code 601 is located on an upper surface of a table top plate. In this example, the table is for four people, and four QR codes 601 corresponding to respective seats are set on the upper surface of the table top plate. By locating the QR codes 601 on the upper surface of the table top plate, it becomes possible for users to easily notice the existence of the QR codes 601.

The QR code prepared for each seat is used by the information terminal 100 to acquire menu information available at the store when a user orders a dish. A detailed description is given below as to a method of ordering a dish using the QR code and the information terminal 100. In the present embodiment, a dish may be ordered using a standard menu or a personalized menu.

Ordering Using Standard Menu

The standard menu is for use in ordering a dish by a user who does not have or does not care about food allergies. The standard menu includes common dishes served for users in the store. A process of ordering a dish via the standard menu is described below with reference to various screens displayed on the information terminal 100.

The order process via the standard menu corresponds to a flowchart shown in FIG. 25, and thus the process is described below while referring to the flowchart in FIG. 25. First, the QR code reader is activated, and the QR code reader reads a QR code corresponding to a seat where a user is seated. This process corresponds to step S11 in FIG. 25.

Figure 7:
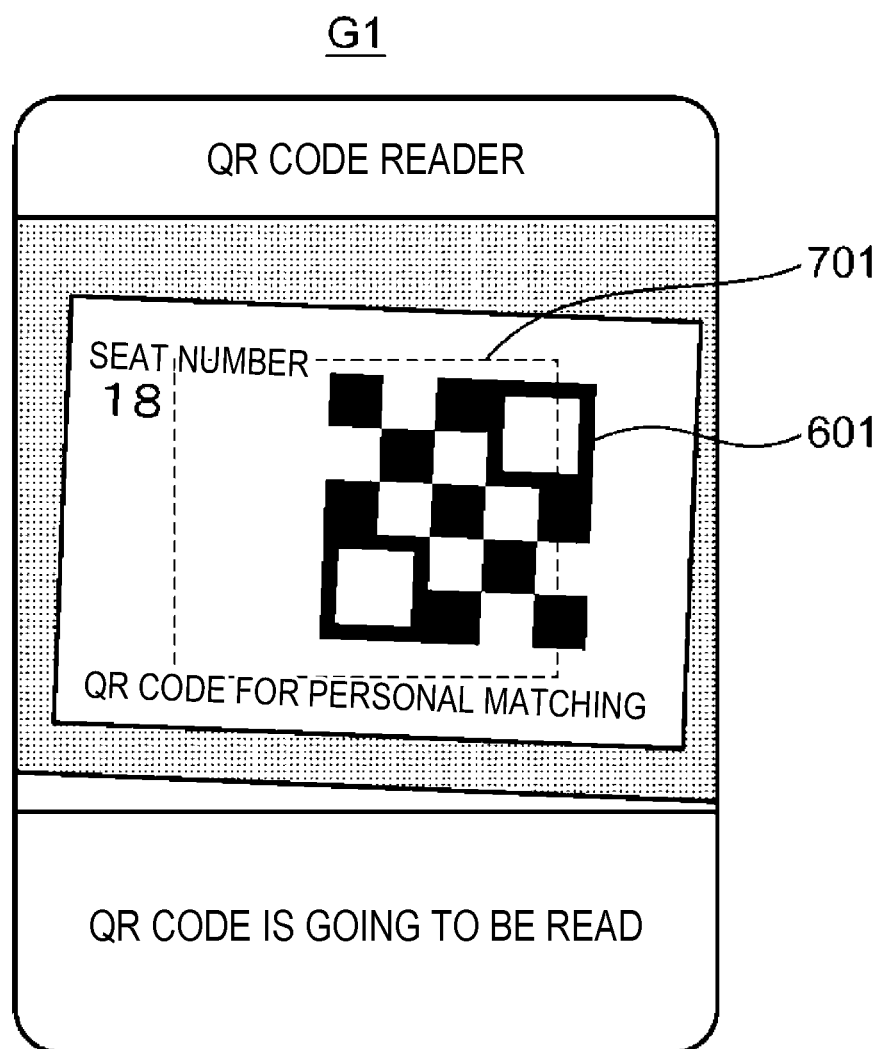
FIG. 7 is a diagram showing an example of an operation screen which is displayed on an information terminal when a user operates the information terminal to read a QR code.

FIG. 7 is a diagram showing an example of an operation screen G1 displayed on the information terminal 100 when the user operates the information terminal 100 to read the QR code. The operation screen G1 is displayed in a situation in which, after the user enters a store of a restaurant and is seated, the user operates the information terminal 100 to read the QR code corresponding to the seat where the user is seated. The QR code corresponding to the seat of the user is arranged in one of the manners shown in FIG. 6A to 6D. After the user is seated, the user takes out the information terminal 100 and operates the information terminal 100 to read the QR code corresponding to the seat of the user so as to acquire the standard menu of the store of the restaurant. The reading of the QR code is realized by using a general-purpose QR code reading application called a "QR code reader" pre-installed on the information terminal 100. FIG. 7 illustrates the operation screen G1 in a situation in which the user is performing an operation of focusing the information terminal 100 on the QR code corresponding to the seat of the user. The user adjusts the orientation and the position of the information terminal 100 such that the QR code 601 fits within an area surrounded by a guide line 701 (a broken-line square in the figure) of the QR code reader. Near the QR code 601 located at each seat, text information "Seat number 18" is provided such that a user or a staff of the store can identify the seat from this information. Furthermore, text information is also provided to indicate what the QR code 601 is (in this specific example, the text information indicating "QR code for personal matching"). Therefore, an image of "Seat number 18" and an image of the "QR code for personal matching" are also displayed on the operation screen G1.

Next, the standard menu information of the restaurant company A is acquired from the QR code read by the QR code reader. The standard menu is generated based on the standard menu information and displayed on the information terminal 100.

Figure 8:
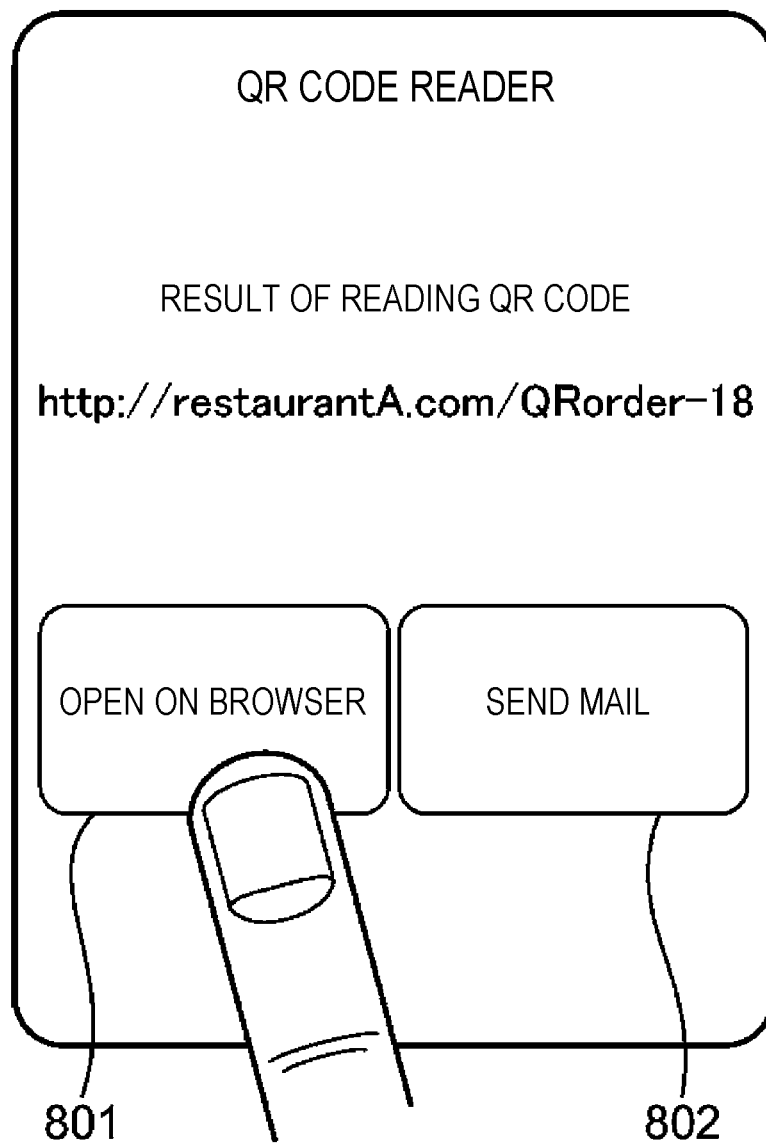
FIG. 8 is a diagram showing an example of an operation screen which is displayed on an information terminal immediately after a QR code reader reads a QR code.
Figure 25:
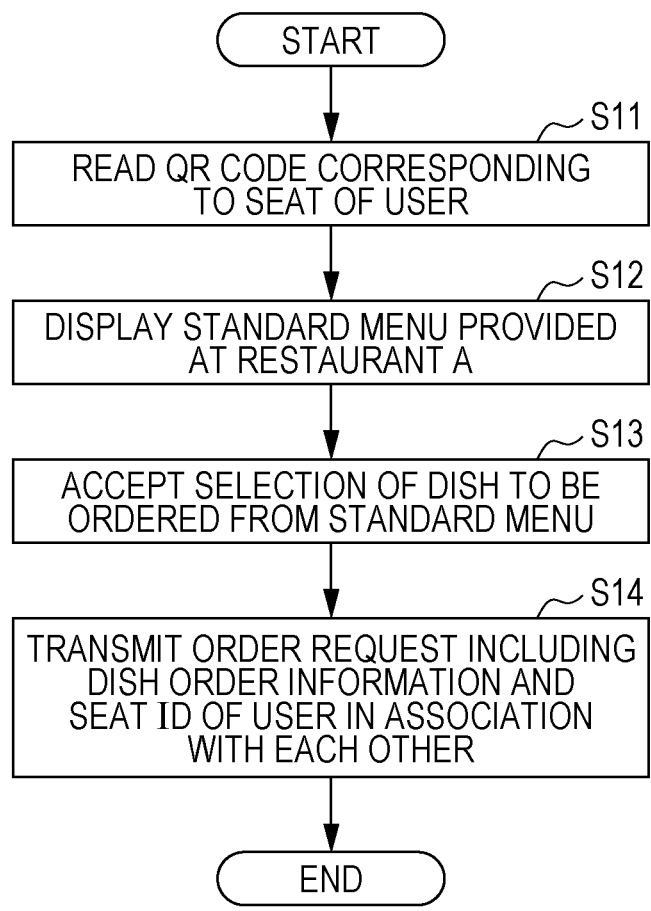
FIG. 25 is a flowchart showing an example of a process which is performed by an information terminal when a dish is selected from a standard menu and the selected dish is ordered.

This process corresponds to step S12 in FIG. 25. FIG. 8 is a diagram showing an example of an operation screen G2 which is displayed on the information terminal 100 immediately after the QR code is read by the QR code reader. On this operation screen G2, a character string successfully obtained as a result of reading the QR code by the QR code reader is displayed. In this specific example, "http://restaurantA.com/QRorder-18" obtained as the result of the reading by the QR code is displayed. The operation screen G2 includes a button 801 labeled "OPEN ON BROWSER" and a button 802 labeled "SEND MAIL". The button 801 is selected when the user recognizes that the character string displayed as the result of reading the QR code represents a URL. When the button 801 is touched, the Internet browser is started and a web page indicated by this URL is displayed on the information terminal 100.

The button 802 is selected when the user recognizes that the character string displayed as the result of reading the QR code represents a mail address. When the button 802 is touched, a mail application is started. In this specific example, the button 801 is touched to browse the standard menu.

To order a dish from this standard menu, it is not necessary to install a particular application on the information terminal 100, and it is sufficient if the QR code reader and the browser are available. Therefore, it is possible for many users to order dishes using the standard menu.

The browser can identify that the connection destination is the restaurant company A from connection destination information (for example, a domain name and the part of restaurantA.com) included in the character string (for example, the URL) read by the QR code reader. The second server 300 recognizes that the number at the end of the requested URL is 18, and thus the second server 300 determines that this request is issued from the browser of the information terminal 100, which has read the QR code of the seat with the seat number of "18". Although the character string shown in FIG. 8 does not include the store ID of the store 40, the character string may explicitly include information indicating the "store 40" (Store-A). In this case, the QR code represents the character string, for example, as "http://restaurantA.com/Store-A/QRorder-18". The browser of the information terminal 100 acquires the requested connection destination information in the manner described above.

Figure 9:
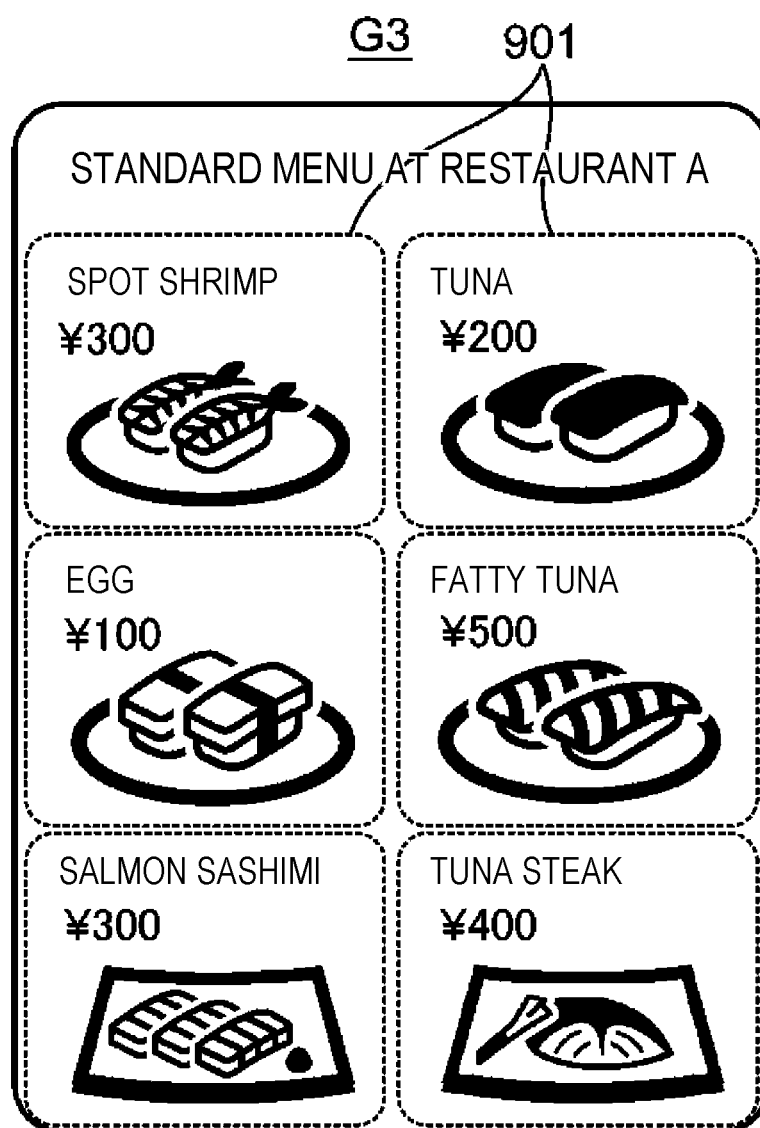
FIG. 9 is a diagram showing an example of an operation screen including a standard menu.

FIG. 9 is a diagram illustrating an example of an operation screen G3 including the standard menu provided by the restaurant company A. This operation screen G3 is displayed when the standard menu information is received by the information terminal 100. The standard menu simply includes dishes included in the standard menu information, and nothing is taken into account as to the allergy information related to the user. The standard menu information may be the same as the menu information used in generating a personalized menu, or may be different from it.

A plurality of tile objects 901 are arranged in the form of a matrix on the operation screen G3. The standard menu is formed using these tile objects 901. One tile object 901 corresponds to one dish included in the standard menu. Each tile object 901 includes the name of a dish, the price of the dish, and the image of the dish. On the operation screen G3, the standard menu scrolls in response to a scroll operation performed by the user. As a result, other dishes that are not displayed previously on the operation screen G3 appear on the operation screen G3. By performing the scroll operation in the above-described manner, the user can browse all dishes included in the standard menu.

The operation screen G3 is displayed when the browser connects to the URL indicated by the character string obtained as a result of reading the QR code (for example, http://restaurantA.com/QRorder-18) and the browser receives the menu information from the second server 300 of the restaurant company A.

For example, the browser of the information terminal 100 connects to the above-described URL and issues an HTTP request for an HTML file for drawing the standard menu of the restaurant company A. When the browser receives an HTTP response from the second server 300 of the restaurant company A, the browser draws the operation screen G3 including the standard menu according to the received HTTP response. However, the above-described implementation is merely an example, and the drawing of the operation screen G3 may be realized by other technical means.

Next, the user selects a dish from the displayed standard menu. This process corresponds to step S13 in FIG. 25.

Figure 10:
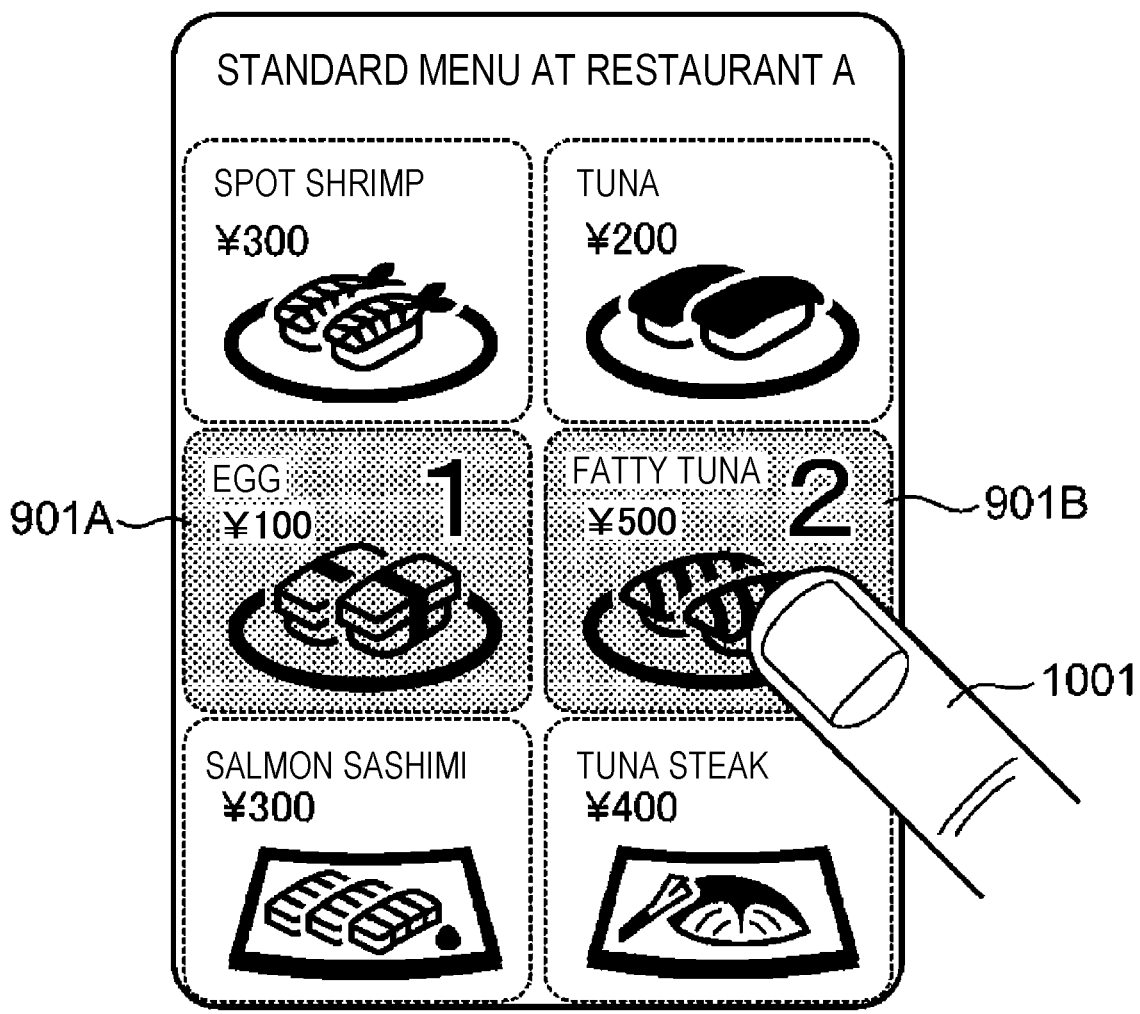
FIG. 10 is a diagram showing a scene in which a user operates an operation screen to select food from a standard menu and order the selected food.

FIG. 10 is a diagram showing an example of a scene in which a user operates the operation screen G3 to order a dish from the standard menu. As shown in this figure, the user can determine a dish to be ordered by performing a touch operation using a pointing element 1001 such as a finger. For example, when the information terminal 100 detects that the tile object 901A corresponding to a dish of "egg" is touched once, the color of the tile object 901A is changed from a first color, which is a default color, to a second color to indicate that the tile object 901A is selected. Furthermore, the information terminal 100 displays "1", for example, in the upper right corner of the tile object 901A thereby indicating the number of ordered dishes for "egg". In this example, a tile object 901B corresponding to a dish of "fatty tuna" is further touched twice by the user. Therefore, the color of the tile object 901B is changed from the first color to the second color, and "2" indicating the number of ordered dishes is displayed on the upper right of the tile object 901B. Thus, in this example, one dish of "egg" and two dishes of "fatty tuna" are selected from the standard menu. As described above, the user can order a dish by touching a tile object 901 corresponding to a desired dish, that is, the user can intuitively and easily order the desired dish by performing a familiar operation.

In this example, the color of a tile object 901 is changed when the user selects a dish to order, but this is merely an example, and the present embodiment is not limited to this. For example, the pattern of a tile object 901 may be changed from a first pattern to a second pattern when selected by the user. Alternatively, the color and pattern of a tile object 901 may be changed from the first color and the first pattern to the second color and the second pattern when selected by the user.

Figure 11:
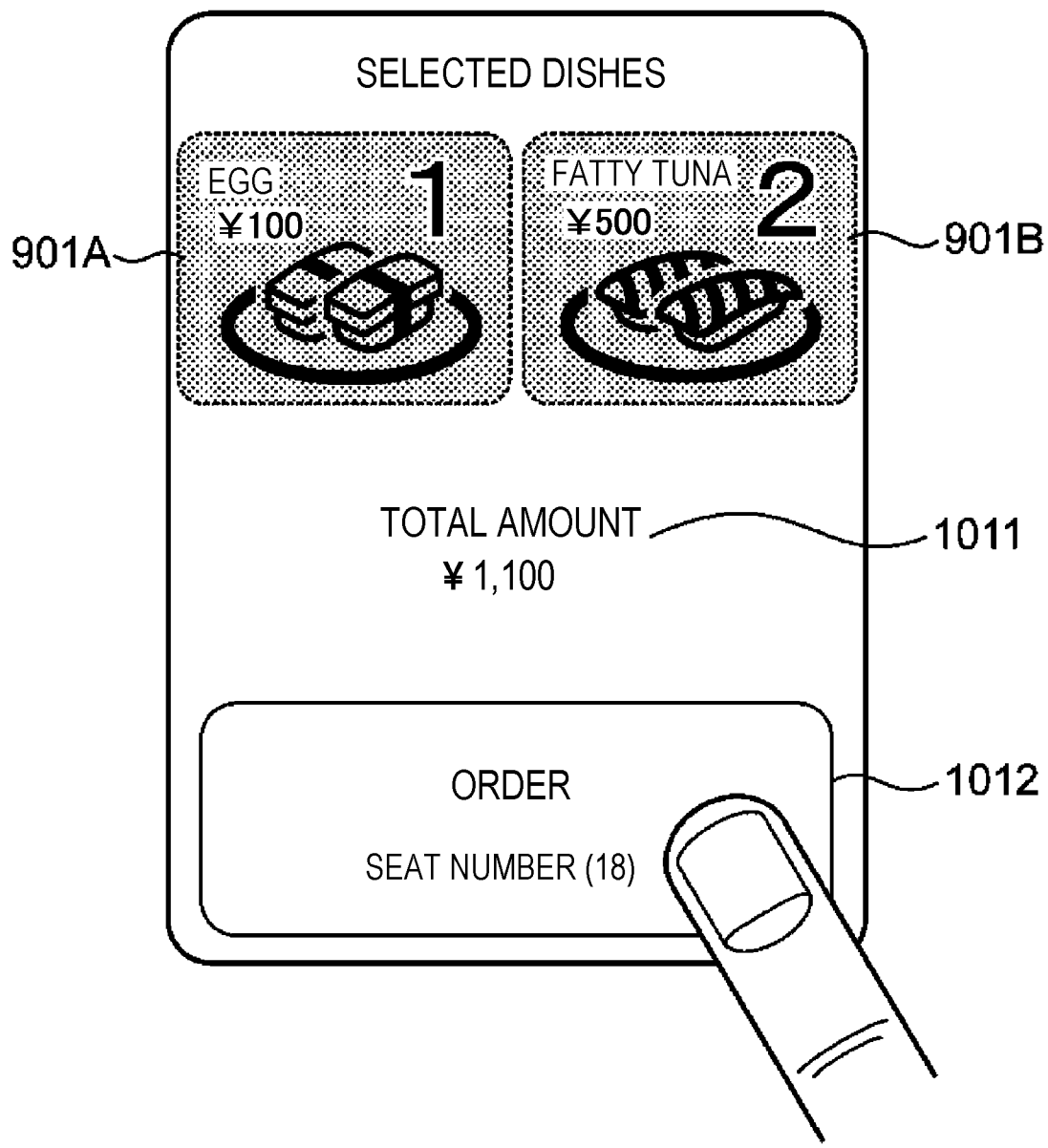
FIG. 11 is a diagram showing an example of an operation screen which is displayed when a dish is selected from a standard menu and the selected dish is finally determined to be ordered.

FIG. 11 is a diagram showing an example of an operation screen G4 which is displayed when a dish selected from the standard menu is finally ordered. The operation screen G4 is displayed when an order button (not shown in FIG. 9) on the operation screen G3 is touched by the user to finally decide the order of the dish. The operation screen G4 includes the tile objects 901A and 901B corresponding to the dishes selected on the operation screen G3, a total amount field 1011 in which the total amount of the ordered dishes (for example, 1,100 yen) is displayed, and an order button 1012 which is touched to make a final decision. As described above, the operation screen G4 displays a list of dishes to be ordered, the quantity of each dish, and the total amount of dishes to be ordered such that the user can efficiently confirm the details of the order on a single screen. If the user confirms that the order contents are correct, the user touches the order button 1012 at the bottom of the operation screen G4. As a result, the dish order is finally confirmed. Since the seat number "18" is displayed on the order button, the user can confirm that the ordered dish is to be served to the seat of the user. When the order button 1012 is touched, the information terminal 100 transmits an order request including ordered-dish information indicating the selected dish and the seat ID ("18" in the example shown in FIG. 11) read from the QR code in association with each other, to the second server 300 of the restaurant company A. Thus, the order process using the standard menu is completed. This process corresponds to step S14 in FIG. 25.

The order process using the standard menu for general users is carried out as described above. In this order process, a user can order a dish such that the user operates the information terminal 100 so as to read a QR code and display the standard menu provided at the restaurant company A on the browser, and the user orders the dish via this standard menu. Thus, it is not necessary perform a troublesome operation to pre-install, on the information terminal 100, a specific application such as that provided by the restaurant company A. That is, users can immediately use this service by using the information terminal 100, which makes it possible for many users to use this service. In addition, users can easily select and order a desired dish by intuitive operation through the standard menu. Furthermore, the operation screen G3 allows it to change the zoom magnification by performing a pinching operation. This allows even users with presbyopia to easily see dishes included in the operation menu. Furthermore, users can browse more information at the same time by reducing the operation screen G3. Furthermore, the order request is issued by an HTTP request in which the ordered-dish information and the seat ID (for example, the seat number "18") are indicated in association with each other, the second server 300 of the restaurant company A recognizes the dish ordered by a user at the seat with the seat number "18" via the HTTP request, and displays the recognized seat number "18" and the ordered dish on a display in the store.

This allows a restaurant employee to serve the ordered dish correctly to the user at the seat with the seat number "18". Furthermore, the standard menu is provided not by a paper medium. This allows the restaurant company A to avoid a troublesome operation of updating or managing the standard menu, which would be required when the standard menu is provided by a paper medium. As a result, human resources for taking orders and the risk of complaints that mistakenly accept orders are reduced, and cost reduction and management efficiency are achieved.

Order Using Personalized Menu

Next, ordering dishes using a personalized menu is described below. The personalized menu is provided by a restaurant and it includes similar dishes to those included in the menu for general customers, but it is modified by removing or reducing ingredients that may cause a strong allergic reaction that is harmful to user's health from the dished listed in the menu. Alternatively, the personalized menu may be prepared by removing dishes containing ingredients that may cause a strong allergic reaction that is harmful to the user's health. Here, the strong allergic reaction that is harmful to health here refers to an allergic reaction that is caused by an allergen to which the user is diagnosed as positive in an allergic test, which is aware of by the user and that is to be considered in daily life. An ingredient, which may cause a relatively weak allergy reaction such as that which is diagnosed as negative or false positive in an allergen test, may be removed from dishes listed in a personalized menu or may be treated such that the amount of the ingredient is reduced to a level low enough not to cause an allergic problem and dishes including this ingredient may be included in the personalized menu.

Figure 26:
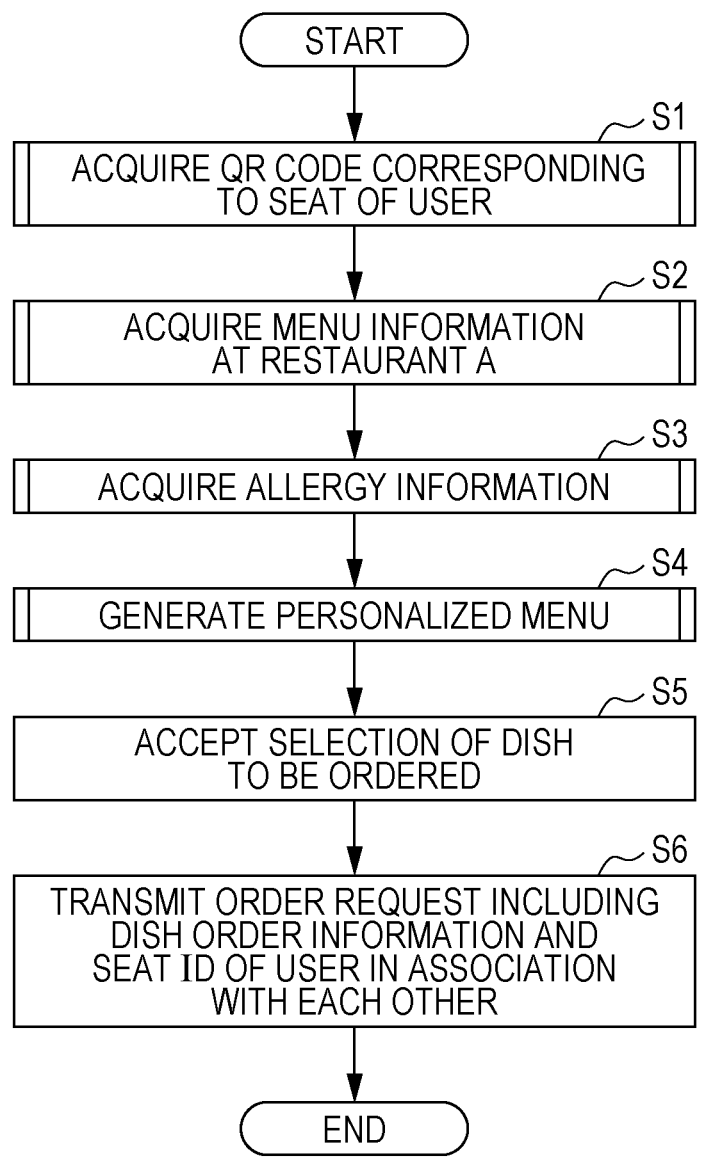
FIG. 26 is a flowchart showing an example of a process which is performed by an information terminal when a dish is selected from a personalized menu and the selected dish is ordered.

A process of ordering a dish using the personalized menu is shown in a flowchart in FIG. 26. Referring to this flowchart in FIG. 26, the process of ordering a dish using the personalized menu is described below.

Figure 12:
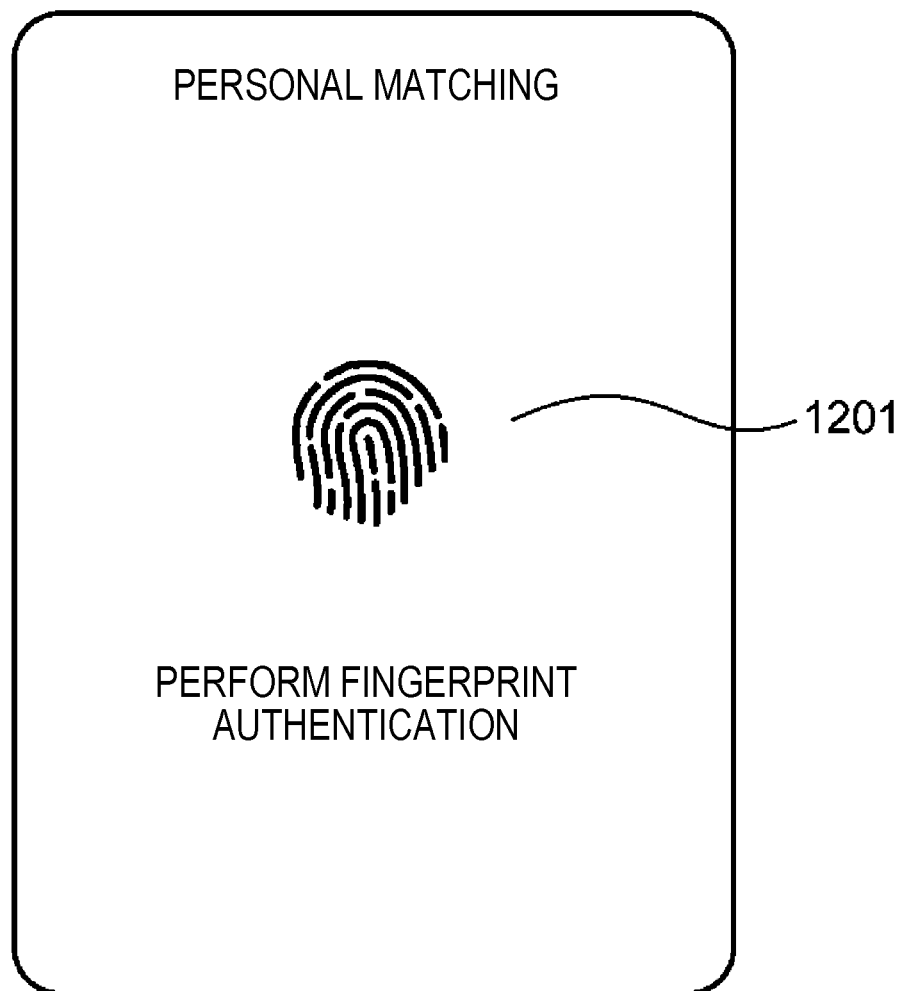
FIG. 12 is a diagram showing an example of an authentication screen which is displayed on an information terminal immediately after a user, who wants to order a dish, starts a matching application.

Starting of the process of ordering a dish from the personalized menu is triggered by activating a matching application. FIG. 12 is a diagram showing an example of an authentication screen G101 which is displayed on the information terminal 100 immediately after the matching application is activated by a user who wants to order a dish. The authentication screen G101 is a screen for use by a user in performing a user authentication process using a fingerprint. On the authentication screen G101, a fingerprint image 1201 schematically illustrating a fingerprint is displayed in the center, and a message "Perform fingerprint authenticate" is displayed below the fingerprint image 1201. Thus, the authentication screen G101 prompts the user to perform fingerprint authentication. A character string "Personal matching" is displayed at the top of the authentication screen G101. This allows the user to recognize that the authentication screen G101 is for the matching application. This also applies to FIGS. 13 to 16 described later.

Figure 13:
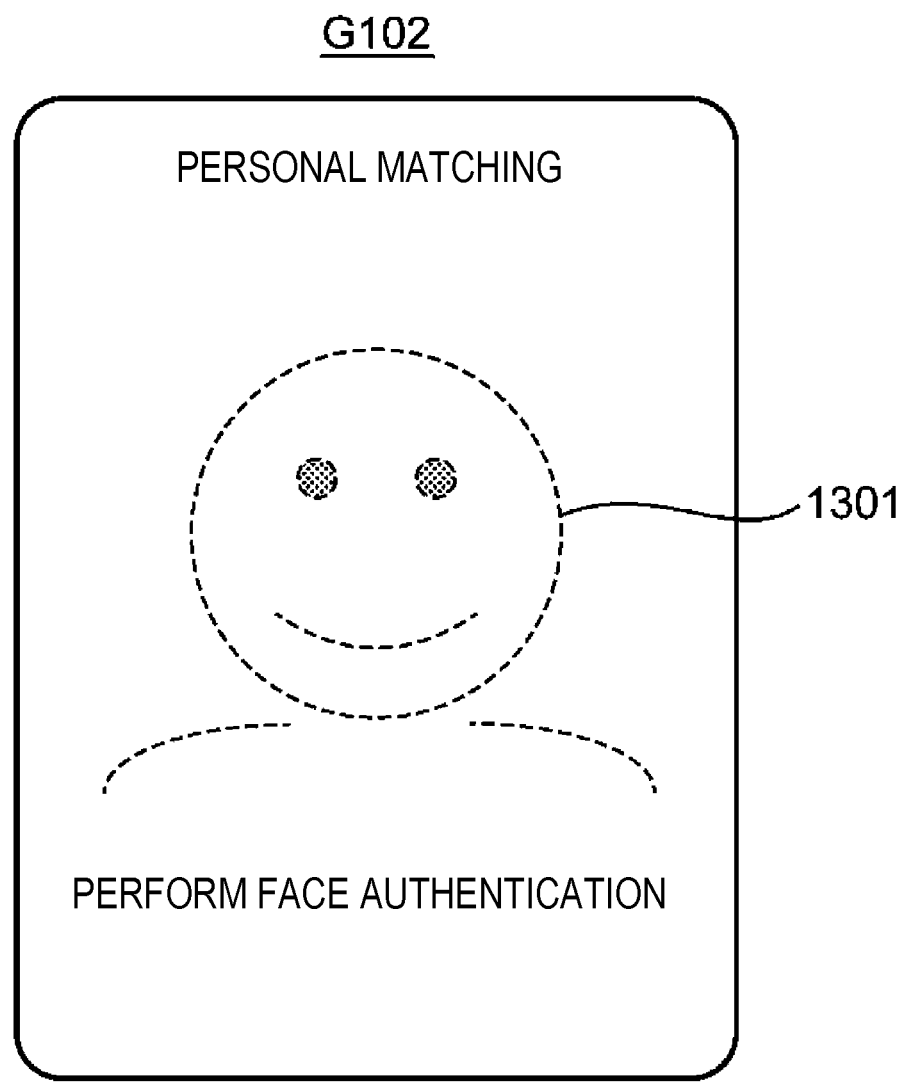
FIG. 13 is a diagram showing another example of an authentication screen.

FIG. 13 is a diagram showing another example of an authentication screen G102. The authentication screen G102 is an example of a screen for performing user authentication by face authentication. On the authentication screen G102, a dashed line 1301 schematically showing an outline of a face is displayed in the center such that the information terminal 100 can capture an image of a face of a user from the front of the user in an appropriate size. The user adjusts the orientation and the position of the information terminal 100 such that the image of the face of the user as captured from the front of the user is displayed within an area surrounded by the dashed line 1301.

In a case where there is a user authentication method that allows a user to perform authentication with sufficiently high accuracy with a less burden on the user as compared with the above-described user authentication methods, such a method may be used. As a method of user authentication, a method of inputting a user ID and a password may be used, or two-step authentication may be employed to achieve a high security level.

Figure 14:
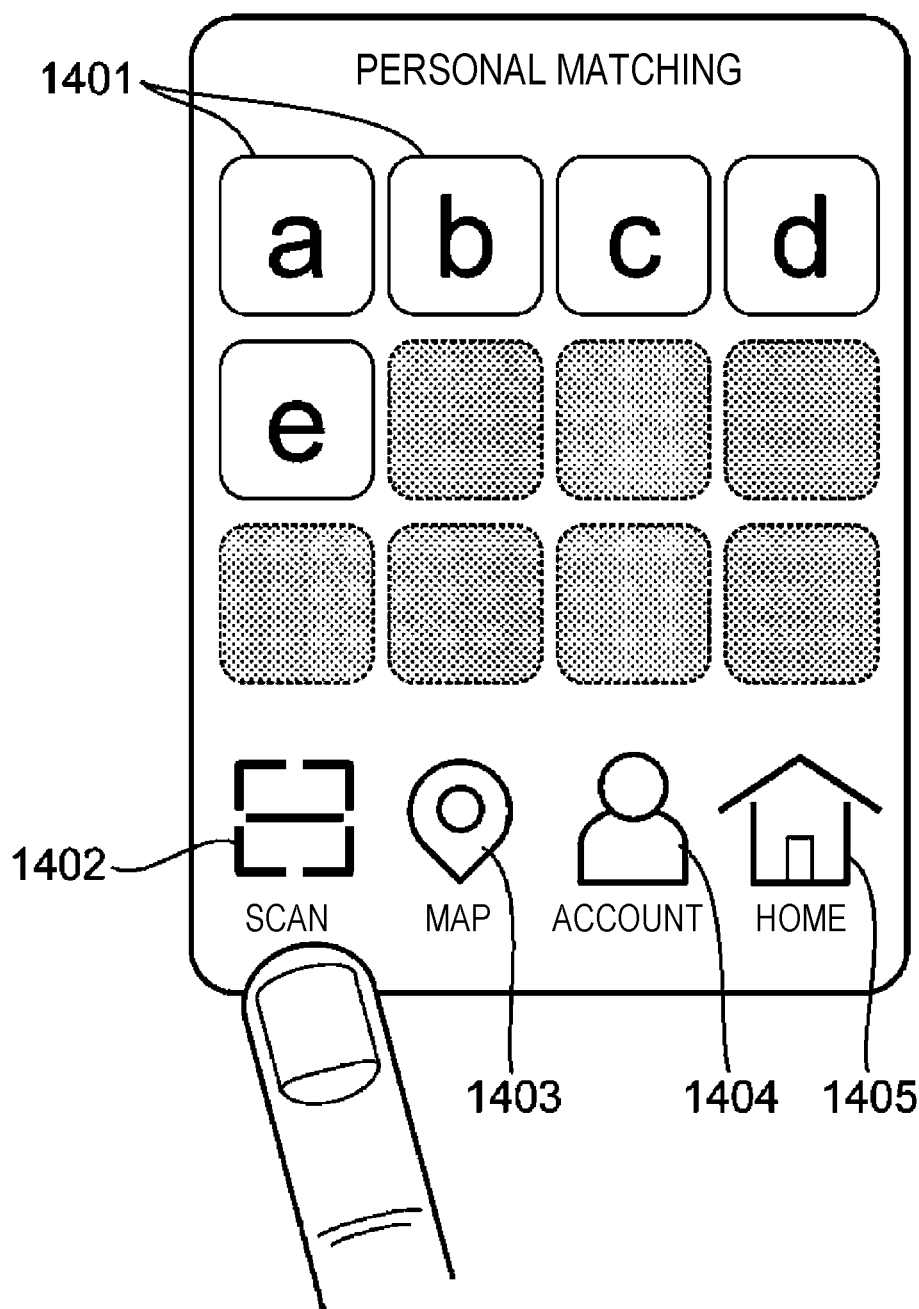
FIG. 14 is a diagram showing an example of a home screen which is displayed immediately after user authentication by a matching application is completed.

FIG. 14 is a diagram showing an example of a home screen G103 which is displayed immediately after the user authentication by the matching application is completed. On the home screen G103, an application name "PERSONAL MATCHING" is displayed in a top area, and a plurality of tile objects 1401 are displayed in the form of a matrix in a middle area. Each tile object 1401 is associated with a cooperation function or another application incorporated by the matching application. Another application is, for example, an application which runs in the matching application. In this example, five tile objects 1401 labeled a, b, c, d, and e are displayed. These tile objects 1401 are respectively associated with dedicated functions (for example, an application in the matching application) that perform matching with company's products or services in cooperation with the matching application. Thus, the user can use five cooperation functions indicated by a, b, c, d, and e. Grayed-out tile objects 1401 are empty tile objects to which no cooperation function is installed. At the bottom of the home screen, from the left to the right, a scan button 1402, a map button 1403, an account button 1404, and a home button 1405 are displayed. These four buttons are fixed buttons. The scan button 1402 is a button used to perform reading a QR code or the like linked to a service provided by a company such as a restaurant or the like described above. The map button 1403 is a button used to display, on a map screen, stores which are located near the current location of the information terminal 100 and in which the matching application is usable. The account button 1404 is a button for registering or editing user's account information. Registration and editing of the account information includes, for example, setting of personal authentication and setting of a cooperation function with the first server 200. The home button 1405 is a button used to return the display screen to the home screen G103 shown in FIG. 14.

On the home screen G103, tile objects 1401 for using a cooperation function, another application, and a service provided by another company are collectively arranged in the middle area. These tile objects 1401 can be set according to preference of a user in terms of whether each tile object 1401 is displayed or not, and where each tile object 1401 is displayed. Therefore, the user is allowed to acquire, by using a single matching application, products and/or services suitable for the user selected based on personal information from those provided by many companies (for example, home appliance mass retailers, DVD/Blu-ray (registered trademark) rental stores, bookstores, coffee shops, taxis, etc.).

FIG. 15 is a diagram showing an example of an operation screen G104 which is displayed on the information terminal 100 when, after the user starts the matching application, the user operates the information terminal 100 to read a QR code corresponding to a seat of the user. The operation screen G104 (an example of a first operation screen) is similar to the operation screen G1 shown in FIG. 7 except that in the operation screen G104, the name of the application displayed on the top is "PERSONAL MATCHING".

The matching application can determine that a connection destination is the restaurant company A from a connection destination information (for example, a domain name, restaurantA.com) indicated by a character string (for example, a URL) read from the QR code. When the second server 300 receives this request, the second server 300 detects that the number at the end of the URL requested by the matching application is "18", and thus the second server 300 determines that this request is a request transmitted from the information terminal 100 that read the QR code of the seat with the seat number "18". The present embodiment is described below by way of example for a case where a dish is ordered by a user seated in a seat with the seat number "18" in a store 40 of the restaurant company A. In this request, the matching application may explicitly specify the store 40 (Store-A). In this case, the character string represented by the QR code may be set as, for example, http://restaurantA.com/Store-A/QRorder-18. The matching application can acquire information identifying the connection destination (for example, the restaurant ID) in the manner described above.

The above-described process of starting the matching application, performing user authentication, and reading the QR code corresponds to step S1 in FIG. 26.

Next, a description is given below as to a process performed by the matching application to access the second server 300 of the restaurant company A and acquire menu information. This process corresponds to step S2 in FIG. 26.

Figure 16:
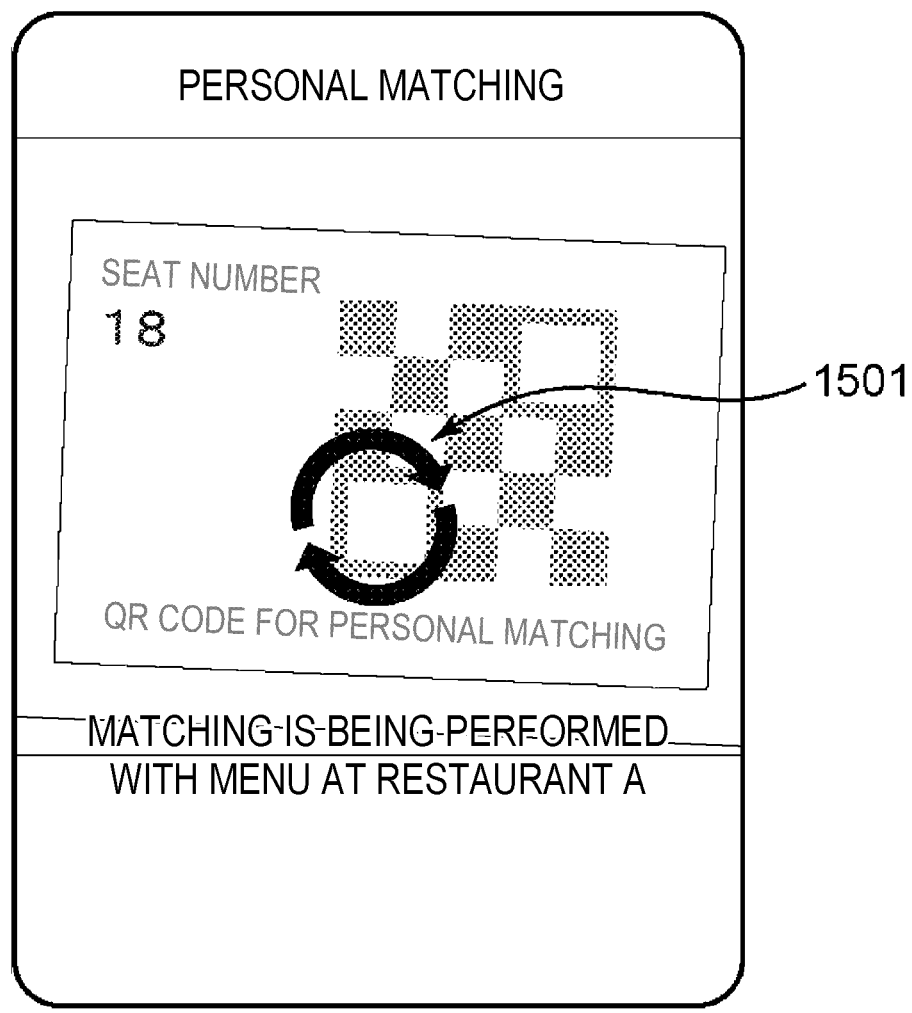
FIG. 16 is a diagram showing an example of a display screen which is displayed on an information terminal when a matching application is generating a personalized menu.

FIG. 16 is a diagram showing an example of a display screen G105 which is displayed on the information terminal 100 when the matching application is generating a personalized menu. On the display screen G105, an image of a QR code captured via the operation screen G104 is displayed with reduced transparency, and a rotating circular arrow object 1501 is displayed on the image of the QR code. Furthermore, below the arrow object 1501, a character string "MATCHING IS BEING PERFORMED WITH MENU AT RESTAURANT A" is displayed. This allows the user to recognize that the matching application is in operation.

When the display screen G105 is being displayed, the matching application on the information terminal 100 generates a personalized menu in cooperation with the second server 300 of the restaurant company A and the first server 200. More specifically, the matching application accesses the second server 300 of the restaurant company A based on the URL indicated by the read QR code, and acquires the menu information. After the matching application acquires the menu information, the matching application detects a data attribute of the menu information. In this case, the menu information is information regarding food, and thus a food attribute is detected as the data attribute.

The menu information is given, for example, in the form of an HTML file. For example, the menu information includes information indicating, in a predetermined format, that the data attribute is the food attribute. According to this format, the matching application may detect that the data attribute of the menu information is the food attribute. Alternatively, the matching application may detect that the data attribute of the menu information is the food attribute from a domain name of the URL indicated by the QR code. In this specific example, the domain name "restaurantA.com" indicates the restaurant company A, and thus it is determined that the data attribute of the menu information is the food attribute. Alternatively, the matching application may analyze the acquired menu information, and may detect the data attribute such that in a case where the analysis indicates that the data is related to food, it is determined that the data attribute of the menu information is the food attribute. Alternatively, the matching application may detect the data attribute such that supplementary information indicating the data attribute of the menu information is acquired from the second server 300, and it is determined that the data attribute of the menu information is the food attribute. Another method may be used in the implementation of the process of detecting the data attribute of the menu information as long as the data attribute can be identified.

Next, a description is given below as to a process performed by the matching application to acquire allergy information from the second server 300. This process corresponds to step S3 in FIG. 26.

When the matching application determines that the data attribute of the menu information is the food attribute, the matching application requests the first server 200 to provide latest allergy information, which is classified in the food attribute and indicates a meal restriction condition of the user. This request includes the user ID. Upon receiving this request, the first server 200 extracts, based on the user ID, the latest allergy information from the personal information which is distributed and encrypted. The extracted allergy information is transmitted from the first server 200 to the information terminal 100. Thus, the matching application acquires the allergy information. Details of allergy information will be described later with reference to FIG. 21.

After the information terminal 100 acquires the allergy information, the information terminal 100 executes a process of checking the menu information of the restaurant company A and the allergy information, and generating a personalized menu. This process corresponds to step S4 in FIG. 26. During this process, the display screen G105 shown in FIG. 16 is still displayed on the information terminal 100, although the matching application is executing the process of checking the menu information and the allergy information and generating the personalized menu according to the allergy information. A plurality of methods may be used to generate the personalized menu.

A first method is to generate the personalized menu by excluding dishes that contain any slight amount of ingredient that may cause an allergic reaction to the user. Allergic reactions to ingredients are classified into 7 classes from class 0 to class 6 in ascending order as described later. More specifically, ingredients which are negative as allergen, that is, ingredients which have almost no possibility of causing an allergic reaction are classified in class 0. Ingredients which are false positive as allergen, that is, ingredients which have a relatively low possibility of causing an allergic reaction are classified in class 1. Classes 2 to 6 respectively include ingredients which are positive as allergen, and the possibility of causing allergic reaction increases as the class increases. In the first method, for example, dishes containing any slight amount of ingredients in class 1 or higher classes are excluded from the personalized menu such that the personalized menu includes dishes containing only ingredients in class 0 or lower.

In a second method, when a dish of interest includes an ingredient having a possibility of causing an allergic reaction, if the allergic reaction of the user to this ingredient is relatively low, this dish is left in the personalized menu. In this second method, for example, dishes containing ingredients in class 2 or higher are excluded from the personalized menu, and dishes containing ingredients in class 1 or lower (negative and false positive as allergen) are left in the personalized menu.

A third method is to calculate the total value of amounts of ingredients (in units of grams) multiplied by values of allergic reaction levels to the ingredients (in units of IU/mL) and change dishes included in the personalized menu depending on the total value. For example, the total values calculated for the respective dishes are classified into three levels of low, medium, high, and dishes included in the personalized menu are changed according to the classification result.

For example, dishes with total values in the low level range cause low-level allergic reactions, and thus the dishes are registered in the personalized menu without changing the cooking method.

Dishes with total values in the middle level range can cause some allergic reactions, and thus the cooking method is changed such that the total values fall within the low level range, and the resultant dishes are registered in the personalized menu. More specifically, the cooking method is changed, for example, such that the amounts of respectively allergic ingredients are reduced until the total values fall within the low level range. Alternatively, when a dish has a total value in the middle level range, the cooking method is changed such that the dish does not include any slight amount of ingredient having an allergic reaction level (IU/mL) higher than the criterion value, and the resultant dish may be registered in the personalized menu.

For example, dishes with total values in the high level range can cause strong allergic reactions, and thus they are removed from the personalized menu.

Not eating any foods that may cause an allergic reaction can cause a serious problem in terms of the nutritional balance, in particular, to growing children. Therefore, it is important to provide an information processing system that dynamically changes the cooking method for each user depending on the degree of allergic reaction instead of cooking dishes using only ingredients that do not cause allergic reactions at all or that can cause extremely low allergic reactions.

After the matching application generates the personalized menu, the matching application displays the resultant personalized menu on the information terminal 100 using a browser in a similar manner to the case in which the standard menu for taking an order is displayed. The dishes listed in the personalized menu are all highly safe dishes determined taking into account the latest allergy information. Therefore, the user can eat any of listed dishes without having allergic problems.

Figure 17:
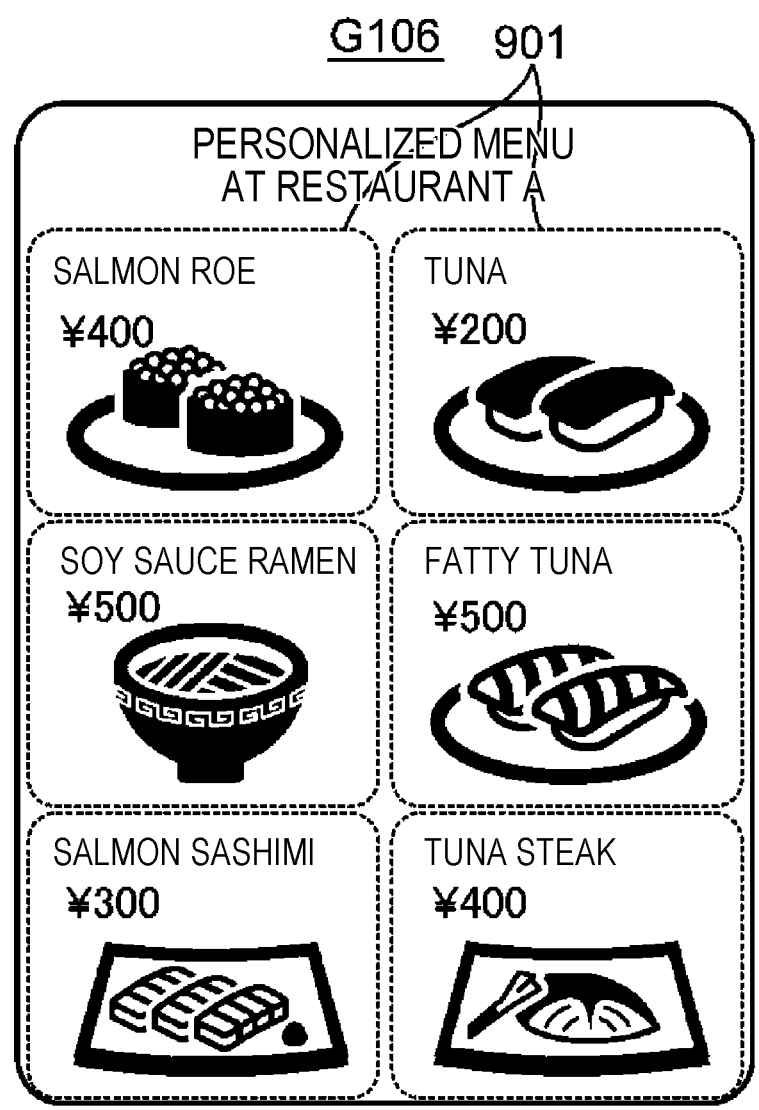
FIG. 17 is a diagram showing an example of an operation screen including a personalized menu.
Figures 20, 21:
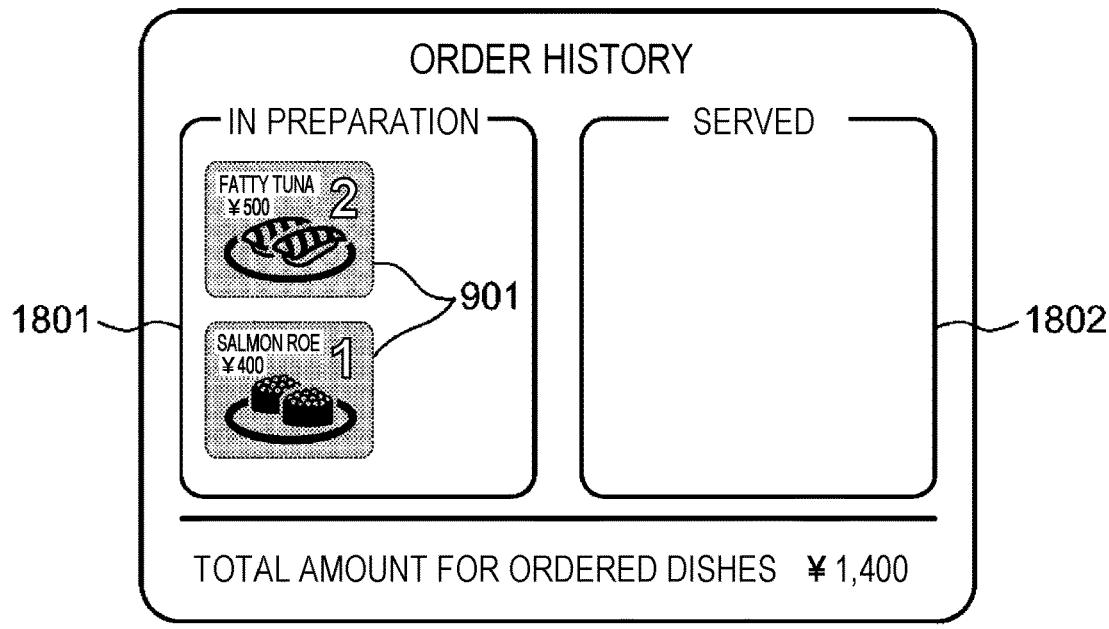
FIG. 20 is a diagram showing an example of an order history screen which is displayed in response to a request for seeing an order history issued by a user.
FIG. 21 is a diagram showing an example of a data structure of latest allergy information related to a user returned from a first server to a matching application.

FIG. 17 is a diagram illustrating an example of an operation screen G106 including a personalized menu. This operation screen G106 (an example of the second operation screen) includes a plurality of tile objects 901 arranged in the form of a matrix as with the operation screen G3. On the operation screen G106, the personalized menu is configured to be scrollable in response to a scroll operation performed by the user. The personalized menu is formed by these tile objects 901. On the operation screen G106, the tile objects 901 of "spot shrimp" and "egg" are removed from the standard menu shown in FIG. 9, and tile objects 901 of "salmon roe" and "soy sauce ramen" are added instead. This is because, as shown in FIG. 21, the allergic reaction level of this user to shrimp is "632.38", and "25.40" to egg. That is, the allergic reaction levels of this user to these ingredients are high. After the two dishes of "spot shrimp" and "egg" are removed, two dishes of "salmon roe" and "soy sauce ramen" are instead added to the personalized menu. However, this is merely an example, and the personalized menu may not include dishes substituting the removed dishes. In this case, the personalized menu is generated by deleting dishes containing ingredients causing high-level allergic reactions from the menu information.

At the top of the operation screen G106, a character string "PERSONALIZED MENU AT RESTAURANT A" is displayed, which explicitly indicates that the personalized menu displayed on the operation screen G106 is a menu personalized for a specific user. This allows the user to understand that the user can safely eat any dishes listed on the personalized menu displayed on the operation screen G106.

After the matching application displays the personalized menu, the matching application executes a process of accepting a selection of a dish to be ordered by the user. This process corresponds to step S5 in FIG. 26. FIG. 18 is a diagram showing a scene in which the user operates the operation screen G106 to select a dish from the personalized menu to order the selected dish.

In this specific example, the operation screen G106 is operated such that a tile object 901C of a dish of "salmon roe" is touched once and a tile object 901D of a dish of "fatty tuna" is touched twice on the personalized menu. As a result, the color of the tile object 901C is changed from a first color to a second color, and "1" indicating the number of ordered dishes is displayed in the upper right. In addition, the color of the tile object 901D is changed from the first color to the second color, and "2" indicating the number of ordered dishes is displayed in the upper right. In this way, the user can easily and intuitively order a dish by performing a touch operation using a pointing element 1001 such as a finger.

In this example, the color of a tile object 901 is changed when the user selects a dish to order, but this is merely an example, and the present embodiment is not limited to this. For example, the pattern of a tile object 901 may be changed from a first pattern to a second pattern when selected by the user. Alternatively, the color and pattern of a tile object 901 may be changed from the first color and the first pattern to the second color and the second pattern when selected by the user.

Figure 19:
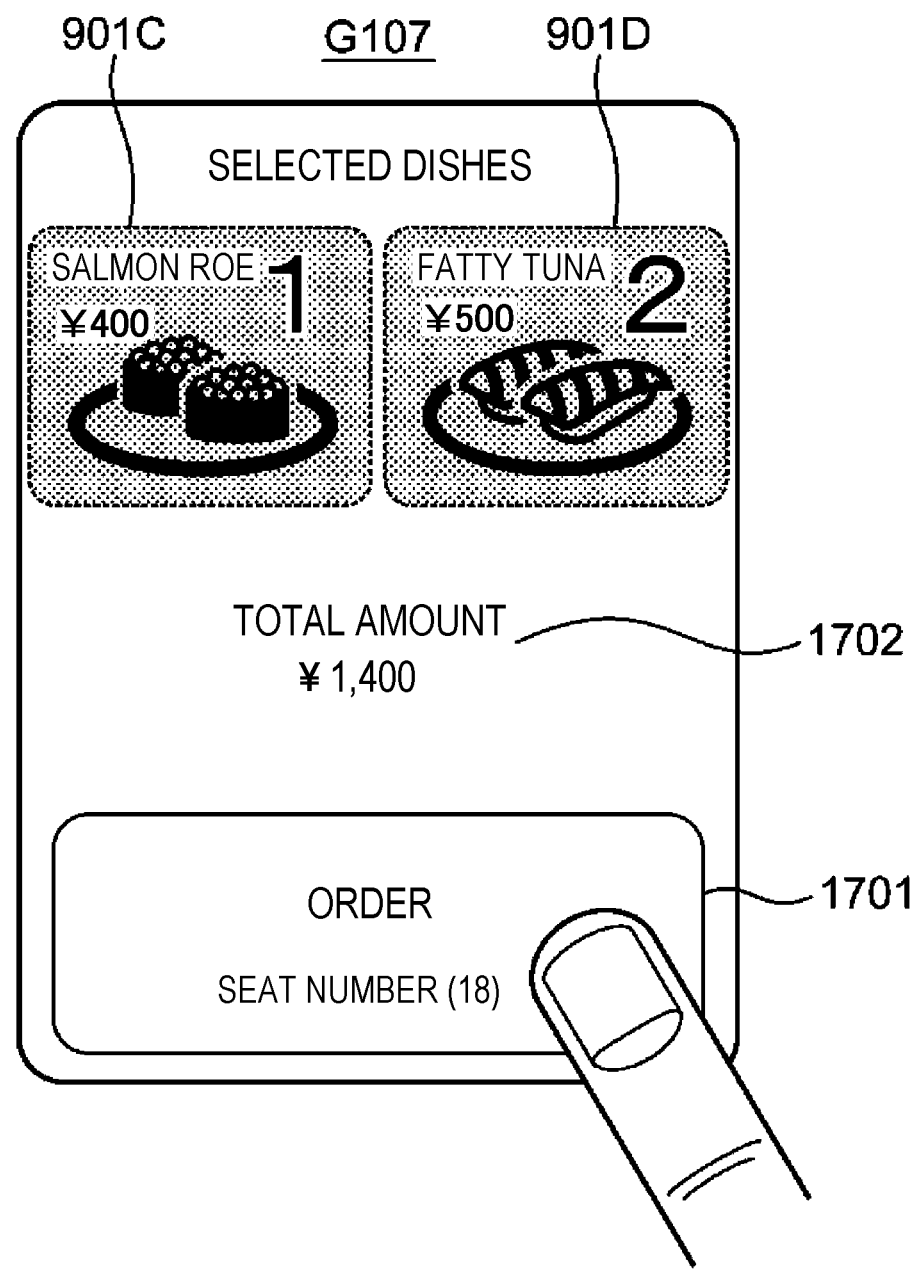
FIG. 19 is a diagram showing an example of an operation screen which is displayed when a dish is selected from a personalized menu and the selected dish is finally determined to be ordered.

When the matching application accepts a dish order via the operation screen G106, the matching application sends an order request including the ordered-dish information and the seat ID associated with each other to the second server 300. FIG. 19 is a diagram showing an example of an operation screen which is displayed when a dish is selected from a personalized menu and the selected dish is finally determined to be ordered. The operation screen G107 is displayed when the order button (not shown in FIG. 18) on the operation screen G106 is touched by the user order the dishes.

The operation screen G107 includes the tile objects 901C and 901D corresponding to the dishes selected on the operation screen G106 and the total amount field 1702 indicating the total amount (\1,400) of the ordered dishes (one dish of salmon roe and 2 dishes of fatty tuna). The operation screen G107 further includes an order button 1701. The content of this operation screen G107 is the same as that of the operation screen G4 in the standard menu. When the order button 1701 is touched, an order request including the ordered-dish information and the seat ID associated with each other is sent to the second server 300 of the restaurant company A. The order request is displayed on a display installed in the store of the restaurant company A. Thus, a restaurant staff can grasp the order content from the displayed seat number "18" and the ordered-dish information, and start cooking and serve the ordered dishes to the seat number "18".

FIG. 20 is a diagram showing an example of an order history screen which is displayed in response to a request for seeing an order history issued by a user. The order history screen G108 includes an in-preparation frame 1801 displayed on the left side of the screen and a served-dish frame area 1802 displayed on the right side of the screen. Inside the in-preparation frame 1801, tile objects 901 indicating dishes that are ordered and are now in preparation are arranged. Inside the served-dish frame 1802, tile objects 901 indicating the served dishes are arranged. In the specific example shown in FIG. 20, no dishes have been served yet, and thus no tile objects 901 are displayed in the served-dish frame 1802. Currently, two dishes of fatty tuna and one dish of salmon roe are in preparation, and thus tile objects 901 of fatty tuna and salmon roe are arranged in the in-preparation frame 1801. On the order history screen G108, the total amount (\1,400) of the dishes ordered in the past via the matching application is displayed in an easy-to-understand manner at the bottom of the screen. By checking the order history screen G108, the user can see at a glance the dishes ordered so far, the quantity, and the payment amount. An "order history" button (not shown) may be provided on the operation screen G106, and the order history screen G108 may be displayed when the "order history" button is touched.

The processing on the order via the personalized menu at the restaurant company A is performed as described above. When a user wants to order a dish, the user can acquire a personalized menu prepared taking into account the allergy information of the user simply by operating the information terminal 100 to read a QR code assigned to a seat of the user in the restaurant using the matching application provided by the first server 200, and the user can select a dish from the personalized menu to order it. This is an unprecedented, easy, and unmistakable way to order personalized dishes.

To make it possible to execute the order process, it is sufficient that the user installs the matching application on the information terminal 100 in advance.

Furthermore, the user may capture an image of a diagnosis table indicating a result of an allergy test diagnosed in a hospital and may share the image of the diagnosis table with the matching application, or may make a setting to allow the image of the diagnosis table to be accessed. The first server 200 may mechanically read the described information from the image of the shared diagnosis table and register it as allergy information.

Alternatively, the user may permit in advance the matching application or the development company or operating company of the matching application to share the allergy test result and related information about the allergy diagnosis issued by the hospital. In this case, when the matching application shares a new diagnosis result made by the hospital, the matching application adds the new diagnosis result to the first server 200. Thus, it becomes possible for the matching application to use the diagnostic result added to the matching in matching with a new product or service.

Alternatively, the user may permit that the allergy test results and related information issued by the hospital that performed the allergy diagnosis are stored in association with the user ID in the first server 200. In this case, the hospital may request that a new diagnosis result is stored in the first server 200. Thus, it becomes possible for the matching application to use the stored diagnostic result in matching with a new product or service.

The allergy information related to the user may be registered and stored in the information terminal 100 by the user himself/herself. In a case where the data is small in data size and no change occurs in the data with time, the user can input allergy information in the information terminal 100 by himself/herself. However, in a case where the data size of the allergy information is large and updating of the data frequently occurs, the operation of inputting data is troublesome, which may make it difficult for the user to correctly register the allergy information in the first server 200 each time updating occurs. In contrast, in the method described above, even in a case where the data size of the allergy information is large and updating of the allergy information occurs frequently, it is possible to correctly store the allergy information whenever updating occurs.

Data Structure

Next, a data structure of allergy information and ingredient information 2800 is described below. FIG. 21 is a diagram showing an example of a data structure of information 2700 including allergy information related to a user which is returned from the first server 200 to the matching application. In this information 2700, fields and values are described in association with each other such that a computational process can be easily performed. One file of information 2700 is configured in a format such as JSON (JavaScript (registered trademark) Object Notation).

A field of "information category" is a field indicating what kind of personal information the information 2700 is. In this specific example, the information 2700 is about healthcare and thus "healthcare" is stored as the value in the information category field. The "information category" field is located at the beginning of the information 2700.

An "issuer" field is a field for identifying an institution, a legal entity, or an individual who issued this information 2700. In this specific example, the information 2700 was issued by ABC clinic, and thus ABC clinic is described as the value in the "issuer" field.

A "date of issue" field is a field for indicating a date and time of issue made by the issuer of this information 2700. In this example, Dec. 1, 2019 is described as the value in the "date of issue" field. The value in this field may include a time of issue in addition to the date of issue. The value in this field may further include time zone information.

A "data type" field is a field for specifically identifying a content of this information 2700. In this specific example, allergy test result [IU/mL] is described by way of example as the value in the "data type" field. This indicates that data described in following fields are data related to a result of test in terms of allergic reactions of the user. In this example, allergic reaction levels are expressed by non-specific IgE levels in units of IU/mL.

The information terminal 100 may interpret that the information 2700 includes allergy information based on values described in the respective fields of "information category" and "data type". Alternatively, the information terminal 100 may interpret that the information 2700 includes allergy information based on the information related to the information 2700 (for example, the file name of the information 2700).

A "date of test" field is a field indicating the date and time of measuring the values of "allergy test results" corresponding to the preceding "data type" field was measured. In this example, Nov. 14, 2019 is described as the value in the "date of test" field. This value may include data of a time of test in addition to the data of date of test. The value in this field may further include time zone information.

An "egg" field is a field that indicates the allergic reaction level to eggs. In this specific example, 25.40 (in units of IU/mL) indicating the allergic reaction level of the user to eggs is described in the "egg" field. In the following fields, results of tests on allergic reactions to various allergens such as "milk", "wheat", "peanut", "shrimp", "crab", and "tuna" are described in similar manners to the case of eggs.

According to the setting of the non-specific IgE by immunocap, allergic reaction levels up to 0.34 IU/mL are classified into class 0 (negative), allergic reaction level from 0.34 IU/mL to 0.70 IU/mL are classified into class 1 (false positive), allergic reaction level from 0.70 IU/mL to 3.5 IU/mL are classified into class 2 (positive), allergic reaction level from 3.5 IU/mL to 17.5 IU/mL are classified into class 3 (positive), allergic reaction level from 17.5 IU/mL to 50 IU/mL are classified into class 4 (positive), allergic reaction level from 50 IU/mL to 100 IU/mL are classified into class 5 (positive), and allergic reaction level higher than 100 IU/mL are classified into class 6 (positive).

In the example shown in FIG. 21, egg belongs to the class 4 (positive), and shrimp and crab belong to the class 6 (positive). In the personalized menu shown in FIG. 17, "spot shrimp" and "egg" included in the standard menu are removed because it is determined that allergic reactions thereto are so strong that it is harmful to health.

To identify dishes that may cause allergic reactions, it is necessary that the menu information acquired from the second server 300 of the restaurant company A includes the ingredient information for each dish. FIG. 22 is a diagram showing an example of a data structure of the ingredient information 2800 constituting the menu information returned from the second server.

In the ingredient information 2800, fields and values are described in association with each other such that a computational process can be easily performed. The ingredient information 2800 is embedded together with a tag indicating the ingredient information in the menu information described in, for example, an HTML file format, which is acquired from the second server 300 of each restaurant company. However, this is merely an example, and the ingredient information 2800 may be given by a separate file described in a JSON format and prepared for each dish.

A "dish name" field is a field indicating a dish about which the present information describes. In this example, the ingredient information 2800 is ingredient information about 2 pieces of spot shrimp, and thus spot shrimp (two pieces) is described as the value in the "dish name" field.

In the following fields and values, a list of ingredients used is described. For example, a "spot shrimp" field is a field indicating that spot shrimp is used as an ingredient in this dish. In a value field corresponding to the "spot shrimp" field, 20 g is described to indicate the amount of spot shrimp used in this dish. In the example shown in FIG. 21, the information 2700 indicates that the allergic reaction to shrimp is in the strong class 6, that is, the allergic reaction to shrimp is strong. Therefore, "spot shrimp (2 pieces)" is excluded from the personalized menu shown in FIG. 17.

The matching application may recognize that the "spot shrimp" described in the ingredient information 2800 corresponds to the "shrimp" described in the "allergy test result" field of the information 2700, for example, by referring to a dictionary registered in connection with the matching application. Alternatively, the matching application may acquire a public information source such as Wikipedia from, for example, the public information server 500, and may determine that the spot shrimp is one type of shrimp based on the acquired public information source.

FIG. 23 is a diagram showing another example of a data structure of the ingredient information 2800 constituting the menu information returned from the second server 300. In the ingredient information 2800 in this example, ingredient information of sauce ramen is described. Therefore, "soy sauce ramen" is described as a value of the "dish name" field. Furthermore, in this ingredient information 2800, ingredients of the soy sauce ramen and amounts of the respective ingredients thereof are described in association with each other, such as: wheat flour, 50 g; salt, 5 g; and so on. The ingredient information 2800 of soy sauce ramen does not include ingredients that are described, in the information 2700, as being positive in the allergic reaction test result. Therefore, soy sauce ramen is included, as an alternative dish in the personalized menu shown in FIG. 17.

Overall View of Process

Figure 24:
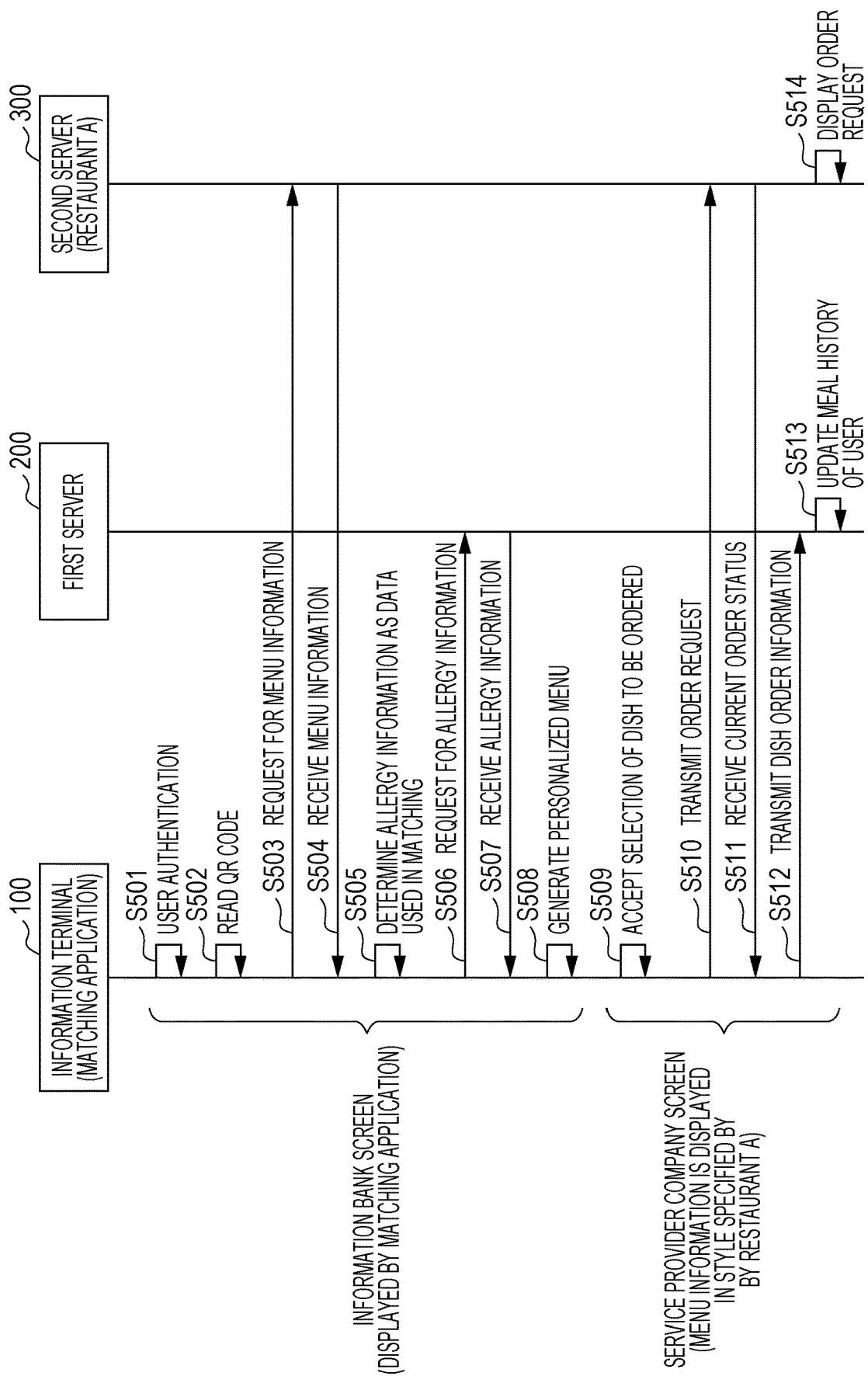
FIG. 24 is a sequence diagram showing an example of an overall view of a process performed by an information processing system according to an embodiment.

Next, an overall view of the process performed in the information processing system according to the present embodiment is described below. FIG. 24 is a sequence diagram showing an example of an overall view of the process performed in the information processing system according to the present embodiment.

After a user enters a store of the restaurant company A and is seated in a seat, if the user starts the matching application by operating the information terminal 100, the matching application performs user authentication (step S501). If the user authentication is passed successfully, the matching application displays the home screen G103 (see FIG. 14).

When the user touches the scan button 1402 on the home screen G103, the matching application activates the scan function and acquires a QR code corresponding to the seat of the user (step S502). As a result, the matching application acquires the URL of the second server 300 (HTTP server) of the restaurant company A to which the connection is to be made.

After the matching application acquires the URL, the matching application transmits a request for acquiring the menu information (for example, an HTTP request) to the second server 300 of the restaurant company A based on the URL (step S503). In this step, as described above, the matching application may transmit the seat ID included in the QR code to the second server 300.

In response to receiving this request, the second server 300 transmits an HTTP response thereby returning the menu information by using the HTTP server function. The matching application receives the menu information of the restaurant company A (step S504).

When the matching application receives the menu information, the matching application analyzes the received menu information. In this case, it is detected as a result of the analysis that the data attribute of the received menu information is the food attribute. More specifically, for example, the matching application may detect the food attribute by analyzing the contents of the menu information. Alternatively, the matching application may detect the food attribute from supplementary information transmitted separately from the menu information. When the matching application detects that the data attribute of the received menu information is the food attribute, the matching application determines that the allergy information is to be used as the data for matching (step S505).

Next, to request for providing the allergy information of this user who has passed the authentication successfully, the matching application transmits an HTTP request to the first server 200 based on the user ID of the user (step S506). When the first server 200 receives this HTTP request using a function of the HTTP server, the first server 200 extracts the allergy information related to the user based on the user ID from the memory 203, and returns, as an HTTP response, the extracted allergy information to the matching application. Thus, the matching application receives this allergy information related to the user (step S507).

When the matching application receives the allergy information, the matching application generates a personalized menu, based on the received menu information and the received allergy information, so as to be suitable for the user having allergies described in the received allergy information by using one of the above-described three methods (step S508).

The matching application generates various screen style UI (User Interface) designs displayed in the process from step S501 to step S508 according to the styles of the matching application. However, the styles (for example, UI designs) specified by the restaurant company A are employed when the matching application generates various screens staring from the screen for the personalized menu ending to the screen for use in the dish order. In other words, although each service providing company (for example, each restaurant) uses the matching application provided by another company (for example, an information bank or an information intermediary), the service providing company can communicate with users (for example, customers) in a specific style (for example, a UI design) the service providing company wants to use. This means that the above-described standard menu and the personalized menu can both be expressed in the style (for example, a UI design) specified by the restaurant company A while maintaining consistency.

After the matching application generates the personalized menu, the matching application displays the operation screen G106 including the generated personalized menu in the style specified by the restaurant company A, and accepts a selection instruction which is issued by the user to order a dish from the personalized menu (step S509).

When the matching application receives the selection instruction, the matching application transmits an order request including the seat ID of the user and the ordered-dish information indicating the dish to be ordered in association with each other to the second server 300 of the restaurant company A (step S510). In response to receiving the order request, the second server 300 returns a response confirmation (ACK) indicating that the order has been received to the matching application and also, as necessary, the current order status (for example, information about the order history screen G108). Thus, the matching application receives the current order status (step S511). The matching application displays the received current order status on the display 105.

The matching application transmits the ordered-dish information in association with the user ID to the first server 200 (step S512), and requests the first server 200 to add it to the meal history information related to the user or update the meal history information. In response to receiving the ordered-dish information, the first server 200 updates the meal history information related to the user according to the received ordered-dish information (step S513). In this update step, a time stamp indicating the time of ordering the dish indicated by the ordered-dish information is also added to the meal history information.

Upon receiving the order request, the second server 300 of the restaurant company A displays the order request on the display in the store (step S514). This allows an employee of the store to correctly serve the ordered dish to the user in the seat who ordered the dish.

In this way, the meal history information, which is part of the user's personal information, is accumulated in the first server 200 in a fine, accurate, and time-serial manner. This makes it possible to use this big data when a dish is ordered for the next time, which allows it present highly suitable dish options to the user with higher accuracy.

According to the control method shown in FIG. 24, it is possible to reduce the risk of erroneously serving, to the user, a dish which is different from the dish ordered by the user and is not suitably prepared in terms of allergy. Furthermore, according to the control method shown in FIG. 24, even for a user for whom it is necessary to make a detailed confirmation of ingredients, cooking method, etc. from the point of view of allergies, the user is allowed to easily order a dish without having a restaurant perform such confirmation, and the restaurant can easily handle the dish order from such a user. Furthermore, according to the control method shown in FIG. 24, it is possible to reduce the risk that a restaurant staff gets to know personal information related to the user's privacy such as allergy information, and the risk that the user's personal information related to the privacy is accumulated in the store terminal.

Furthermore, according to the control method shown in FIG. 24, it is possible to effectively and safely manage personal information including accurate and temporally continuous allergy information, meal history information (for example, order history information), activity amount, vital sign information, and/or the like. Furthermore, according to the control method shown in FIG. 24, it is possible to prevent the personal information from being leaked to anyone other than the company to which permission is given by the user.

Flowchart of Order Process

Next, a process performed by the information terminal 100 according to the present embodiment is described below. FIG. 25 is a flowchart showing an example of a process which is performed by the information terminal 100 when a dish is ordered from the standard menu. The process shown in this flowchart is started when the user activates the QR code reader on the information terminal 100.

In step S11, the QR code reader reads a QR code and transfers a read text string (for example, a URL) to the browser. In this process, the QR code is read via the operation screen G1 shown in FIG. 7, and the reading result of the QR code such as that shown in FIG. 8 is displayed on the operation screen G2.

In step S12, the browser accesses the second server 300 of the restaurant company A according to the URL, acquires the standard menu information, and displays the standard menu on the display 105 of the information terminal 100. In this process, the operation screen G3 including the standard menu such as that shown in FIG. 9 is displayed.

In step S13, the browser accepts an instruction from the user to select a dish to order from the standard menu. In this step, the user operates the standard menu included in the operation screen G3 shown in FIG. 10 to select the dish to be ordered.

In step S14, the browser transmits an order request including the user's seat ID and the ordered-dish information indicating the dish ordered by the user in association with each other to the second server 300 of the restaurant company A. Thus, the order process via the standard menu is completed.

As described above, when a user wants to order, in a restaurant, a dish to be prepared properly taking into account the allergy information of the user, the user displays a personalized menu using the matching application and orders the dish from the personalized menu. On the other hand, a user, who wants to select a dish from the standard menu provided in the restaurant without considering his/her allergy information, displays the standard menu using a general-purpose QR code reader and orders the dish.

In each case, the seat ID read from the QR code corresponding to the seat in which the user is seated is sent together with the ordered-dish information to the second server 300, and thus the ordered dish is correctly served.

FIG. 26 is a flowchart showing an example of a process which is performed by the information terminal when a dish is selected from a personalized menu and ordered. The process shown in this flowchart is started when a user activates the matching application to order a dish at a restaurant.

In step S1, the matching application executes a process of acquiring a QR code corresponding to a seat of the user. Details of this process are described later with reference to FIG. 27. In this process, the QR code is read via the operation screen G104 shown in FIG. 15, and the seat ID and restaurant ID are acquired. This process corresponds to steps S501 and S502 in FIG. 24.

In step S2, the matching application accesses a URL indicated by the acquired QR code by using a browser function, and executes a process of acquiring menu information of the restaurant company A from the second server 300 of the restaurant company A. Details of this process will be described later with reference to FIG. 28. In this process, it is also detected that the data attribute of the menu information is the food attribute. In this process, the display screen G105 shown in FIG. 16 is displayed on the information terminal 100. This process corresponds to steps S503 and S504 in FIG. 24.

In step S3, the matching application executes a process of acquiring allergy information, which is personal information related to the food attribute, from the user's personal information from the first server 200. Details of this process will be described later with reference to FIG. 29. Via this process, allergy information is acquired which is related to the user seated in the seat indicated by the seat ID acquired in step S1. This process corresponds to steps S505, S506, S507 in FIG. 24.

In step S4, the matching application executes a process of checking the menu information of the restaurant company A based on the allergy information related to the user, and generating a personalized menu including only allergen-controlled dishes. As a result of this process, the operation screen G106 including the personalized menu is displayed. This process corresponds to step S508 in FIG. 24.

In step S5, the matching application accepts an instruction issued by the user to select a dish to be ordered from the personalized menu. More specifically, for example, a dish is selected via the operation screen G106 shown in FIG. 18. This process corresponds to step S509 in FIG. 24.

In step S6, the matching application transmits, to the second server 300 of the restaurant company A, an order request including the ordered-dish information indicating the dish selected in step S5 and, in association with it, the seat ID acquired in step S1. This process corresponds to step S510 in FIG. 24.

Figure 27:
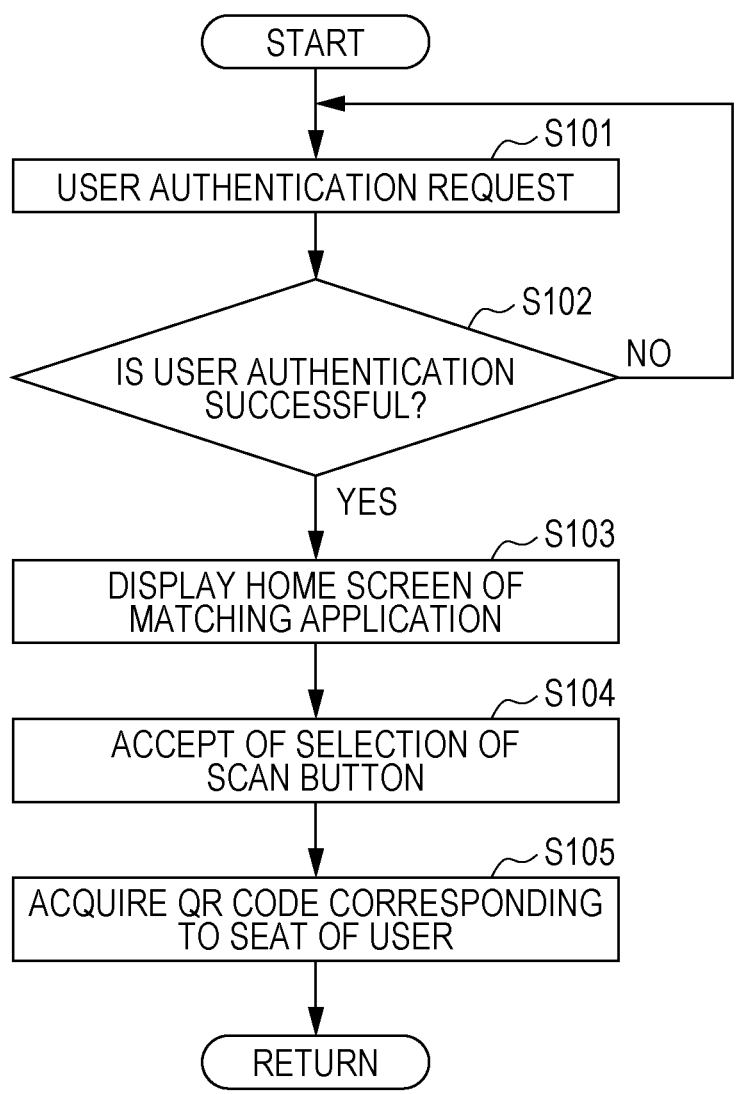
FIG. 27 is a flowchart showing details of a process in step S1 in FIG. 26.

The process of ordering a dish from the personalized menu is described in further detail below. FIG. 27 is a flowchart showing the details of the process in step S1 in FIG. 26. In step S101, when the matching application is activated by the user, the matching application prompts the user to perform an authentication process. More specifically, for example, the user authentication process is performed via the authentication screen G101 shown in FIG. 12 or the authentication screen G102 shown in FIG. 13.

In step S102, the matching application determines whether or not the user has been successfully authenticated. In a case where the user authentication fails (NO in step S102), the process returns to step S101. When the user authentication is successful (YES in step S102), the process proceeds to step S103. In step S103, the matching application displays the home screen G103 of the matching application as shown in FIG. 14.

In step S104, when the matching application accepts a user operation of touching the scan button 1402 on the home screen G103, the matching application activates the QR code reading function. As a result, the operation screen G104 shown in FIG. 15 is displayed.

In step S105, the orientation and the position of the information terminal 100 are adjusted by the user, and the matching application reads the QR code corresponding to the seat in which the user is seated.

Figure 28:
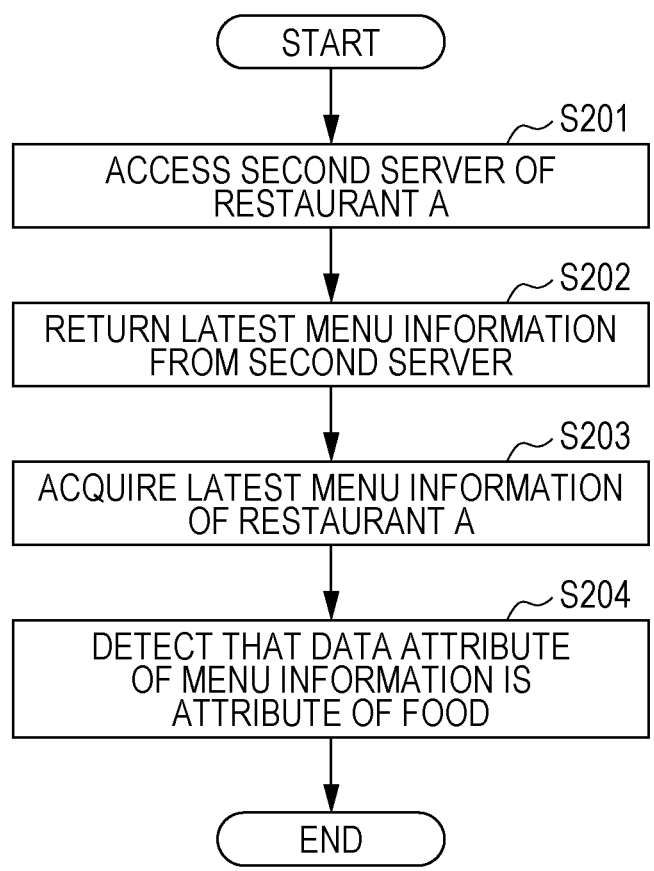
FIG. 28 is a flowchart showing details of a process in step S2 in FIG. 26.

FIG. 28 is a flowchart showing the details of the process in step S2 in FIG. 26. In step S201, the matching application accesses the second server 300 of the restaurant company A based on a character string (for example, a URL) described in the QR code. This access is performed, for example, by an HTTP request.

In step S202, the second server 300 of the restaurant company A returns the latest menu information to the matching application by using the HTTP server function. This response is given, for example, by an HTTP response.

In step S203, the matching application acquires the latest menu information of the restaurant company A.

In step S204, the matching application detects, from the acquired menu information, that the data attribute of the menu information is the food attribute. This detection is performed, for example, based on the data attribute described in an HTML file of the menu information.

Figure 29:
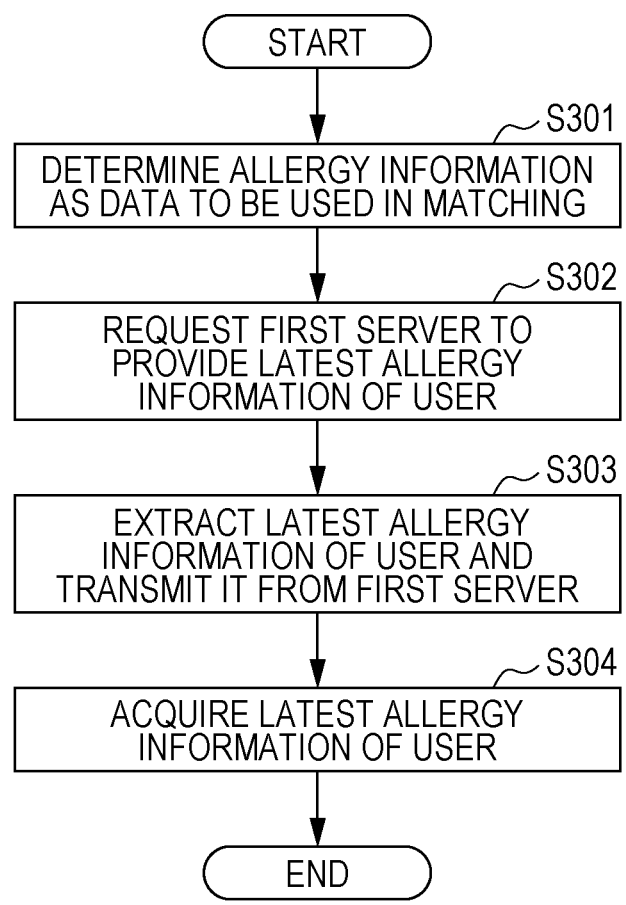
FIG. 29 is a flowchart showing details of a process in step S3 in FIG. 26.

FIG. 29 is a flowchart showing the details of the process in step S3 in FIG. 26. In step S301, since the data attribute of the acquired menu information is the food attribute, the matching application determines that the allergy information related to the user is to be used as data for matching.

In step S302, the matching application requests the first server 200 to provide the latest allergy information related to the user to be matched. More specifically, the matching application specifies the user ID and requests that the allergy information is returned in a predetermined encrypted form.

In step S303, the first server 200 extracts the latest allergy information based on the user ID from a huge amount of personal information managed in a distributed and encrypted manner. The first server 200 forms the extracted allergy information into a predetermined format, encrypts into a predetermined format, and returns the result to the matching application.

In step S304, the matching application decodes the acquired latest allergy information. As a result, the latest allergy information related to the user is acquired.

Figure 30:
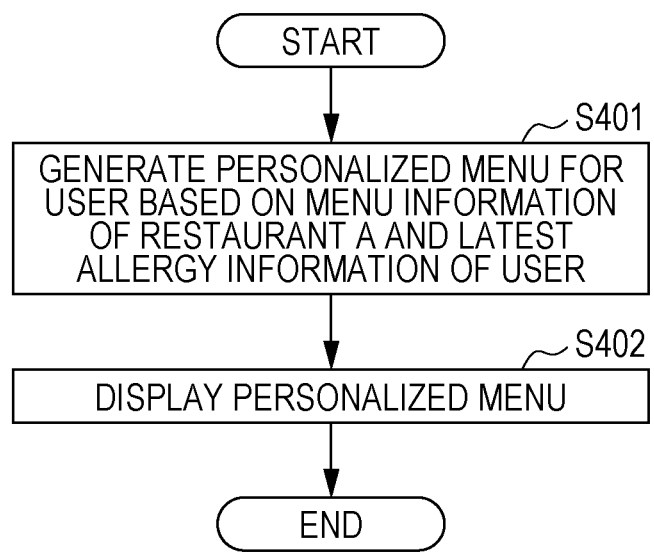
FIG. 30 is a flowchart showing details of a process in step S4 in FIG. 26.

FIG. 30 is a flowchart showing the details of the process in step S4 in FIG. 26. In step S401, the matching application checks the menu information of the restaurant company A and the latest allergy information related to the user, and generates a personalized menu including only allergen-controlled dishes personalized for the user. The menu information includes, as described later, one or more ingredients and the amount thereof included in each dish. The menu information may include cooking method information indicating a cooking method of each dish. In this process, the personalized menu is generated using one of the three methods described above.

In step S402, the matching application generates the operation screen G106 including the generated personalized menu and displays it on the display 105 of the information terminal 100 using the browser function. More specifically, for example, the personalized menu is displayed in a style specified by the display style information included in the menu information of the restaurant company A. Examples of implementations of information process performed when dish is ordered via personalized menu Next, examples of implementations of the information process are described below, which are performed in a situation in which a dish is selected from a personalized menu and ordered. If an interface of information communication and a data structure of data handled thereby are unique to a specific restaurant store, this may result in a problem that various kinds of data handled in the information processing system can be used only in the specific store, for example, in the store 40 of the restaurant company A, but cannot be used in other restaurants such as restaurants of the restaurant company B, or a situation may occur in which they cannot be used not only in restaurants of the restaurant company B but even in stores of the restaurant company A other than the store 40. In order to avoid such a situation, a general solution is described below for many users to order dishes using personalized menus in many restaurants.

Figure 31:
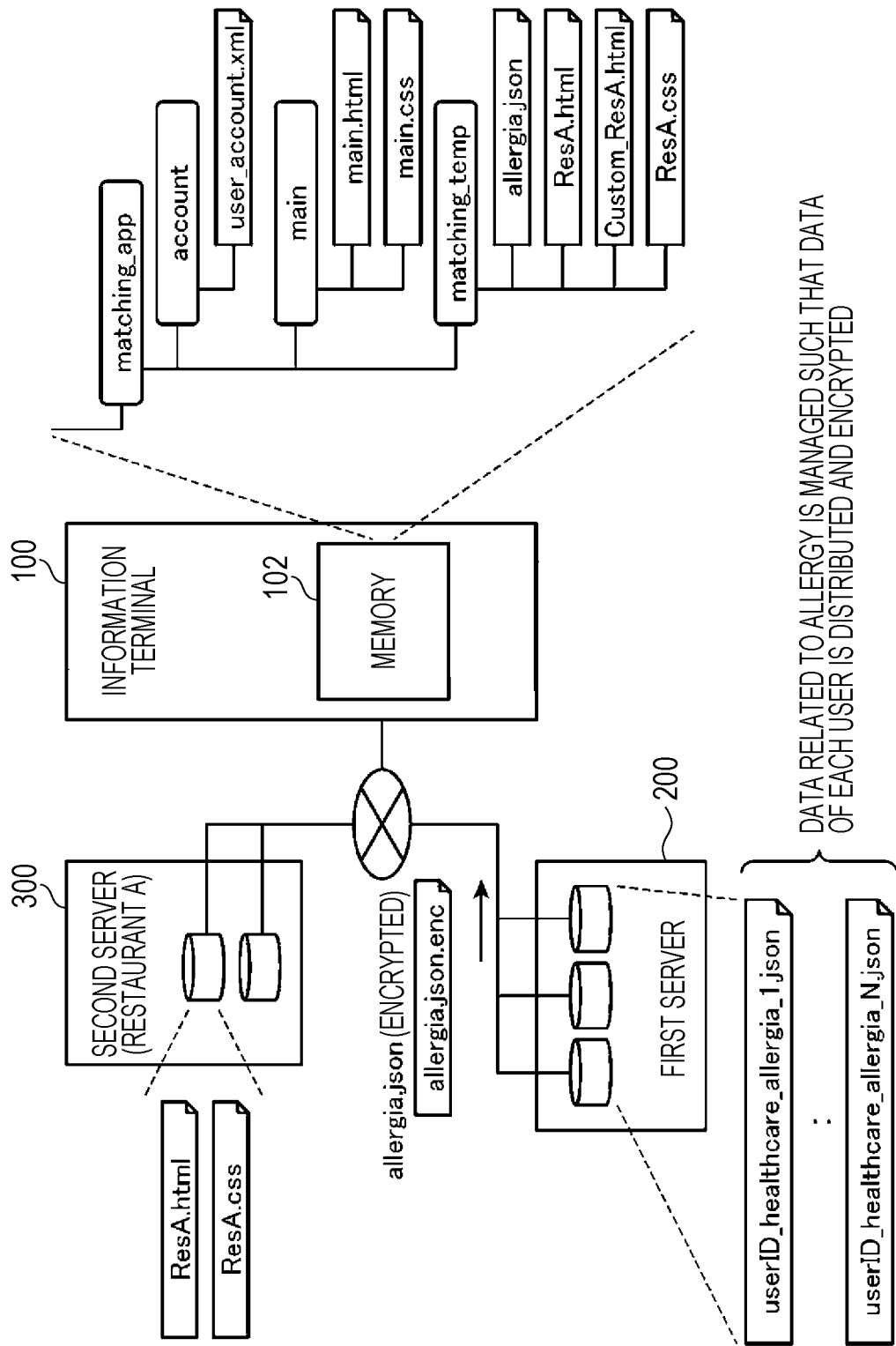
FIG. 31 is a diagram showing an example of a specific implementation of an information processing system according to an embodiment.

FIG. 31 is a diagram showing an example of a specific implementation of the information processing system according to the present embodiment. The memory 102 of the information terminal 100 has a "matching_app" directory, which is a storage location for files required in executing the matching application. Under the "matching_app" directory, there are "account", "main", and "matching_temp" directories. The "account" directory provides a storage location for storing a user's account and/or information required in user authentication are stored. The "main" directory provides a storage location for storing information necessary for the matching application to realize basic functions such as drawing the home screen, scanning QR codes, and the like. The "matching_temp" directory provides a storage location for temporarily storing information required in matching.

The "account" directory provides a storage location for storing a "user_account.xml" file in which account information and/or information required in user authentication are described. More specifically, in the "user_account.xml"

file, information for identifying a user, such as a unique account name (for example, a user ID specified by the user) and authentication information related to the account name (for example, a password, a fingerprint feature value, and/or a face feature value), is stored in an encrypted form.

The account name is not limited to the user ID specified by the user, and other kinds of information may be used if they are capable of individually identifying users who use the matching application. For example, a serial code uniquely assigned to each matching application, such as that which is embedded in the matching application program or distributed together with the matching application, may be employed. The serial code uniquely assigned to each individual matching application is a serial code uniquely assigned to each information terminal 100 on which the matching application is installed. Alternatively, as the account name, a unique account name may be generated by the matching application based on a random number when the matching application is activated for the first time or the account name is registered for the first time, and the generated unique account name may be used. In this case, the matching application may automatically generate the account name after confirming with the first server 200 that the account name is not duplicated with an already registered account name.

By setting, as the account name, character string information that is meaningless when seen by a person such as that described above, it is possible to transmit personal information with higher confidentiality. The allergy information of the personal information shown in FIG. 31 is managed such that it is fragmented into a plurality of files as described later. The above-described account name may be used in a user ID part of a file name in each fragmented file. Alternatively, another piece of information may be paired one-to-one with each account name described above and may be used as part of a file name (for example, a user ID part) of each fragmented file.

The "main" directory provides a storage location for storing a "main.html" file in which content information necessary in realizing basic functions of the matching application is described, and a "main.css" file in which a style of a screen display (for example, a UI design) is described.

In the second server 300 of the restaurant company A, a group of files are stored in advance for use in returning a response when a URL (for example, http://restaurantA.com/QRorder-18) represented by a character string read by an QR code reader is accessed. This file group includes a "ResA.html" file in which content information to be returned is described, and a "ResA.css" file in which a style of a screen display (for example, a UI design) of the content information is described. For example, the ingredient information 2800 such as that shown in FIG. 22 or 23 may be included in the "ResA.html" file or it may be stored in an external file referred to by the "ResA.html" file.

In the first server 200, a wide variety of personal information of the user, having a huge data size, are accumulated in a distributed and encrypted manner. For example, the allergy information related to the user used in the present is fragmented into a total of N files in the JSON format including a "userID_healthcare_allergia_1.json" file, a "userID_healthcare_allergia_2.json" file, . . . , a "UserID_healthcare_allergia_N.json" files, and they are stored in physically different storage apparatuses in the first server 200. In the N files, "userID" at the beginning of a file name is identification information identifying a user related to the personal information of interest, "healthcare" following "userID" is identification information identifying an information category (for example, healthcare) described above with reference to FIG. 21, "allergia" following "healthcare" is identification information identifying a data type (for example, allergy test result ([IU/mL]) described above with reference to FIG. 21, and a number at the end of the file name is an identification number of a fragmented file.

When the first server 200 receives a request for allergy information related to a user together with an appropriate permission (for example, permission information), the first server 200 can correctly restore the data from these N files and convert it into a predetermined description format (.json) thereby obtaining an "allergia.json" file, and further encrypt this "allergia.json" file to an "allergia.json.enc" file and return the resultant "allergia.json.enc" file to the matching application.

Figure 32:
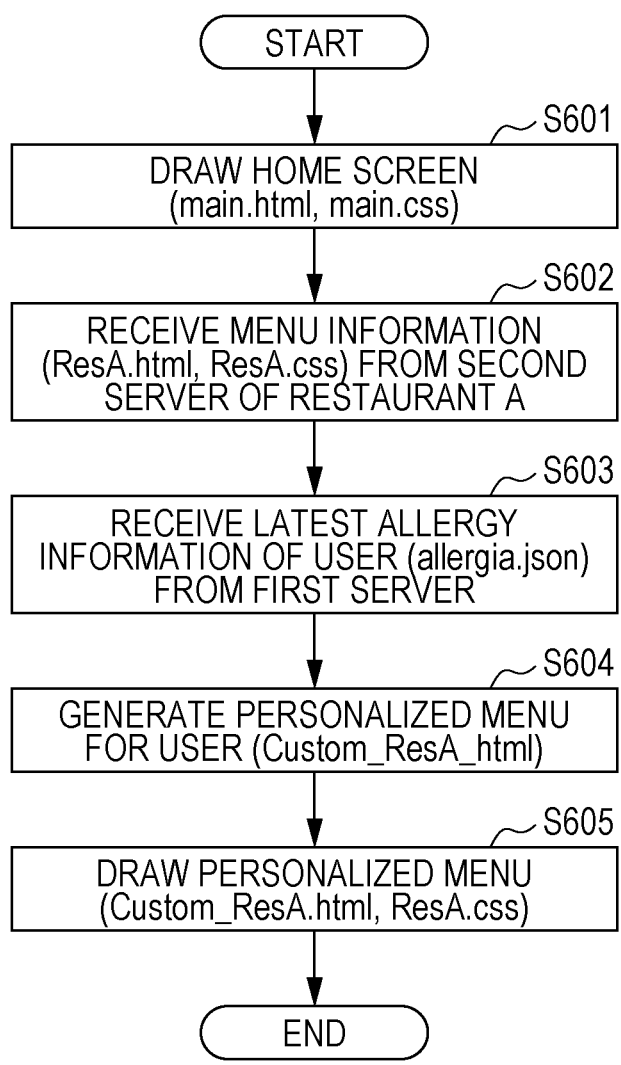
FIG. 32 is a flowchart showing an example of a process performed on a file by a matching application from starting of the matching application to displaying of a personalized menu.

Referring to a flowchart shown in FIG. 32, a description is given below as to handling of files in a situation in which the matching application controls the screen using HTML. FIG. 32 is a flowchart showing an example of a process performed on files by the matching application from the start of the matching application to displaying of a personalized menu.

In step S601, the matching application starts and draws the home screen. More specifically, immediately after the start, the matching application draws the home screen using the "main.html" file and the "main.css" file stored in the "main" directory. As a result, the home screen G103 shown in FIG. 14 is drawn.

In step S602, the matching application receives menu information from the second server 300 of the restaurant company A. The received menu information is stored as a "ResA.html" file and a "ResA.css" file in the "matching_temp" directory.

In step S603, the matching application receives encrypted allergy information related to a user (allergia.json.enc) from the first server 200. The received allergy information is decrypted by the matching application and stored as an "allergia.json" file in the "matching_temp" directory.

In step S604, the matching application generates a personalized menu according to the allergy information related to this user by editing the ResA.html file. The generated personalized menu is newly stored as a "Custom_ResA.html" file in the "matching_temp" directory. Thus, as shown in FIG. 31, the "allergia.json" file, the "ResA.html" file, the "Custom_ResA.html" file, and the "ResA.css" file are stored in the "matching_temp" directory.

In step S605, the matching application draws the generated personalized menu in the style specified by the restaurant company A using the "Custom_ResA.html" file and the "ResA.css" file.

Various screens are drawn using HTML/CSS files in the manner described above. Therefore, when a single matching application presents a product or service that matches the vast and diverse personal information of the user among products or services provided by an unspecified number of companies, it is possible to display information expected by a particular company in a style (for example, a UI design) expected by the company.

When ordering of a dish from a personalized menu by a user is completed and the display screen is returned to the home screen of the matching application, or when a predetermined time has passed since the order for the dish from the personalized menu is completed, all files temporarily stored in the "matching_temp" directory may be deleted for security.

Second Embodiment

In the first embodiment described above, the generation of the personalized menu is performed by the information terminal 100. In a second embodiment described below, the personalized menu is generated by the second server 300. In the following description of the second embodiment, the same constituent elements as those in the first embodiment are designated by the same reference numerals, and a further description thereof is omitted. The second server 300 constitutes an information management system. The information management system constitutes an information processing system.

First, a configuration of the second embodiment is described with reference to FIG. 4. In the second embodiment, personalized menus are generated by the second server 300, and thus the following description focuses on the configuration of the second server 300.

The computational processing unit 302 of the second server 300 acquires a user ID stored in the information terminal 100 from the information terminal 100 via a network.

The computational processing unit 302 acquires allergy information related to a user from the first server 200 via the network using the user ID. The allergy information includes information indicating an allergic reaction level of the user to each ingredient. The allergy information is transmitted from the first server 200 to the restaurant company A where the user entered or to the second server 300 when the permission to access the allergy information has been granted by the user to the restaurant company A or the second server 300. This makes it possible to prevent the user's private information from leaking to the outside of the first server 200 without permission from the user. On the other hand, if the permission to access the allergy information is not granted by the user to the restaurant company A where the user entered or the second server 300, the allergy information is not transmitted from the first server 200. In a case where the allergy information related to the user cannot be acquired, the second server 300 may send a standard menu of the restaurant company A to the information terminal 100.

The computational processing unit 302 generates, based on the menu information and the allergy information, a personalized menu for the user such that the menu is properly personalized according to the allergy information. Note that the menu information includes information indicating one or more ingredients contained in each dish and an amount of each ingredient.

The computational processing unit 302 identifies an ingredient that causes allergy by detecting an ingredient in the menu information that is equal to or larger than the criterion value in terms of the allergic reaction level. The personalized menu includes dishes which are included in the menu information and arranged so as to reduce or remove any ingredient that can cause the allergy.

The computational processing unit 302 transmits the personalized menu information indicating the personalized menu to the information terminal 100 via the communication unit 301. The computational processing unit 302 allows the user to select a dish based on the personalized menu on the information terminal 100.

Figure 33:
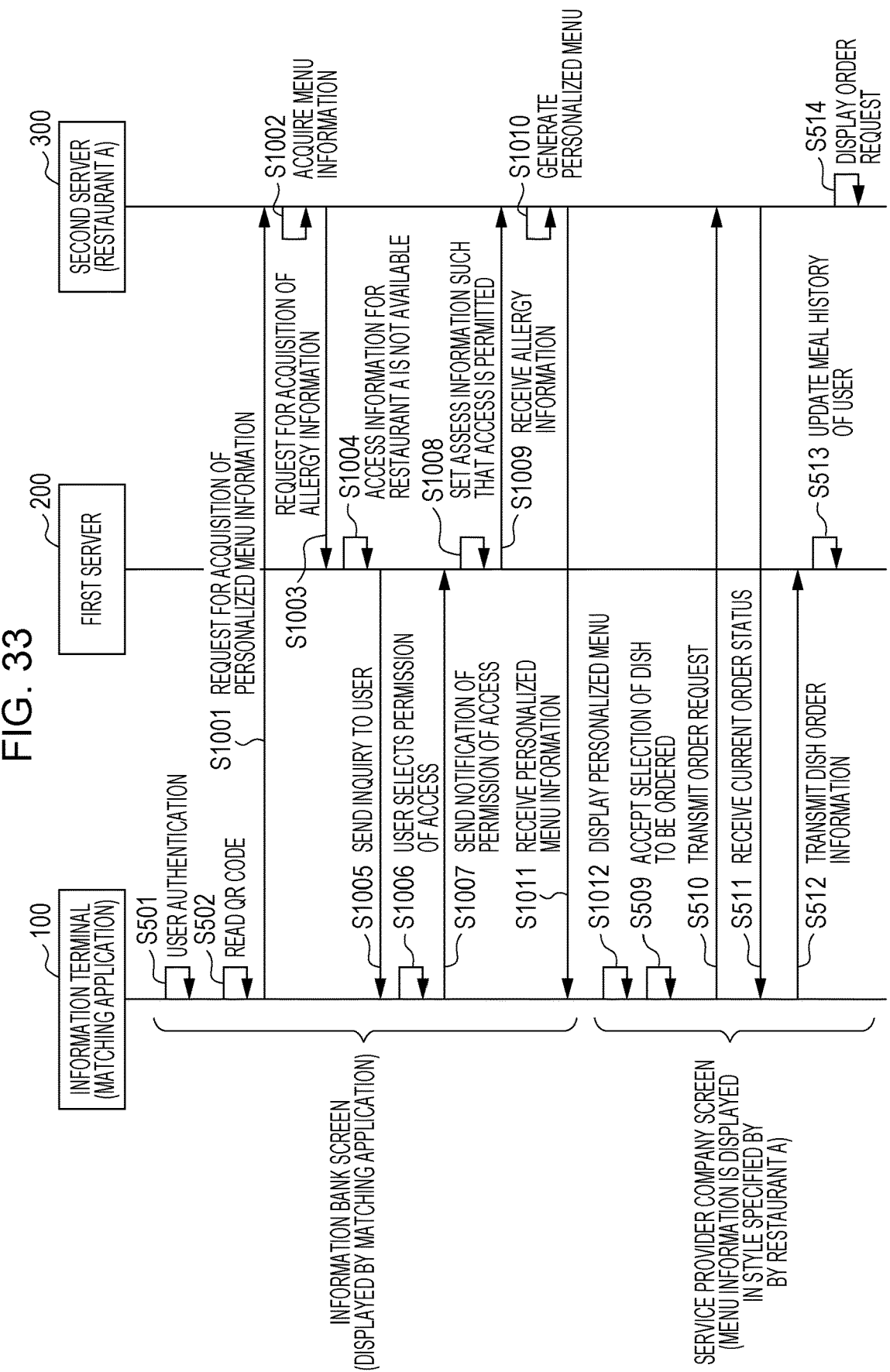
FIG. 33 is a sequence diagram showing an example of a process performed in an information processing system according to a second embodiment.

FIG. 33 is a sequence diagram showing an example of a process performed in the information processing system according to the second embodiment. In FIG. 33, the same processes as those in FIG. 24 are designated by the same process numbers, and a further description thereof is omitted. In FIG. 33, it is assumed that the user has not set the access information for the restaurant company A or the second server 300 in terms of the allergy information of the user.

Step S501 and step S502 are the same as those shown in FIG. 24.

In step S1001 following step S502, the information terminal 100 (the matching application) transmits a request for acquisition of personalized menu information to the second server 300. This acquisition request includes a store ID of a store of the restaurant company A where the user entered, a seat ID of a seat where the user was seated, and a user ID of the information terminal 100.

In step S1002, the second server 300 of the restaurant company A acquires the menu information of the restaurant company A from the memory 303.

In step S1003, the second server 300 transmits a request for acquisition of allergy information related to the corresponding user to the first server 200.

In step S1004, the first server 200 reads access information related to the corresponding user from the memory 203, and recognizes that the user has not set the access information for the restaurant company A or the second server 300.

In step S1005, the first server 200 sends an inquiry message to the information terminal 100 as to whether or not the restaurant company A or the second server 300 is allowed to access the allergy information. The inquiry message is displayed on the display 105 of the information terminal 100.

In step S1006, the information terminal 100 accepts an operation performed by the user, in response to reading the inquiry message, to select the access information such that the access is permitted.

In step S1007, the information terminal 100 transmits, to the first server 200, notification information indicating that the permission has been selected in setting of the access information.

In step S1008, in response to receiving the notification information indicating that the permission has been selected, the first server 200 sets the access information related to the user stored in the memory 203 to the access permission state. In the resultant state, the first server 200 is permitted by the user to read the allergy information related to the user from the memory 203 and transmit it to the second server 300 used by the restaurant company A.

In step S1009, the second server 300 receives the allergy information related to the corresponding user to from the first server 200.

In step S1010, the second server 300 generates a personalized menu for the user based on the allergy information related to the user. In this process, the personalized menu may be generated using the third method (based on the allergic reaction level) described above. The second server 300 transmits the personalized menu information indicating the generated personalized menu to the information terminal 100.

In step S1011, the information terminal 100 receives the personalized menu.

Various screens displayed in the processes in steps S501, S502, S1001 to S1011 are generated according to the style of the matching application. However, the screen of the personalized menu and other various screens displayed in the dish ordering process are generated according to a type specified by the restaurant company A.

When the information terminal 100 receives the personalized menu, the information terminal 100 displays the operation screen G106 including the personalized menu in the style specified by the restaurant company A (step S1012). Processes in step S509 and following steps are the same as those shown in FIG. 24.

Various screens displayed on the information terminal 100 in step S1012 and following steps may be those obtained by laying out materials (characters describing dishes, pictures of dishes, etc.) prepared by the restaurant company A according to a style specified by an administrator of the first server 200 (an information bank). This makes it possible to provide a unified user experience to users who use the matching application.

Figure 34:
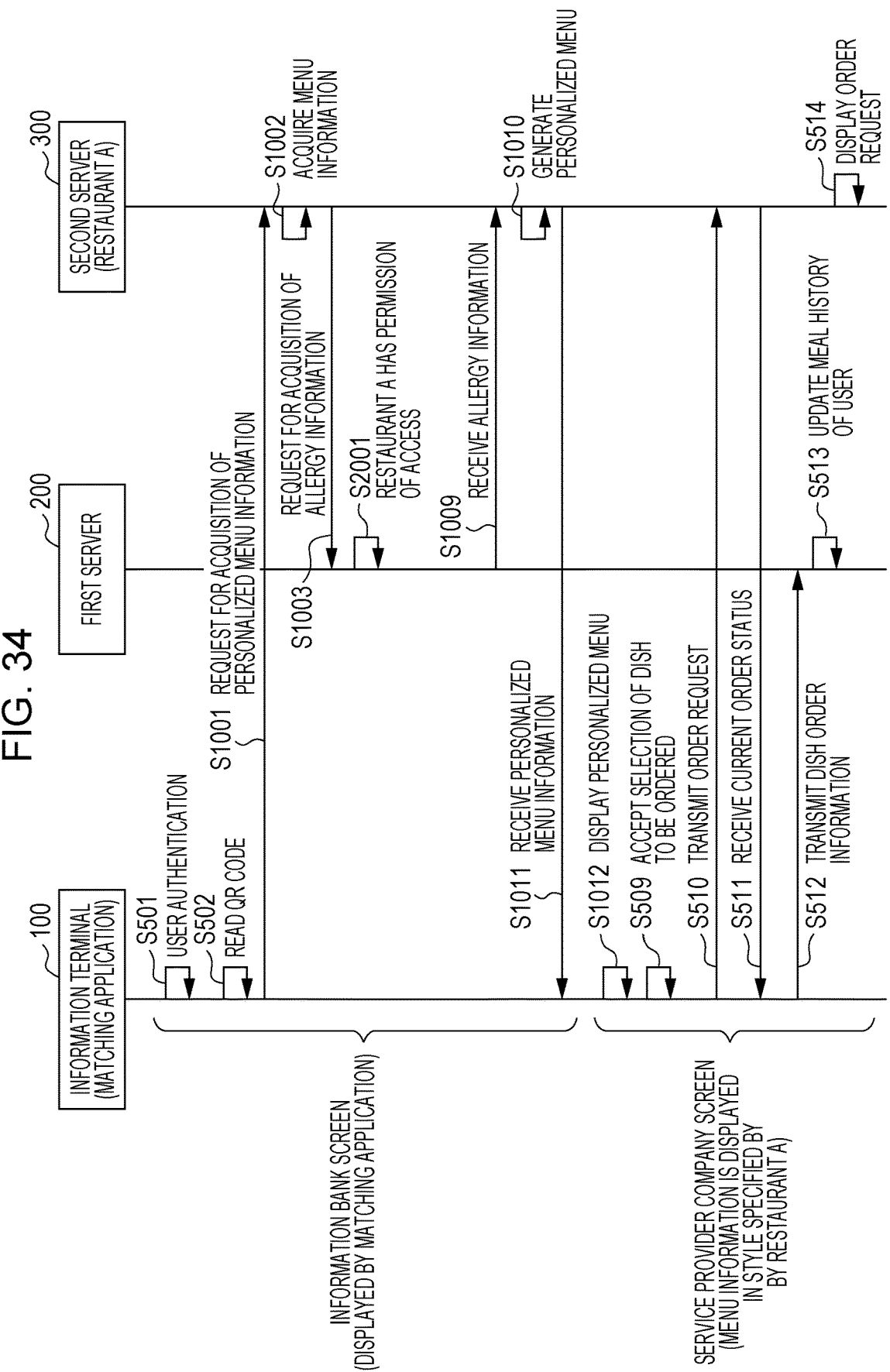
FIG. 34 is a sequence diagram showing an example of a process performed in the information processing system according to the second embodiment.

FIG. 34 is a sequence diagram showing an example of a process performed in the information processing system according to the second embodiment. In FIG. 34, the same processes as those in FIG. 33 are designated by the same process numbers, and a further description thereof is omitted. In FIG. 34, it is assumed that the user has set the access information such that the restaurant company A is permitted to access the allergy information related to the user.

Steps S501 and S502 and steps from S1001 to S1003 are the same as those shown in FIG. 33.

In step S2001 following step S1003, when the first server 200 receives a request for acquisition of allergy information related to the user, the first server 200 reads the access information related to the user from the memory 203, and confirms that the access information is set such that the restaurant company A or the second server 300 are permitted to access the allergy information related to the user. Upon confirming the setting state, the first server 200 reads the allergy information related to the user from the memory 203 and transmits it to the second server 300 used by the restaurant company A.

Processes in S1009 and following steps are the same as those shown in FIG. 33.

Figure 35:
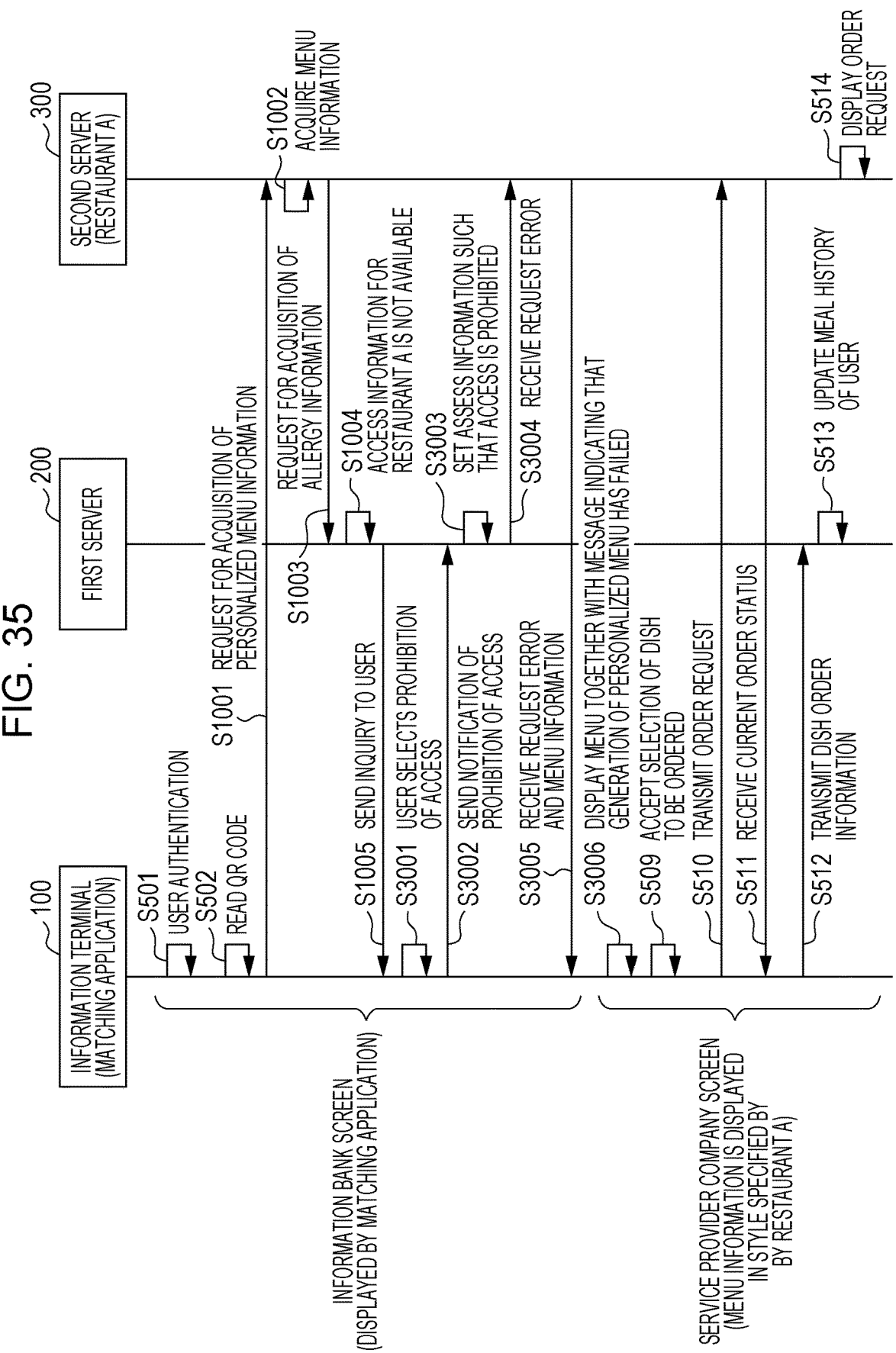
FIG. 35 is a sequence diagram showing an example of a process performed in the information processing system according to the second embodiment.

FIG. 35 is a sequence diagram showing an example of a process performed in the information processing system according to the second embodiment. In FIG. 35, the same processes as those in FIG. 33 are designated by the same process numbers, and a further description thereof is omitted. In FIG. 35, it is assumed that the user has not set the access information for the restaurant company A or the second server 300 in terms of the allergy information of the user.

Steps S501 and S502 and steps from S1001 to S1005 are the same as those shown in FIG. 33. In step S3001 following step S1005, the information terminal 100 accepts an operation performed by the user, in response to reading the inquiry message, to select the access information such that the access is prohibited.

In step S3002, the information terminal 100 transmits, to the first server 200, notification information indicating that the prohibition has been selected in setting of the access information.

In step S3003, in response to receiving the notification information indicating that the prohibition has been selected, the first server 200 sets the access information related to the user stored in the memory 203 such that the accessing by the restaurant company A and the second server 300 is prohibited. As a result, the first server 200 sends a request error to the second server 300. The request error is information for notifying the second server 300 that the request for acquisition of the allergy information related to the user cannot be responded.

In step S3004, the second server 300 receives the request error. Upon receiving the request error, the second server 300 reads the menu information of the restaurant company A or the store in which the user has entered from the memory 303, and transmits the read menu information and the request error to the information terminal 100.

In step S3005, the information terminal 100 receives the menu information and the request error.

In step S3006, the information terminal 100 displays on the display 105 the operation screen G106 including the information indicating that the personalized menu could not be generated and including the standard menu indicated by the menu information.

Processes in S509 and following steps are the same as those shown in FIG. 33.

In the second embodiment, as described above, when the second server 300 generates a personalized menu, a dish prepared properly taking into account the allergic reaction level of the user is presented to the user. Furthermore, in the second embodiment, the allergy information is transmitted to the second server 300 only when the user permits, and thus the user's personal information is prevented from being leaked to the outside of the first server 200 against the intention of the user.

Third Embodiment

In the second embodiment described above, the generation of the personalized menu is performed by the second server 300. In a third embodiment described below, the personalized menu is generated by the first server 200. In the following description of the third embodiment, the same constituent elements as those in the first or second embodiment are designated by the same reference numerals, and a further description thereof is omitted. The first server 200 constitutes an information management system. The information management system constitutes an information processing system.

First, a configuration of the third embodiment is described with reference to FIG. 4. In the third embodiment, personalized menus are generated by the first server 200, and thus the following description focuses on the configuration of the first server 200.

The computational processing unit 202 of the first server 200 outputs, using the communication unit 201, a request for acquisition of menu information to the second server 300 based on a request for a personalized menu for a user acquired from the information terminal 100 of the user via a network.

The computational processing unit 202 acquires a user ID stored in the information terminal 100 from the information terminal 100 via a network and the communication unit 201.

The computational processing unit 202 acquires menu information of the restaurant company A or a store in which the user has entered from the second server 300 via the communication unit 201.

The computational processing unit 202 generates a personalized menu for the user based on the menu information and allergy information related to the user corresponding to the user ID such that the personalized menu is properly arranged according to the allergy information. Note that the menu information includes information indicating one or more ingredients contained in each dish and an amount of each ingredient. The allergy information includes information indicating an allergic reaction level of the user to each ingredient.

The computational processing unit 202 identifies an ingredient that causes allergy by detecting an ingredient in the menu information that is equal to or larger than the criterion value in terms of the allergic reaction level. The personalized menu includes dishes which are included in the menu information and arranged so as to reduce or remove any ingredient that can cause the allergy.

The computational processing unit 202 transmits the personalized menu information indicating the generated personalized menu to the information terminal 100 via the communication unit 201. The computational processing unit 202 allows the user to select a dish based on the personalized menu on the information terminal 100.

FIG. 36 is a sequence diagram showing an example of a process performed in the information processing system according to the third embodiment. In FIG. 36, the same processes as those in FIG. 24 are designated by the same process numbers, and a further description thereof is omitted. In step S4001 following step S502, the information terminal 100 (the matching application) transmits a request for acquisition of personalized menu information to the first server 200. This acquisition request includes a store ID of a store of the restaurant company A where the user entered, a seat ID of a seat where the user was seated, and a user ID of the information terminal 100.

In step S4002, the first server 200 transmits a request for acquisition of menu information to the second server 300 of the restaurant company A based on a store ID of the store of the restaurant company A where the user entered. Upon receiving this acquisition request, the second server 300 acquires the menu information of the restaurant company A or the store in which the user has entered from the memory 303, and transmits the acquired menu information to the first server 200.

In step S4003, the first server 200 receives the menu information of the restaurant company A or the store in which the user has entered.

When the first server 200 receives the menu information, the first server 200 analyzes the received menu information. In this case, it is detected as a result of the analysis that the data attribute of the received menu information is the food attribute. More specifically, the first server 200 may analyze the contents of the menu information thereby detecting that the menu information has the food attribute. Alternatively, the first server 200 may detect the food attribute from supplementary information transmitted separately from the menu information. Since the data attribute of the received menu information is the food attribute, the first server 200 determines that the allergy information indicating allergy of the user to foods is to be used as data in matching, and the first server 200 acquires the allergy information related to the user corresponding to the user ID from the memory 203 (step S4004).

In step S4005, the first server 200 generates a personalized menu for the user based on the allergy information related to the user. In this specific example, the personalized menu is generated using the third method described above (the method based on the allergic reaction level). The first server 200 transmits the personalized menu information indicating the generated personalized menu to the information terminal 100.

In step S4006, the information terminal 100 receives the personalized menu information from the first server 200.

Various screens displayed in the processes in steps S501, S502, S4001 to S4006 are generated according to the style of the matching application. However, the screen of the personalized menu and other various screens displayed in the dish ordering process are generated according to a type specified by the restaurant company A.

Various screens displayed on the information terminal 100 in S1012 and following steps may be those obtained by laying out materials (characters explaining dishes, pictures of dishes, etc.) prepared by the restaurant company A according to a style specified by an administrator of the first server 200 (an information bank). This makes it possible to provide a unified user experience to users who use the matching application.

S1012 and S509 are the same as those shown in FIG. 33.

In step S4007 following step S509, when the information terminal 100 accepts the selection instruction, the information terminal 100 transmits to the first server 200 an order request including the seat ID of the user and the ordered-dish information indicating the dish to be ordered in association with each other.

In step S4008, the first server 200 transmits the order request to the second server 300.

In response to receiving the order request, the second server 300 returns to the first server 200 a response confirmation (ACK) indicating that the order has been received and also, as necessary, the current order status (for example, information about the order history screen G108). Thus, the first server 200 receives the response confirmation and the current order status (step 4009).

When the first server 200 receives the response confirmation and the current order status, the first server 200 transmits the current order status to the information terminal 100. The information terminal 100 receives the current order status and displays it (step S4010). Processes in S513 and S514 are the same as those shown in FIG. 33.

In the third embodiment, as described above, when the first server 200 generates a personalized menu, a dish prepared properly taking into account the allergic reaction level of the user is presented to the user. Furthermore, in the third embodiment, since the allergy information is not transmitted to the second server 300, it is possible to prevent the personal information of the user from leaking to the outside of the first server 200 against the intention of the user. Problems of the techniques disclosed in PTL 1 and PTL 2 from another viewpoint In a restaurant, when a dish with a suppressed allergen ingredient is provided to a customer who is allergic to this ingredient, it is necessary to provide this dish with the suppressed ingredient correctly to this customer. Herein, the dish with the suppressed allergen ingredient is, for example, a dish including no allergen ingredient or a dish including a reduced amount of allergen ingredient. Hereinafter, in a case where, when a dish is ordered by a customer having allergy, a dish is prepared for this customer such that the dish includes no allergen ingredient or a reduced amount of allergen ingredient, such a dish is referred to as an allergen-controlled dish. When a dish which is not controlled in terms of allergens is ordered by another customer sitting at the same table, if this dish is erroneously provided to the customer who has ordered an allergen-controlled dish, this may cause a tremendous adverse effect on the health of the customer who has ordered the allergen-controlled dish. Thus, it is necessary to avoid such a situation.

In the technique disclosed in PTL 1 described above, in a case where the eating rule includes a rule about allergic ingredients, dishes including the allergic ingredients are excluded from the menu information of the recommended dishes.

However, PTL 1 merely discloses that allergic ingredients are removed from menu information and the resultant menu information is presented, and PTL 1 discloses nothing about providing the dish selected by the customer via the menu information to the customer's seat. Therefore, in the technique disclosed in PTL 1, there is a possibility that a wrong dish, from which allergic ingredients are not removed, is incorrectly provided to the customer's seat. Thus, in the technique disclosed in PTL 1, there is a possibility that the customer ingests a dish from which allergic ingredients are not removed, which may cause the customer to have a serious health problem.

Furthermore, since the information on allergic ingredients is sensitive information, it is necessary to prevent the information from being provided to a third party without the permission by the user.

PTL 2 discloses an order input screen that enables it to input and register ordered-dish information via an input device disposed at each seat set at each table. This order input screen includes a seat position image including seat objects indicating a plurality of seats, and a plurality of dish images corresponding to respective dish items. For example, a restaurant clerk touches a seat object corresponding to a particular seat in the seat position image, and then touches a dish image corresponding to a particular desired dish item. As a result, the dish item for a customer seated at the touched seat is selected.

As described above, in the technique disclosed in PTL 2, the seat and the dish item are manually associated with each other by the clerk via the order input screen. Therefore, there is a possibility that a seat and a dish item are incorrectly associated by erroneous inputting. In particular, such erroneous inputting is likely to occur when the restaurant is crowded. Furthermore, the order input screen disclosed in PTL 2 includes various kinds of information and objects in addition to the seat position image and the dish images as shown in FIG. 38 of PTL 2. This results in an increase in the possibility that an error occurs when inputting is performed on the order input screen disclosed in PTL 2. Thus, the technique disclosed in PTL 2 has similar problems to those in the technique disclosed in PTL 1.

To solve the problems described above, the present disclosure provides a technique from another viewpoint for preventing an allergen-uncontrolled dish from being erroneously ordered thereby preventing the allergen-uncontrolled dish from being ingested by a user and thus preventing the user from having a serious health problem.

A second object of the present disclosure is to provide a technique for preventing sensitive information stored in a first server from being leaked to the outside of the first server without permission of a user.

According to another aspect, the present disclosure provides a control method for controlling an information terminal that communicates, via a network, with a first server that manages allergy information related to a user corresponding to identification information identifying the user, including acquiring a restaurant ID and a seat ID indicating a seat of the user via a first operation screen displayed on a display of the information terminal of the user, acquiring, based on the restaurant ID, menu information indicating one or more dishes provided by a restaurant corresponding to the restaurant ID from a second server related to the restaurant corresponding to the restaurant ID via a network, transmitting the identification information stored in the information terminal to the first server, acquiring the allergy information related to the user from the first server based on the identification information, generating, based on the menu information and the allergy information, a personalized menu arranged for the user according to the allergy information, displaying the personalized menu on a second operation screen for accepting an order of a dish in the restaurant, the second operation screen being displayed on a display of the information terminal of the user, and transmitting ordered-dish information representing the dish selected from the personalized menu and the seat ID to the second server.

According to this aspect, for example, when a dish is ordered, the first operation screen is displayed on the display of the user's information terminal, and a restaurant ID and a user ID are acquired via this first operation screen. Based on the acquired restaurant ID, menu information indicating one or more dishes provided by the restaurant corresponding to the restaurant ID is acquired from the second server.

The information terminal stores identification information that identifies the user. Based on this identification information, the allergy information related to the user is acquired from the first server. Based on this allergy information and menu information, a personalized menu arranged for the user is generated according to the allergy information. This personalized menu is displayed on the display of the information terminal via the second operation screen. A dish is selected from the displayed personalized menu, and ordered-dish information indicating the selected dish is transmitted in association with the seat ID to the second server.

According to this aspect, as described above, in a series of processes in which the user orders a dish, the ordered-dish information indicating the dish selected by the user from the personalized menu is automatically associated with the seat of the user without a manual operation. Therefore, for example, even in a case where a plurality of users sit at the same table and each user orders a dish, it is possible to prevent an allergen-uncontrolled dish ordered by another user sitting at the same table from being carried to a seat of a user having food allergy. Thus, a user who is allergic to some ingredient can easily order a dish and can eat the ordered dish without worrying about a serious health problem.

Furthermore, in the present aspect, since the allergy information is not transmitted to the second server, it is possible to prevent the allergy information from leaking to the restaurant. Furthermore, in the present aspect, when the ordered-dish information is transmitted, the ordered-dish information is not associated with the identification information identifying the user, but the ordered-dish information is associated with the seat ID, it is possible to prevent the identification information from being leaked to the restaurant.

Note that the embodiments described above are merely examples, and the present disclosure may be applied to various applications.

In the embodiments described above, it is assumed by way of example that the seat of the user is a chair, but the present disclosure is not limited to this. For example, in a stand-up restaurant, one section of a table where the user eats food may be treated as a seat.

In each of the above embodiments, each constituent element may be configured by dedicated hardware or may be realized by executing a software program suitable for each constituent element. Each constituent element may be realized by a program execution unit such as a CPU or a processor by reading and executing a software program stored in a storage medium such as a hard disk or a semiconductor memory.

Note that the scope of the present disclosure is not limited by the above-described embodiments. It will be apparent to those skilled in the art that many various modifications may be applicable to the embodiments without departing from the spirit and scope of the present disclosure. Furthermore, constituent elements of different embodiments may be combined. In this case, any resultant combination also falls within the scope of the present disclosure.

A control method according to an aspect of the present disclosure is useful, in a restaurant that provides cooked dishes, for providing an allergen-controlled dish personalized for a specific user having allergy correctly to this specific user who ordered this dish.

What is claimed is:

1. A method of providing information in an information management system that communicates with a first server which manages allergy information related to a user corresponding to identification information identifying the user, the information management system including a second server that stores menu information indicating one or more dishes corresponding to a restaurant, the method comprising:
    acquiring a request for a personalized menu for the user from an information terminal of the user via a network;
    acquiring the identification information stored in the information terminal from the information terminal via the network;
    acquiring allergy information related to the user using the identification information from the first server via a network, the allergy information including information indicating a level of an allergic reaction of the user to each ingredient,
    generating, based on the menu information and the allergy information, the personalized menu arranged for the user according to the allergy information, the menu information including information indicating one or more ingredients contained in each dish and an amount of each ingredient; and
    transmitting the personalized menu to the information terminal to allow a selection of a dish via the personalized menu on the information terminal,
    wherein, the generating of the personalized menu includes:
    calculating a value using the amount of an ingredient included in a dish in the menu information and the level of the allergic reaction of the user to the ingredient; and
    in response to determining that the calculated value is equal to or larger than a criterion value, generating a changed dish in which the amount of the ingredient in the dish is reduced such that the calculated value becomes below the criterion value, and
    the personalized menu includes the changed dish.

2. The method of providing information according to claim 1, wherein
    upon acquiring the request for the personalized menu for the user, a seat ID indicating a seat of the user is acquired from the information terminal of the user, wherein the seat ID is acquired via an operation screen displayed on a display of the information terminal.

3. The method of providing information according to claim 2, wherein
    the seat ID is acquired by reading, via the operation screen, an identification code prepared at a location corresponding to a seat at a table where the user is seated.

4. The method of providing information according to claim 3, wherein the identification code includes a QR code.

5. The method of providing information according to claim 1, wherein
    the reducing of the allergy ingredient includes removing the allergy ingredient such that an amount of the ingredient is zero.

6. The method of providing information according to claim 1, wherein the identification information includes a user ID.

7. The method of providing information according to claim 1, wherein the first server is different from the second server.

8. The method of providing information according to claim 1, wherein
    the first server distributedly manages at least one of biological information including the allergy information, preference information including user's item purchase history information or dish order history information, or behavior history information including location information of the user.

9. A method of providing information in an information management system that communicates with a first server which manages allergy information related to a user corresponding to identification information identifying the user, the information management system including a second server that stores menu information indicating one or more dishes corresponding to a restaurant, the method comprising:
    acquiring a request for a personalized menu for the user from an information terminal of the user via a network;
    acquiring the identification information stored in the information terminal from the information terminal via the network;
    acquiring the allergy information related to the user from the first server via a network, the allergy information including information indicating a level of an allergic reaction of the user to each ingredient,
    generating, based on the menu information and the allergy information, the personalized menu arranged for the user according to the allergy information, the menu information including information indicating one or more ingredients contained in each dish and an amount of each ingredient; and
    transmitting the personalized menu to the information terminal to allow a selection of a dish via the personalized menu on the information terminal,
    wherein, in the generating of the personalized menu,
    a value is calculated using the amount of an ingredient included in a dish in the menu information and the level of the allergic reaction of the user to the ingredient,
    in response to determining that the calculated value is equal to or larger than a criterion value, the dish is determined as an allergy dish that includes an allergy ingredient that causes allergy,
    in response to determining that the calculated value is smaller than the criterion value, the dish is determined as a low-allergy dish, and
    the personalized menu is generated by excluding the allergy dish included in the menu information and including the low-allergy dish in the menu information.

10. The method of providing information according to claim 9, wherein
    upon acquiring the request for the personalized menu for the user, a seat ID indicating a seat of the user is acquired from the information terminal of the user, wherein the seat ID is acquired via an operation screen displayed on a display of the information terminal.

11. A method of providing information in an information management system that includes a first server and communicates with a second server, wherein the first server manages allergy information related to a user corresponding to identification information identifying the user, and the second server stores menu information indicating one or more dishes corresponding to a restaurant, the method comprising:

outputting to the second server a request for sending of the menu information to the first server, based on a request for a personalized menu for the user acquired from an information terminal of the user via a network;

acquiring the identification information stored in the information terminal from the information terminal via the network;

acquiring the menu information from the second server;

generating, based on the menu information and the allergy information related to the user corresponding to the identification information, the personalized menu arranged for the user according to the allergy information, the menu information including information indicating one or more ingredients contained in each dish and an amount of each ingredient, the allergy information including information indicating a level of an allergic reaction of the user to each ingredient; and transmitting the personalized menu to the information terminal to allow a selection of a dish via the personalized menu on the information terminal, wherein, the generating of the personalized menu includes:

calculating a value using the amount of an ingredient included in a dish in the menu information and the level of the allergic reaction of the user to the ingredient; and in response to determining that the calculated value is equal to or larger than a criterion value, generating a changed dish in which the amount of the ingredient in the dish is reduced such that the calculated value becomes below the criterion value, and the personalized menu includes the changed dish.

12. The method of providing information according to claim 11, wherein upon acquiring the request for the personalized menu for the user, a seat ID indicating a seat of the user is acquired from the information terminal of the user, wherein the seat ID is acquired via an operation screen displayed on a display of the information terminal.

13. The method of providing information according to claim 12, wherein the seat ID is acquired by reading, via the operation screen, an identification code prepared at a location corresponding to a seat at a table where the user is seated.

14. The method of providing information according to claim 13, wherein the identification code includes a QR code.

15. The method of providing information according to claim 11, wherein the reducing of the allergy ingredient includes removing the allergy ingredient such that the amount of the ingredient is zero.

16. The method of providing information according to claim 11, wherein the identification information includes a user ID.

17. The method of providing information according to claim 11, wherein the first server is different from the second server.

18. The method of providing information according to claim 11, wherein the first server distributedly manages at least one of biological information including the allergy information, preference information including user's item purchase history information or dish order history information, or behavior history information including location information of the user.

19. A method of providing information in an information management system that includes a first server and communicates with a second server, wherein the first server manages allergy information related to a user corresponding to identification information identifying the user, and the second server stores menu information indicating one or more dishes corresponding to a restaurant, the method comprising:

outputting to the second server a request for sending of the menu information to the first server, based on a request for a personalized menu for the user acquired from an information terminal of the user via a network;

acquiring the identification information stored in the information terminal from the information terminal via the network;

acquiring the menu information from the second server;

generating, based on the menu information and the allergy information related to the user corresponding to the identification information, the personalized menu arranged for the user according to the allergy information, the menu information including information indicating one or more ingredients contained in each dish and an amount of each ingredient, the allergy information including information indicating a level of an allergic reaction of the user to each ingredient; and transmitting the personalized menu to the information terminal to allow a selection of a dish via the personalized menu on the information terminal, wherein, in the generating of the personalized menu, a value is calculated using the amount of an ingredient included in a dish in the menu information and the level of the allergic reaction of the user to the ingredient, in response to determining that the calculated value is equal to or larger than a criterion value, the dish is determined as an allergy dish that includes an allergy ingredient that causes allergy, in response to determining that the calculated value is smaller than the criterion value, the dish is determined as a low-allergy dish, and the personalized menu is generated by excluding the allergy dish included in the menu information and including the low-allergy dish in the menu information.

20. The method of providing information according to claim 19, wherein upon acquiring the request for the personalized menu for the user, a seat ID indicating a seat of the user is acquired from the information terminal of the user, wherein the seat ID is acquired via an operation screen displayed on a display of the information terminal.

* * * * *